(12) United States Patent
Patterson et al.

(10) Patent No.: US 11,608,528 B2
(45) Date of Patent: Mar. 21, 2023

(54) METHODS AND COMPOSITIONS FOR SEQUENCING DOUBLE STRANDED NUCLEIC ACIDS USING RCA AND MDA

(71) Applicant: Pacific Biosciences of California, Inc., Menlo Park, CA (US)

(72) Inventors: Kurt Patterson, San Diego, CA (US); Hari K. K. Subramanian, San Diego, CA (US); Brittany A. Rohrman, San Diego, CA (US); Fabian Block, San Diego, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 17/814,062

(22) Filed: Jul. 21, 2022

(65) Prior Publication Data

US 2022/0349002 A1 Nov. 3, 2022

Related U.S. Application Data

(63) Continuation of application No. PCT/US2021/020564, filed on Mar. 3, 2021.
(Continued)

(51) Int. Cl.
*C12P 19/34* (2006.01)
*C12Q 1/6874* (2018.01)
(Continued)

(52) U.S. Cl.
CPC ......... *C12Q 1/6874* (2013.01); *C12Q 1/6806* (2013.01); *C12Q 1/6853* (2013.01)

(58) Field of Classification Search
CPC .................................................. C12Q 1/6869
See application file for complete search history.

(56) References Cited

U.S. PATENT DOCUMENTS

| 5,599,675 A | 2/1997 | Brenner |
| 5,750,341 A | 5/1998 | Macevicz |
(Continued)

FOREIGN PATENT DOCUMENTS

| WO | WO1989010977 | 11/1989 |
| WO | WO1991006678 | 5/1991 |
(Continued)

OTHER PUBLICATIONS

Bains et al., "A novel method for nucleic acid sequence determination," Journal of Theoretical Biology 1988, 135(3), 303-307.
(Continued)

*Primary Examiner* — Kenneth R Horlick
(74) *Attorney, Agent, or Firm* — Sheppard, Mullin, Richter & Hampton LLP

(57) ABSTRACT

A method for determining sequences from sense and antisense strands of a nucleic acid, including (a) providing a nucleic acid cluster attached to a solid support, wherein the nucleic acid cluster includes a sense strand and an antisense strand of a concatemer, the concatemer including multiple copies of a sequence unit, the sequence unit including a target sequence and a primer binding site; (b) hybridizing a primer to a primer binding site in the antisense strand; (c) extending the primer along the antisense strand to determine the sequence from at least a portion of the target sequence in the antisense strand; (d) hybridizing a second primer to a primer binding site in the sense strand; and (e) extending the second primer along the sense strand to determine the sequence from at least a portion of the target sequence in the sense strand.

19 Claims, 26 Drawing Sheets

Specification includes a Sequence Listing.

Related U.S. Application Data

(60) Provisional application No. 62/984,438, filed on Mar. 3, 2020.

(51) Int. Cl.
*C12Q 1/6806* (2018.01)
*C12Q 1/6853* (2018.01)

(56) References Cited

U.S. PATENT DOCUMENTS

| | | | |
|---|---|---|---|
| 6,210,891 | B1 | 4/2001 | Nyren et al. |
| 6,258,568 | B1 | 7/2001 | Nyren |
| 6,266,459 | B1 | 7/2001 | Walt et al. |
| 6,274,320 | B1 | 8/2001 | Rothberg et al. |
| 6,280,949 | B1 | 8/2001 | Lizardi |
| 6,323,009 | B1 | 11/2001 | Lasken et al. |
| 6,355,431 | B1 | 3/2002 | Chee et al. |
| 6,576,448 | B2 | 6/2003 | Weissman et al. |
| 6,670,126 | B2 | 12/2003 | Kingsmore et al. |
| 6,737,236 | B1 | 5/2004 | Pieken et al. |
| 6,770,441 | B2 | 8/2004 | Dickinson et al. |
| 6,797,474 | B2 | 9/2004 | Lizardi |
| 6,830,884 | B1 | 12/2004 | Hafner et al. |
| 6,859,570 | B2 | 2/2005 | Walt et al. |
| 7,057,026 | B2 | 6/2006 | Barnes et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,329,860 | B2 | 2/2008 | Feng et al. |
| 7,375,234 | B2 | 5/2008 | Sharpless et al. |
| 7,405,281 | B2 | 7/2008 | Xu et al. |
| 7,414,116 | B2 | 8/2008 | Milton et al. |
| 7,427,673 | B2 | 9/2008 | Balasubramanian et al. |
| 7,427,678 | B2 | 9/2008 | Pieken et al. |
| 7,544,794 | B1 | 6/2009 | Benner |
| 7,622,294 | B2 | 11/2009 | Walt et al. |
| 7,763,736 | B2 | 7/2010 | Sharpless et al. |
| 7,910,354 | B2 | 3/2011 | Drmanac et al. |
| 7,956,171 | B2 | 6/2011 | Siddiqi |
| 8,034,923 | B1 | 10/2011 | Benner et al. |
| 8,039,817 | B2 | 10/2011 | Feng et al. |
| 8,071,755 | B2 | 12/2011 | Efcavitch et al. |
| 8,105,784 | B2 | 1/2012 | Rigatti et al. |
| 8,241,573 | B2 | 8/2012 | Banerjee et al. |
| 8,808,989 | B1 | 8/2014 | Efcavitch et al. |
| 9,045,796 | B2 | 6/2015 | Gunderson et al. |
| 9,228,228 | B2 | 1/2016 | Drmanac et al. |
| 9,399,798 | B2 | 7/2016 | Stupi et al. |
| 9,498,763 | B2 | 11/2016 | Liu et al. |
| 9,624,538 | B2 | 4/2017 | Church et al. |
| 10,227,647 | B2 | 3/2019 | Ke et al. |
| 10,400,272 | B1 | 9/2019 | Middleton et al. |
| 11,085,073 | B2 * | 8/2021 | Korfhage ............ C12Q 1/6844 |
| 11,220,707 | B1 | 1/2022 | Arslan et al. |
| 11,236,388 | B1 | 2/2022 | Arslan et al. |
| 11,242,512 | B2 | 2/2022 | Iyidogan |
| 2003/0217381 | A1 | 11/2003 | Croughan |
| 2004/0002090 | A1 | 1/2004 | Mayer et al. |
| 2004/0125424 | A1 | 7/2004 | Moon et al. |
| 2004/0132205 | A1 | 7/2004 | Moon et al. |
| 2004/0185481 | A1 | 9/2004 | Numajiri |
| 2004/0233485 | A1 | 11/2004 | Moon et al. |
| 2004/0263923 | A1 | 12/2004 | Moon et al. |
| 2005/0069939 | A1 | 3/2005 | Wang et al. |
| 2006/0024711 | A1 | 2/2006 | Lapidus et al. |
| 2007/0099208 | A1 | 5/2007 | Drmanac et al. |
| 2008/0108082 | A1 | 5/2008 | Rank et al. |
| 2008/0108804 | A1 | 5/2008 | Hayashizaki et al. |
| 2009/0018024 | A1 | 1/2009 | Church et al. |
| 2009/0026082 | A1 | 1/2009 | Rothberg et al. |
| 2009/0029385 | A1 | 1/2009 | Christians et al. |
| 2009/0088327 | A1 | 4/2009 | Rigatti et al. |
| 2009/0118128 | A1 | 5/2009 | Liu et al. |
| 2009/0127589 | A1 | 5/2009 | Rothberg et al. |
| 2009/0143235 | A1 | 6/2009 | Drmanac et al. |
| 2009/0181370 | A1 | 7/2009 | Smith |
| 2009/0197257 | A1 | 8/2009 | Harris |
| 2009/0272914 | A1 | 11/2009 | Feng et al. |
| 2010/0111768 | A1 | 5/2010 | Banerjee et al. |
| 2010/0137143 | A1 | 6/2010 | Rothberg et al. |
| 2010/0173303 | A1 | 7/2010 | Ronaghi et al. |
| 2010/0279882 | A1 | 11/2010 | Ronaghi et al. |
| 2010/0282617 | A1 | 11/2010 | Rothberg et al. |
| 2011/0009276 | A1 | 1/2011 | Vermaas et al. |
| 2012/0270305 | A1 | 10/2012 | Reed et al. |
| 2013/0178369 | A1 | 7/2013 | Burns et al. |
| 2013/0281306 | A1 | 10/2013 | Rigatti et al. |
| 2015/0044687 | A1 | 2/2015 | Schmitt et al. |
| 2015/0152492 | A1 | 6/2015 | Brown et al. |
| 2016/0237488 | A1 | 8/2016 | Ke et al. |
| 2016/0376647 | A1 | 12/2016 | Travers et al. |
| 2017/0022553 | A1 | 1/2017 | Vijayan et al. |
| 2017/0314072 | A1 | 11/2017 | Vijayan et al. |
| 2018/0044727 | A1 | 2/2018 | Vijayan et al. |
| 2018/0100192 | A1 | 4/2018 | Boutell |
| 2018/0105871 | A1 * | 4/2018 | Korfhage ............ C12Q 1/6846 |
| 2018/0155698 | A1 | 6/2018 | Iyidogan et al. |
| 2018/0230533 | A1 | 8/2018 | Church et al. |
| 2018/0280975 | A1 | 10/2018 | Kilcoin et al. |
| 2018/0282800 | A1 | 10/2018 | Li et al. |
| 2019/0169688 | A1 | 6/2019 | Stromberg et al. |
| 2019/0241945 | A1 | 8/2019 | Malyshev et al. |
| 2019/0345544 | A1 | 11/2019 | Middleton et al. |
| 2019/0367974 | A1 | 12/2019 | Fleischer et al. |
| 2020/0032317 | A1 | 1/2020 | Rohrman et al. |
| 2020/0032322 | A1 | 1/2020 | Subramanian et al. |
| 2020/0255821 | A1 | 8/2020 | Wang et al. |
| 2021/0189460 | A1 * | 6/2021 | Hosono ............... C12Q 1/6869 |
| 2021/0189483 | A1 | 6/2021 | Drmanac et al. |
| 2021/0332430 | A1 | 10/2021 | Arslan et al. |

FOREIGN PATENT DOCUMENTS

| | | |
|---|---|---|
| WO | WO2000063437 | 10/2000 |
| WO | WO2004018497 | 3/2004 |
| WO | WO2005065814 | 7/2005 |
| WO | WO2007123744 | 11/2007 |
| WO | WO2015188192 | 12/2015 |
| WO | WO2016038381 | 3/2016 |
| WO | WO2016156845 | 10/2016 |
| WO | WO2021236792 | 11/2021 |

OTHER PUBLICATIONS

Bentley et al., "Accurate whole human genome sequencing using reversible terminator chemistry," Nature 2008, 456, 53-59.

Drmanac et al., "Accurate sequencing by hybridization for DNA diagnostics and individual genomics," Nature Biotechnology 1998, 16, 54-58.

Fodor et al., "Light-Directed, Spatially Addressable Parallel Chemical Synthesis," Science 1991, 251, 767-773.

Hollinger & Hudson, "Engineered antibody fragments and the rise of single domains," Nature Biotechnology 2005, 23(9), 1126-1136.

International Search Report and Written Opinion dated May 14, 2021 in PCT Patent Application No. PCT/US2021/020564.

Keefe et al., "One-Step Purification of Recombinant Proteins Using a Nanomolar-Affinity Streptavidin-Binding Peptide, the SBP-Tag," Protein Expression and Purification 2001, 23, 440-446.

Korfhage et al., "Clonal rolling circle amplification for on-chip DNA cluster generation," Biology Methods and Protocols 2017, 1-10.

Kwok et al., "Effects of primer-template mismatches on the polymerase chain reaction: Human immunodeficiency virus type 1 model studies," Nucleic Acids Research 1990, 18(4), 999-1005.

Langmead & Salzberg et al., "Fast gapped-read alignment with Bowtie 2," Nat Methods 2012, 9(4), 357-359.

Lizardi et al., "Mutation detection and single-molecule counting using isothermal rolling-circle amplification," Nat Genet. 1998, 19, 225-232.

Ronaghi et al., "A Sequencing Method Based on Real-Time Pyrophosphate," Science 1998, 281(5375), 363-365.

(56) References Cited

OTHER PUBLICATIONS

Ronaghi, "Pyrosequencing Sheds Light on DNA Sequencing," Genome Res. 2001, 11, 3-11.
Ronaghi et al., "Real-time DNA sequencing using detection of pyrophosphate release," Anal Biochem. 1996, 242(1), 84-89.
Shendure et al., "Accurate Multiplex Polony Sequencing of an Evolved Bacterial Genome," Science 2005, 309, 1728-1732.
Turcatti et al., "A new class of cleavable fluorescent nucleotides: synthesis and optimization as reversible terminators for DNA sequencing by synthesis," Nucl. Acids. Res. 2008, 36(4), in 13 pages.
Yamamoto et al., "Design and Synthesis of Biotin Analogues Reversibly Binding with Streptavidin," Chemistry, An Asian Journal 2015, 10(4), 1071-1078.

\* cited by examiner

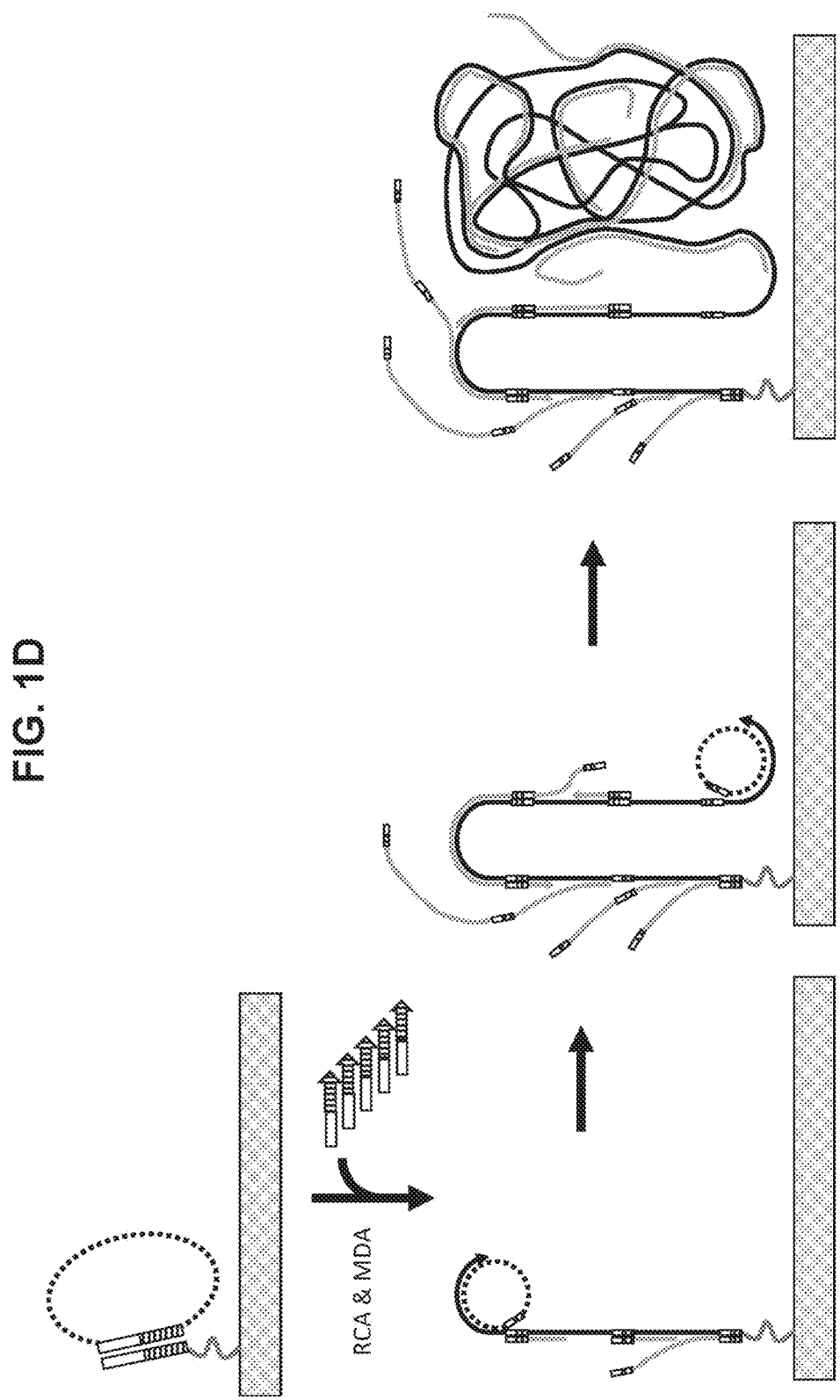

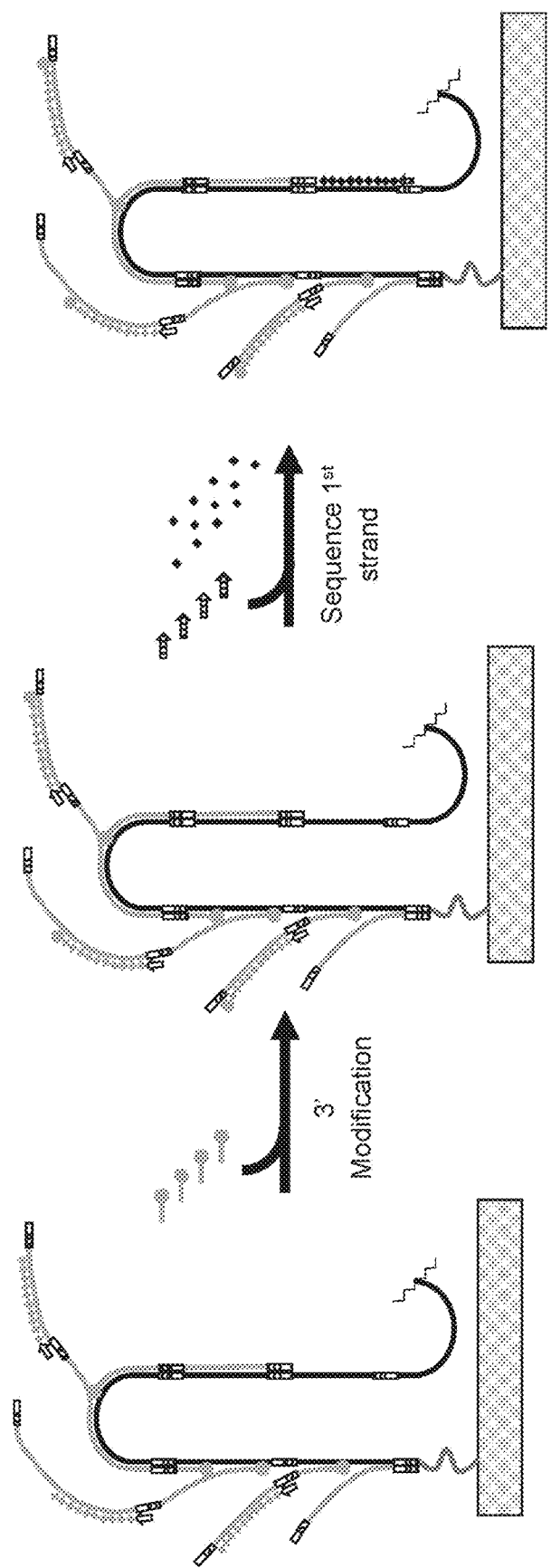

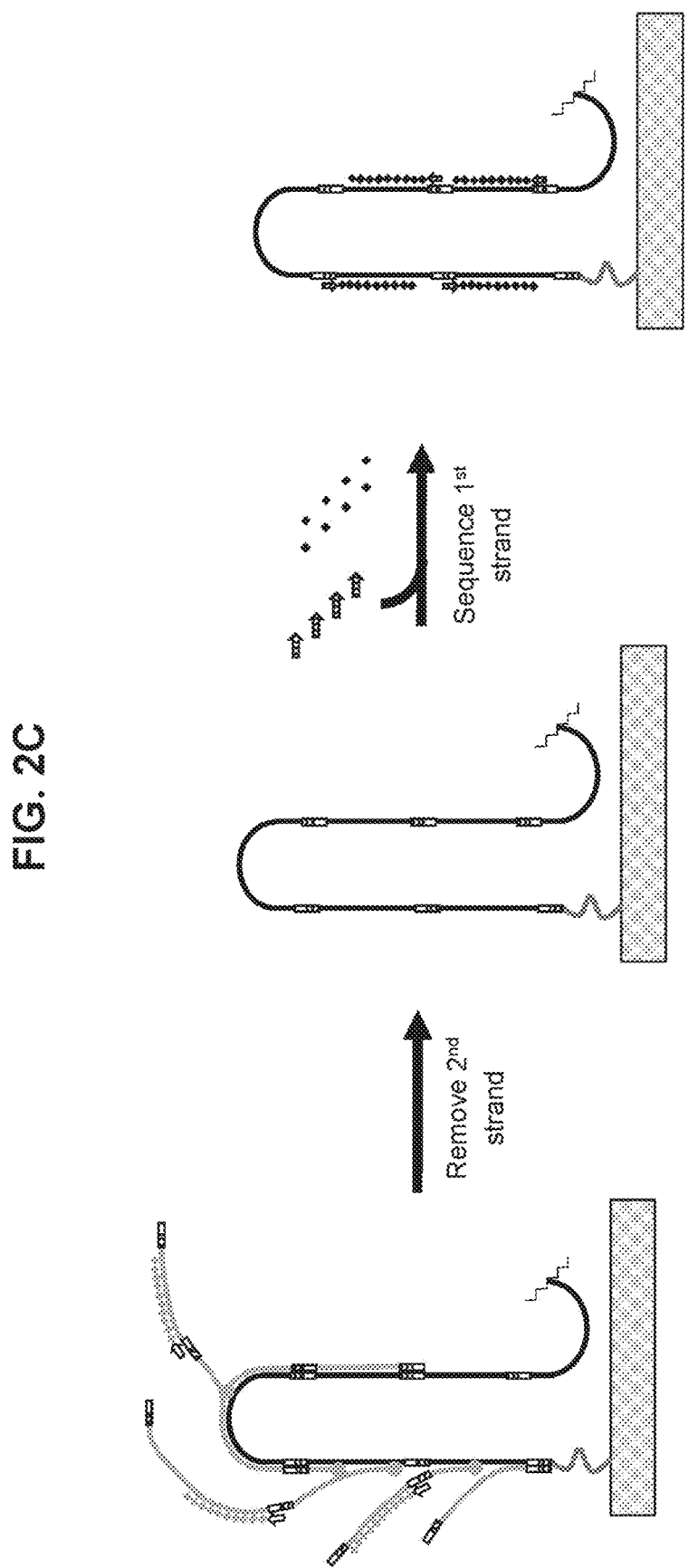

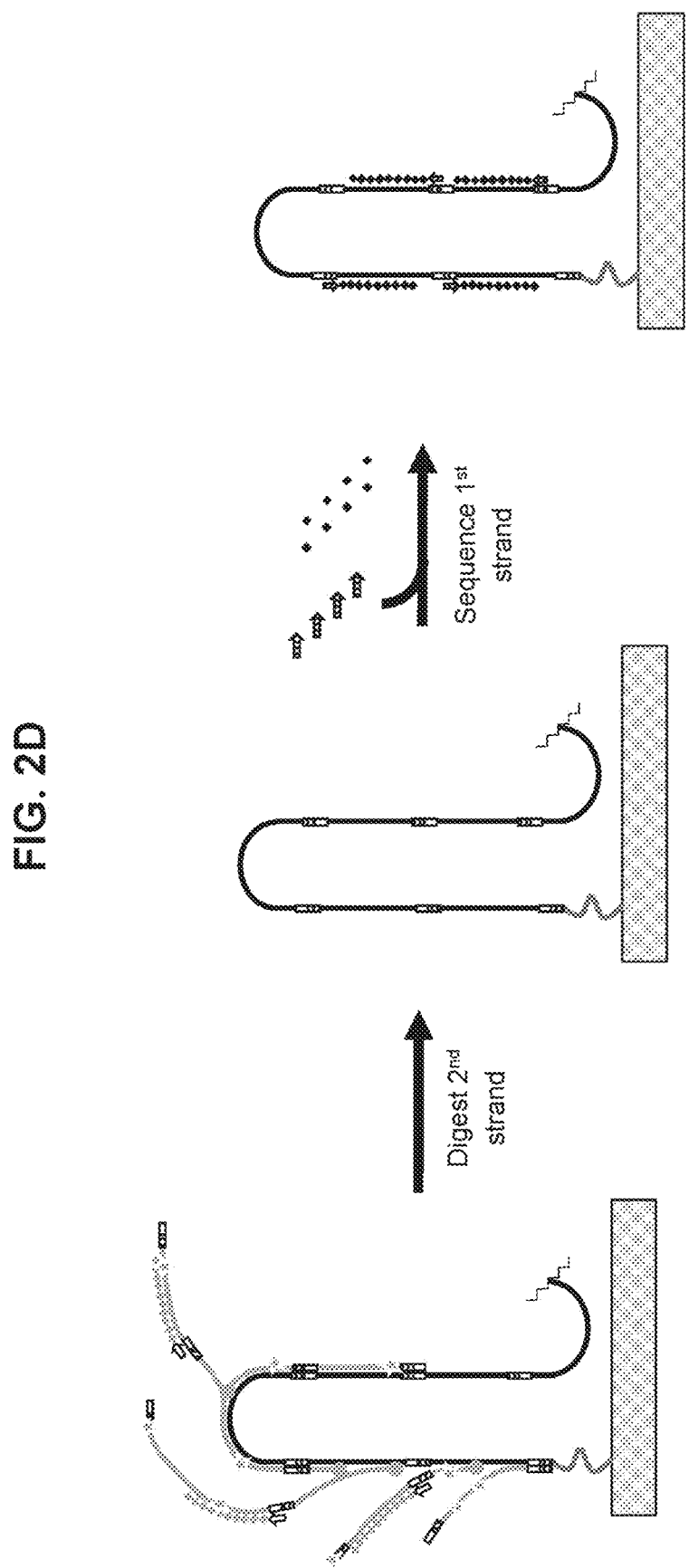

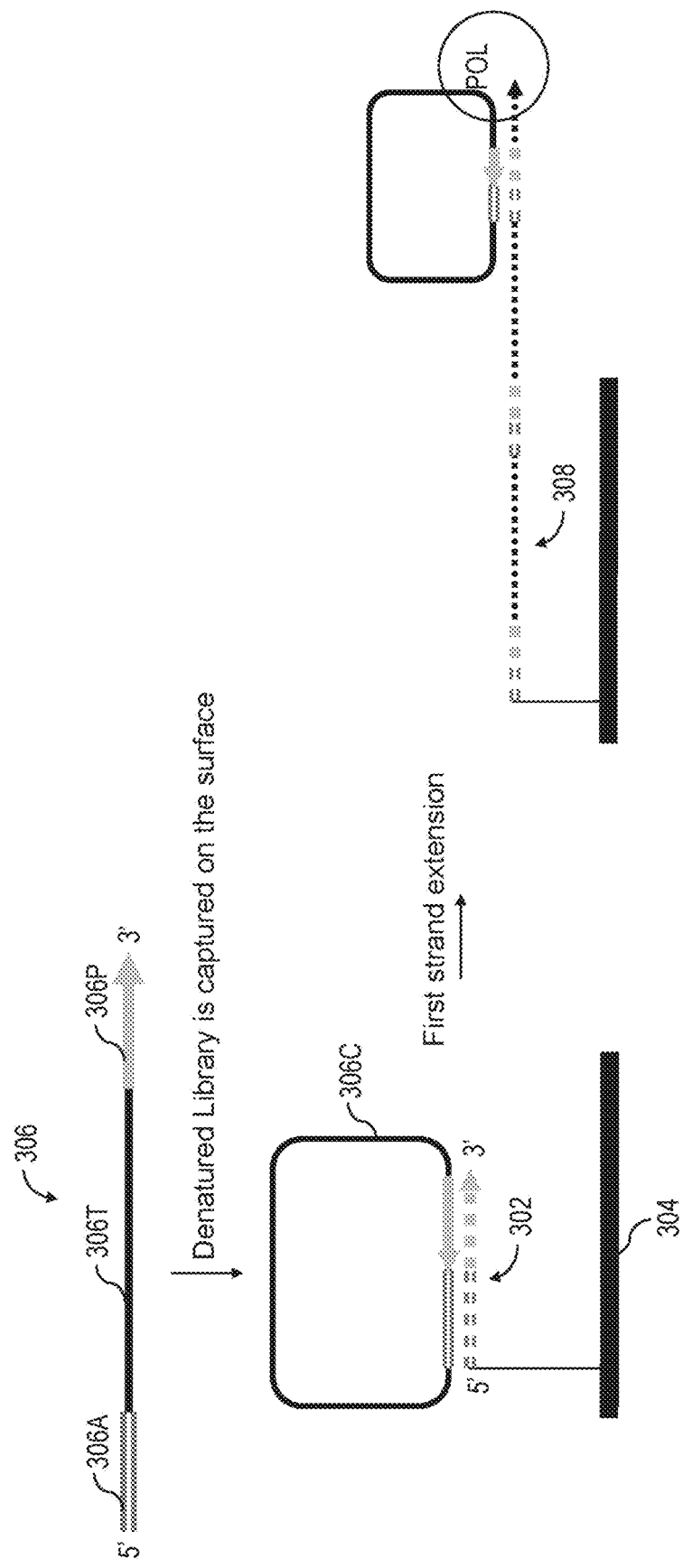

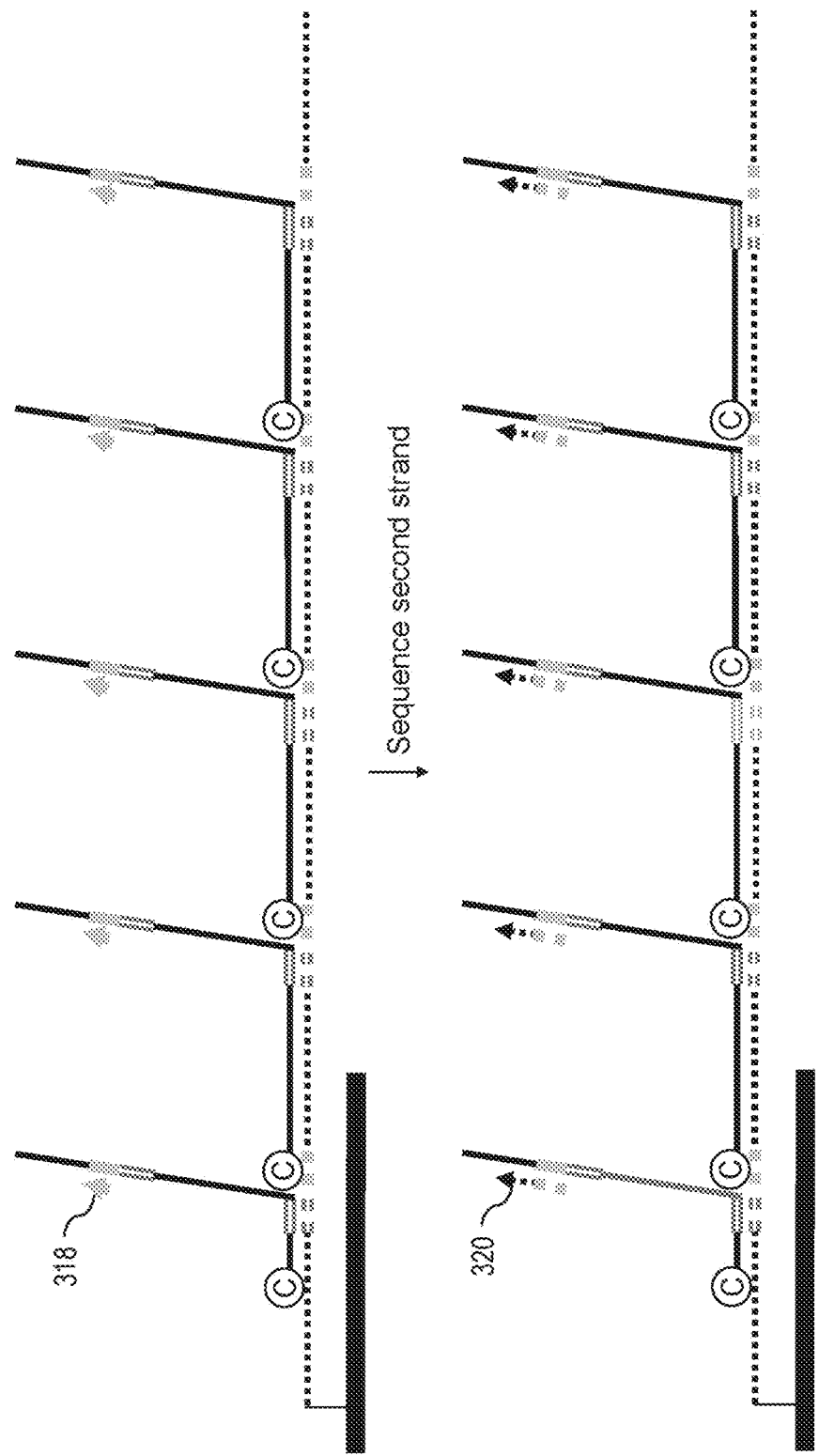

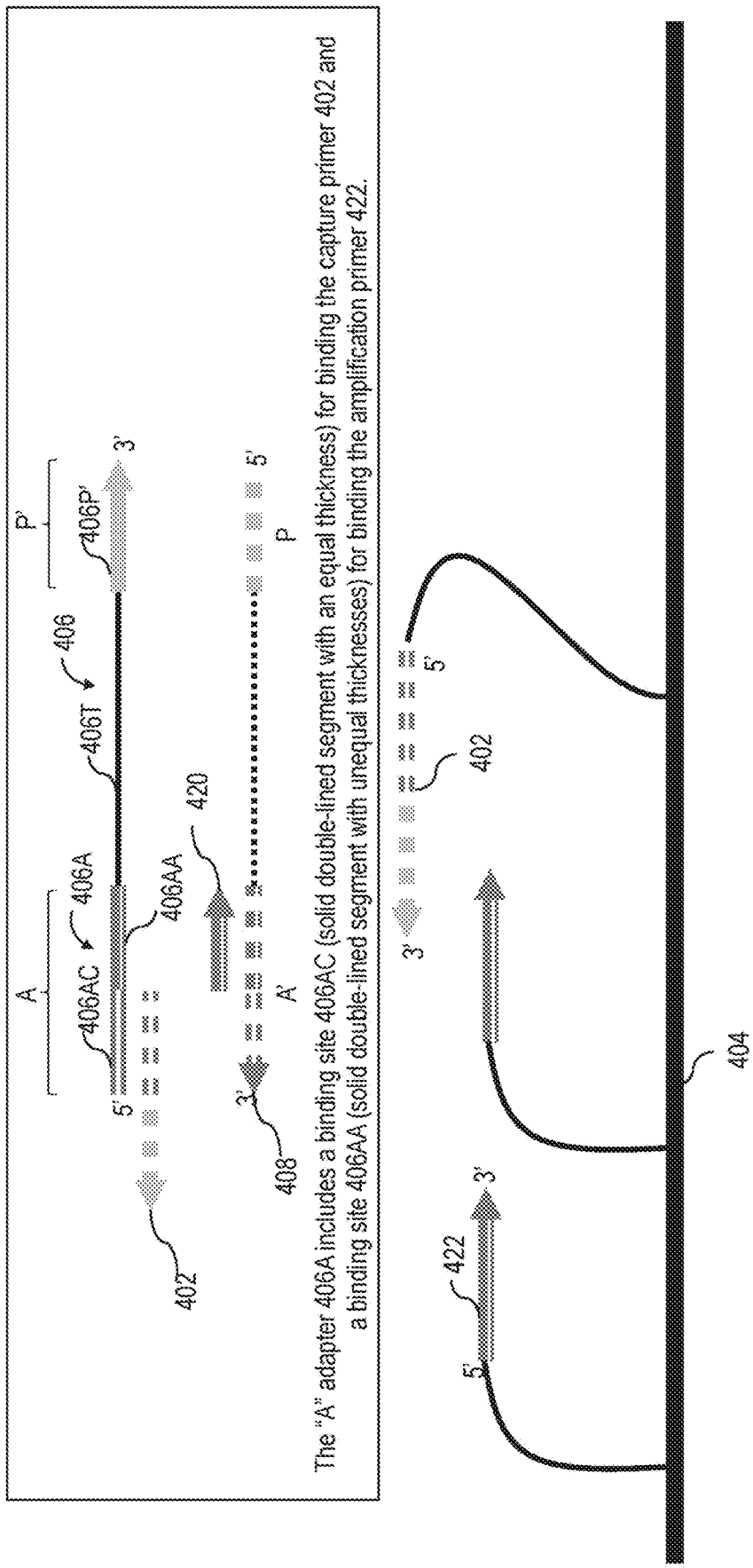

METHODS AND COMPOSITIONS FOR SEQUENCING DOUBLE STRANDED NUCLEIC ACIDS USING RCA AND MDA

RELATED APPLICATIONS

The present application is a continuation application of International Application No. PCT/US2021/020564, filed on Mar. 3, 2021, and published as WO 2021/178467 on Sep. 10, 2021, which claims priority to U.S. Provisional Application No. 62/984,438, filed on Mar. 3, 2020; the content of each of which is incorporated herein by reference in its entirety.

REFERENCE TO SEQUENCE LISTING

The present application includes a Sequence Listing in electronic format. The Sequence Listing is provided as a file entitled Sequence_Listing_42HB-328033-WO, created Jul. 20, 2022, which is 13 kilobytes in size. The information in the electronic format of the Sequence Listing is incorporated herein by reference in its entirety.

BACKGROUND

The present disclosure relates generally to obtaining sequence information from nucleic acids and has specific applicability to dual strand or paired end sequencing of nucleic acids.

Many nucleic acid sequencing methods involve extension of a primer along a target nucleic acid template. The primer can be extended by serial incorporation of nucleotides in a template-dependent fashion, typically using a polymerase, and the identity and order of incorporated nucleotides is observed in order to determine the sequence for the target nucleic acid. When performing nucleic acid sequencing, it is frequently desirable to sequence more than one region of a target nucleic acid. For example, it can be informative to sequence opposite strands of the target nucleic acid in opposite directions. Such dual strand sequencing can provide the advantage of increasing the total amount of sequence information available from a given target nucleic acid, especially when the length of the target exceeds the read lengths typically obtainable from the sequencing method employed. In situations where the read lengths of the sequencing method are of the same order as template length, bi-directional sequencing can provide advantages, such as independent validation of sequence information resulting from comparison of the "sense" strand read with the corresponding "antisense" read. Various methods of dual strand or paired end sequencing have been proposed, but these methods add time and expense compared to single strand sequencing approaches. For example, requirements to synthesize complementary strands and/or remove strands between two sequencing reads can be cumbersome, time consuming and expensive, and may introduce errors into the sequence results if a strand for second read sequencing is generated from a strand that has been subjected to sequencing.

Thus, there exists a need for efficient methods of sequencing multiple regions of a target nucleic acid. The present invention satisfies this need and provides related advantages as well.

BRIEF SUMMARY

The present disclosure provides a method for determining sequences from sense and antisense strands of a nucleic acid. The method can include steps of (a) providing a nucleic acid cluster attached to a solid support, wherein the nucleic acid cluster includes a sense strand of a concatemer and an antisense strand of the concatemer, wherein the concatemer includes multiple copies of a sequence unit linked in series, wherein the sequence unit includes a target sequence and a primer binding site; (b) hybridizing a primer to the primer binding site in a sequence unit of the antisense strand in the cluster; (c) extending the primer along the antisense strand to determine the sequence from at least a portion of the target sequence in the antisense strand; (d) hybridizing a second primer to the primer binding site in a sequence unit of the sense strand; and (e) extending the second primer along the sense strand to determine the sequence from at least a portion of the target sequence in the sense strand. Optionally, subsequent to step (c) and prior to step (d), a capping moiety or a blocking moiety can be incorporated into the primer extended along the antisense strand such that the primer is not further extended during step (e) when the second primer is extended along the sense strand.

Also provided herein is a composition comprising a solid support having attached thereto a nucleic acid cluster comprising a sense strand of a concatemer and an antisense strand of the concatemer, wherein the concatemer comprises multiple copies of a sequence unit linked in series, wherein the sequence unit comprises a target sequence and a primer binding site, optionally wherein the sense strand is covalently attached to the solid support, and optionally wherein the antisense strand is covalently attached to the solid support.

BRIEF DESCRIPTION OF THE DRAWINGS

FIG. 1D shows a diagrammatic representation of extending an immobilized primer (e.g., a capture primer) along a circular template nucleic acid via rolling circle amplification to produce an immobilized sense strand of a concatemer and in the same reaction extending a plurality of primers (e.g., capture primers) along the immobilized sense strand to produce a cluster having the immobilized sense strand hybridized to a plurality of antisense strands. A primer of the present disclosure (e.g., a capture primer or an amplification primer) can be any nucleic acid, such as RNA, DNA, DNA/RNA chimeric, other molecules capable of hybridizing to the another nucleic acid (e.g., a template nucleic acid, a sense strand, or an antisense strand).

FIG. 2B shows a diagrammatic representation of a method for treating a nucleic acid cluster to block or cap 3' ends of primer extension products after sequencing second strands (e.g., antisense strands) in the cluster and then sequencing first strands (e.g., sense strands) in the presence of the first strands in the cluster. FIG. 2C shows a diagrammatic representation of a method for treating a nucleic acid cluster to remove second strands (e.g., antisense strands) and primer extension products after sequencing the first strands in the cluster and then sequencing first strands (e.g., sense strands) in the absence of the second strands and primer extension products in the cluster. FIG. 2D shows a diagrammatic representation of a method for treating a nucleic acid cluster to digest second strands (e.g., antisense strands) and primer extension products after sequencing the second strands in the cluster and then sequencing first strands (e.g., sense strands) in the absence of the second strands and primer extension products in the cluster.

FIGS. 3A-3F show a non-limiting exemplary illustration of a method for determining sequences from first and second strands (e.g., sense and antisense strands) of a nucleic acid. FIG. 3A shows clustering to make the first strand. FIG. 3B shows sequencing the first strand. FIG. 3C shows the extension product of a sequencing primer is further extended with strand displacing polymerase. FIG. 3D shows further extension of the extension product from sequencing the first strand results in second strand scales. FIG. 3E shows blocking 3' ends of the second strands. FIG. 3F shows priming and sequencing second strand scales. In FIGS. 3A-3F, the first strands are illustrated as dotted lines, and the second strands are illustrated as solid lines.

FIGS. 4A-4F show a non-limiting exemplary illustration of a method for determining sequences from sense and antisense strands of a nucleic acid. FIG. 4A shows two surface primers attached to surface. FIG. 4B shows library hybridizes on splint and gets ligated. FIG. 4C shows a polymerase carries out RCA on the first strand. FIG. 4D shows second surface primers hybridized to first strand. FIG. 4E shows scaling occurs in same RCA reaction by a polymerase (not shown for simplicity). RCA and MDA can be performed simultaneously or sequentially. For example, 3' ends of the amplification primers may include capping moieties during RCA such that RCA and MDA occur sequentially. FIG. 4F shows priming the displaced scales with sequencing primer.

DETAILED DESCRIPTION

Figure 2A:
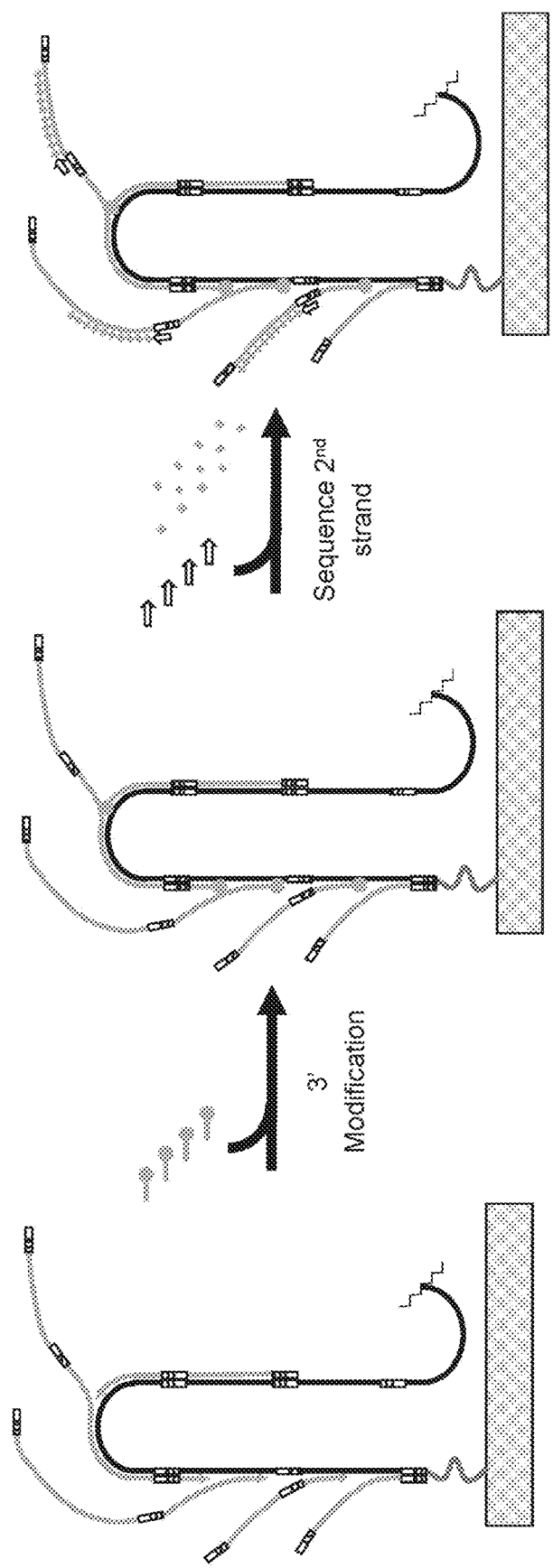
FIG. 2A shows a diagrammatic representation of a method for treating a nucleic acid cluster to block or cap 3' ends of second strands (e.g., antisense strands) and then sequencing the second strands in the cluster.

A variety of methods have been developed for determining the sequences of two different portions of a nucleic acid template. In many cases these methods are configured to determine the sequences at opposite ends of a nucleic acid template and are thus referred to as "paired end" sequencing. Typically, the sequence of the first end is determined by extending a first primer along the first strand of the nucleic acid template and then the sequence of the second end is determined by extending a second primer along the second strand of the nucleic acid template. Since the direction of the nucleotides in one strand is opposite to their direction in the other strand (the strands are said to be 'antiparallel'), the first and second primers are extended in opposite directions and toward each other. Because of this orientation, inter alia, other paired end sequencing methods require each of the strands to be sequenced in the absence of the other strand. Accordingly, paired end methods typically require steps of removing strands or synthesizing strands between the two sequencing reads. The present disclosure provides methods for sequencing a sense strand of a target nucleic acid in the presence of the antisense strand of the target nucleic acid. FIGS. 2A-2B illustrate a non-limiting exemplary method of sequencing a sense strand of a target nucleic acid in the presence of the antisense strand of the target nucleic acid.

Methods and compositions herein relate to paired read sequencing of concatemeric library templates. Primers are annealed to the concatemers and extended, often using a strand displacing polymerase, to produce a multimeric, partially double stranded molecule having a continuous concatemeric strand and a series of distinct extension products that are annealed to the concatemeric strand at their 3' ends. Their 5' ends are single stranded and exposed for sequencing, for example using primers that anneal to a conserved region in the concatemeric repeat which they have copied. After sequencing these templates, they are optionally removed or degraded, such that the multimeric, partially double stranded molecule is exposed and can be sequenced using primers that anneal, for example, to conserved regions in the concatemeric repeat. In alternate embodiments the concatemeric repeat strand is sequenced prior to generation of the series of distinct extension products. Similarly, in yet additional embodiments the concatemeric repeat strand is sequenced concurrently with generation of the series of distinct extension products, such that the extension products are the result of sequencing.

In a more lengthy portrayal of the compositions and methods herein, one starts with a linear nucleic acid, such as a library constituent, having a distinct 5' and 3' adapter. The linear nucleic acid is annealed to a guide oligo such as a surface bound oligo, having regions complementary to the distinct 5' and 3' adapters of the linear nucleic acid, and oriented so as to position the linear nucleic acid 5' and 3' ends in close proximity. See FIG. 1A. The linear nucleic acid 5' and 3' ends are ligated so as to circularize the liner nucleic acid.

Figure 1A:
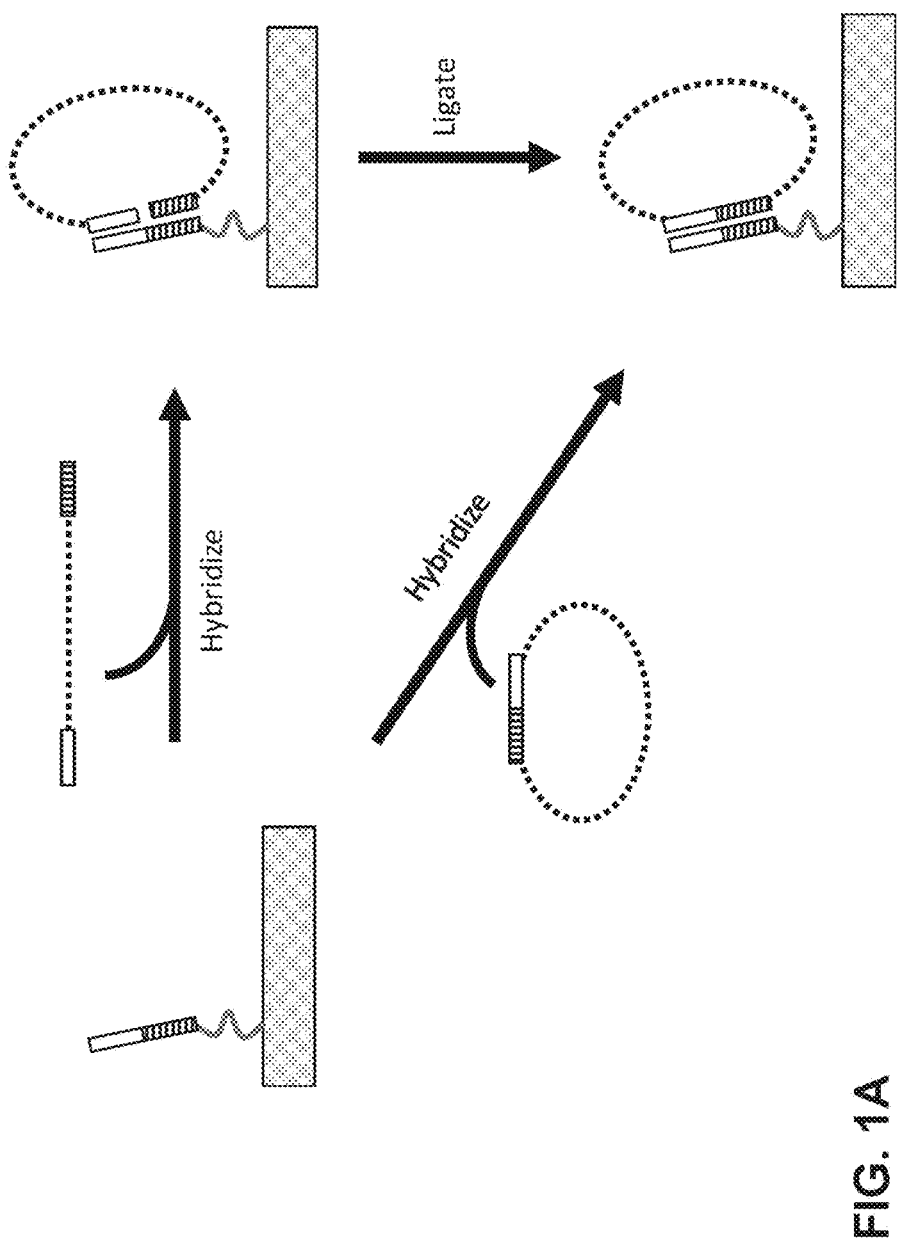
FIG. 1A shows a diagrammatic representation of methods for producing a circular template nucleic acid hybridized to an immobilized nucleic acid primer (e.g., a capture primer).
Figure 1B:
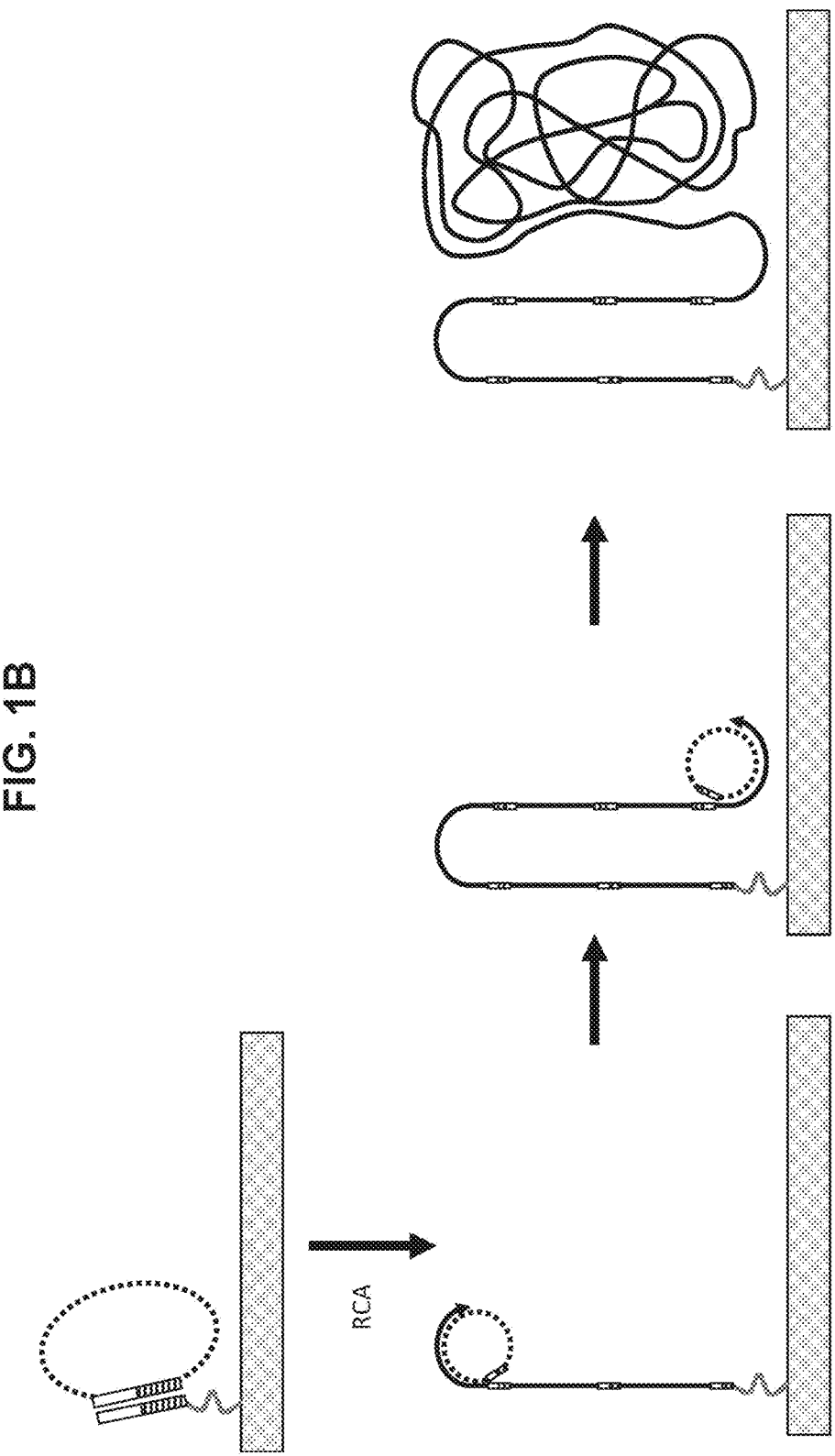
FIG. 1B shows a diagrammatic representation of extending an immobilized primer along a circular template nucleic acid via rolling circle amplification to produce a cluster having an immobilized, single concatemer strand.

The guide oligo is then subjected to an extension reaction, so as to have added at its 3' end multiple monomer units of the originally linear nucleic acid, via rolling circular amplification. The result is a concatemer of multimers of the original linear nucleic acid being tethered to the surface via the guide oligo, as seen in FIG. 1B. This reaction may be terminated via heat inactivation of the polymerase or though washing, alone or in combination with chemical inactivation.

Methods and compositions herein involve one or more of the steps herein, such that practice of the disclosure herein may comprise some or all of the steps disclosed herein. Some methods effectively 'start' midway through the process as described herein. Thus, for example, at FIG. 1D, one sees a process that starts with a circularized library constituent having adjacent first and second adapter regions rather than a linear nucleic acid having a 5' and 3' adapter. One sees that the process for subsequent steps is nonetheless quite similar.

Figure 1C:
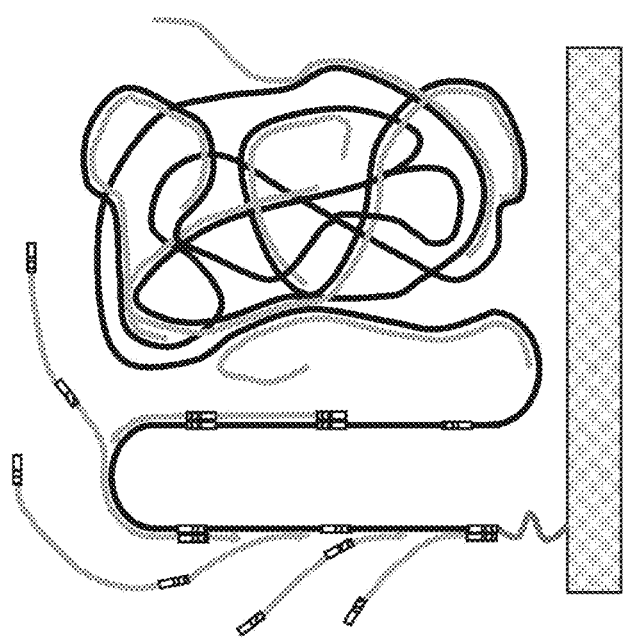
FIG. 1C shows a diagrammatic representation of extending a plurality of primers (e.g., amplification primers) along an immobilized sense strand of a concatemer to produce a cluster having the immobilized sense strand hybridized to a plurality of antisense strands of the concatemer.
Figure 1C:
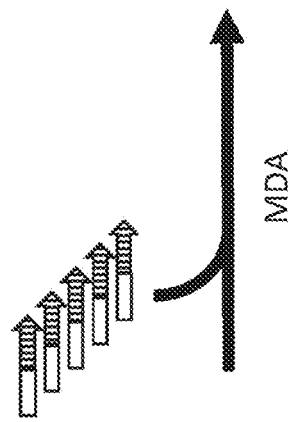
Figure 1C:
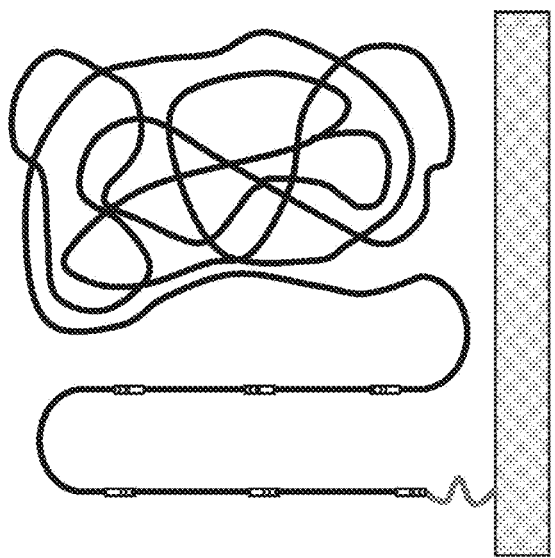

Multiple Displacement Amplification oligos are contacted to the concatemer and extended, so as to form a series of distinct extension products that are annealed to the concatemeric strand at their 3' ends, as seen in FIG. 1C. In some embodiments, these extension reactions are also sequencing reactions, as described with reference to FIGS. 3B-3D. Alternately, these extension reactions are in some cases performed without sequencing, so as to preserve integrity of the template and extension strands by avoiding the nucleic acid damage that often occurs during the imaging process or other steps of a sequencing reaction. The oligos are provided in solution, or alternately are tethered to a surface. In cases where the oligos are tethered to the surface, the result is a surface having tethered thereto a plurality of concatemeric nucleic acid molecules, where the concatemeric nucleic acid molecules comprise multiple monomeric units, and wherein the nucleic acid molecules are locally, partially hybridized to form locally double-stranded segments adjacent to displaced single-stranded segments. For example, one sense strands can locally, partially hybridize to multiple antisense strands. In some embodiments, the antisense strands are sequenced when locally, partially hybridized to sense strands, and/or the sense strands are sequenced when locally, partially hybridized to antisense strands. Alternatively or additionally, the antisense strands and the sense strands are separated by, for example, heat denaturation, such that the antisense strands and the sense strands are not locally, partially hybridized when sequencing the antisense strands (or sense strands).

The extension reactions primed by the MDA oligos are optionally terminated, for example by introduction of a 3' blocked nucleotide. See FIG. 2A. In some cases the 3' nucleotide is bound to a moiety of a size or shape sufficient to inhibit ternary complex formation, such that a polymerase will not bind to the 3' end of a strand terminated hereby, even though it is bound to a template strand. This has the benefit of reducing background signal when sequencing by binding is used in subsequent sequencing reactions, as described elsewhere herein.

The exposed, single-stranded segments of the series of distinct extension products that are annealed to the concatemeric strand at their 3' ends are then used as templates for sequencing reactions, primed optionally by primers that anneal to or are colinear with a conserved region of the concatemer, for example the regions originally used to circularize the linear nucleic acid library constituent. See again FIG. 2A.

The sequencing reactions are optionally terminated, using terminator moieties that are identical, similar, or distinct from those used above. Again, in some cases it is beneficial to terminate using moieties that block formation of ternary complexes, so that they do not generate background signal in sequencing by binding reactions performed subsequently. In alternate cases, these molecules are removed or degraded prior to subsequent sequencing of the complementary strand.

Often, these sequencing reactions are not allowed to continue extending after sequencing is complete, such that a full monomer of the concatemer nucleic acid is not formed pursuant to the sequencing. Rather, they are terminated, either through incorporation of blocking moieties, or through removal of the sequencing reagents, or both. Alternately, some sequencing reactions are allowed to extend so as to from copies of the full monomer of which they sequenced a portion.

The second strand of a paired read is sequenced through any of a number of approaches. For example, in some cases a primer is annealed to a monomer unit at the 3' end of the single-stranded concatemer that is not annealed to an MDA oligo or MDA oligo extension product, as shown in FIG. 2B. Alternately or in combination, the series of distinct extension products that are annealed to the concatemeric strand at their 3' ends are removed or degraded, often along with the sequencing reaction products to which they are annealed, thereby exposing the single stranded concatemer template. Removal can be affected by melting the molecule, such that the molecule is no longer held together by its base pairing and the partially double stranded nucleic acid products fall off of the concatemeric template. Alternately, the MDA primed extension products may incorporate cleavable or cleavage-guiding moieties, such as dUTP incorporated as uracil bases, that may be used to tag the extension products for degradation. The cleavage-guiding moieties facilitate the degradation of the partially double-stranded nucleic acid products, such that they are degraded in some cases while still attached to the single stranded concatemer, and while the reverse complementary sequencing primers remain hybridized.

Sequencing primers, such as the MDA primers used previously or other primers annealing in monomeric units of the concatemers, are then used to prime a series of sequencing reactions. These sequencing reactions run on the opposite strand and in the opposite direction relative to the previous round of sequencing reactions, and produce reads which can be paired with the previous round of sequencing reads to generate sequencing data for two distinct regions of a template, such as the two ends of the original linear template used to generate the concatemer molecule.

These approaches convey a number of benefits relative to approaches in the art or in use in sequencing. Firstly, the sequencing templates are often not more than 2, 3 or 4 copy steps removed from the from the linear or circular nucleic acid such as a library constituent depicted in FIG. 1A. That is, in some cases of the technology herein, no library constituent is subjected to more than 2, 3 or 4 rounds of copying pursuant to colony formation and sequencing.

Copying may occur prior to colony formation, and many more than 2, 3 or 4 copies are generated, but none of the sequenced products of a colony are more than 2, 3 or 4 copying reactions removed from the starting library material in some cases. Alternately, in some cases the library constituents are subjected to more than 2, 3 or 4 copying cycles, such as 5, 6, 7, 8, 9, 10 or more than 10 copying cycles. Accordingly, errors introduced through amplification-heavy processes such as bridge amplification, which rely upon using polymerase products as templates from subsequent amplification, are not introduced into the paired read approaches disclosed herein. Accordingly, reactions are likely to exhibit substantially higher accuracy than those relying upon other amplification approaches.

The starting linear nucleic acid molecule such as a library constituent is relatively unconstrained by length. Whereas bridge amplification is less efficient for library constituents that are too small or too large relative to the positioning of oligos on a cluster or whose copying takes a long time or has risk of polymerases falling off and not completing extension, the approaches herein are neutral as to starting nucleic acid length, and can accommodate library constituents having lengths of less than 50, 45, 40, 35, 30, 25, 20 or less than 20, or alternately at least 300, 400, 500, 600, 700, 800, 900, 1000, 2000, 3000, or greater than 3000 bases.

Some of the approaches herein do not require thermocycling, and can be performed in an environment having some steps or all steps that can be isothermally completed. Some of the approaches herein do not require thermocycling other than heat inactivation of enzyme of RCA and/or MDA reactions, and can be performed in an environment having some steps or all steps that can be isothermally completed. Alternatively, inactivation is accomplished by chemical deactivation or removal, such as by washing. That is, rolling circle amplification, MDA primer annealing, sequencing and degradation, such as uracil-incorporation mediated degradation, are in some cases all performed at a single temperature, or particular sub-steps of the process are all performed at a single temperature, such that thermocycling is not relied upon to the extent that it is in bridge amplification-mediated sequencing reactions. For example, in some cases concatemer formation occurs isothermally, MDA primed second stand synthesis occurs isothermally, and sequencing of the second strand and of the first strand occurs isothermally, wherein the first, second and third of these portions of the disclosure may occur at the same temperature or at different temperatures relative to one another.

Approaches herein in some cases do not rely upon a sequencing reaction product to serve as a template for a second strand sequencing reaction. That is, in some cases all templates are generated prior to any sequencing reactions being undertaken. This separation of template formation from sequencing facilitates isothermal reactions and reduces thermal stress on sequencing devices, because all template formation may occur at a single temperature, optionally under isothermal conditions, while all sequencing occurs subsequently and at temperature, such as an isothermal temperature, suitable for sequencing. Separating template generation from sequencing allows a reduction in temperature changes, and allows each group of steps to be performed under its own temperature regime.

Accordingly, the methods and compositions herein yield paired sequence data, wherein neither sequence of the paired sequence data results from more than four rounds of copying from a library template. That is, in some cases of the technology herein, no library constituent is subjected to more than 2, 3 or 4 rounds of copying pursuant to colony formation and sequencing. Copying may occur prior to colony formation, and many more than 2, 3 or 4 copies are generated, but none of the sequenced products of a colony are more than 2, 3 or 4 copying reactions removed from the starting library material in some cases. Alternately, in some cases the library constituents are subjected to more than 2, 3 or 4 copying cycles, such as 5, 6, 7, 8, 9, 10 or more than 10 copying cycles. The number of copying cycles can be, be about, be at least about, be at most, or be at most about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, or a number or a range between any two of these values. The paired sequencing reads are in some cases generated without thermocycling during sequencing, or without thermocycling during amplification, or are generated isothermally. Some of the approaches herein do not require thermocycling other than enzyme inactivation by heat and can be performed in an environment having some steps or all steps that can be isothermally completed. Alternatively, enzyme inactivation is accomplished by chemical deactivation or washing. The paired sequence reads are generated in many cases from templates that were not generated from prior templates that were subjected to sequencing reaction conditions. That is, all templates are generated prior to any sequencing reactions, resulting in cleaner templates and a more efficient sequencing workflow. Alternatively, in some cases strands are sequenced prior to synthesis of their reverse complements that will be sequenced subsequently (See FIGS. 3A-3F for an example).

The methods set forth herein, can be readily multiplexed such that paired end sequence data can be acquired from a plurality of target nucleic acids in parallel. For example, a plurality of target sequences can be distributed over the sites of an array of nucleic acids. Each site can contain a cluster having both the sense strand of a particular target nucleic acid and the antisense strand of the target, and both strands can be present in each of the clusters when sequencing is carried out. Those skilled in the art will recognize that the methods can also be configured to acquire paired end sequence data from a plurality of target nucleic acids by serial processing of target nucleic acids from the plurality of target nucleic acids.

The present disclosure provides methods for making a nucleic acid cluster having both sense and antisense strands of a target nucleic acid. In particular configurations, clusters are formed by a combination of rolling circle amplification (RCA) of a circular template nucleic acid to form a sense strand of a concatemer and multiple displacement amplification (MDA) to form one or more antisense strands of the concatemer. The sense strand can be attached to a solid support, for example, by virtue of having been produced by extension of a solid support-immobilized primer during the RCA reaction. The antisense strand can be attached to the solid support, for example, by virtue of having been produced by extension of a solid support-immobilized primer during the MDA reaction. The RCA and MDA reactions can be carried out simultaneously (e.g. by performing amplification in the presence of primers for both the sense and antisense strands). FIG. 1D illustrates a non-limiting exemplary method of carrying out the RCA and MDA reactions simultaneously. Alternatively, the RCA and MDA reactions can be carried out sequentially (e.g. by performing RCA to produce the sense strand in the absence of the primer for the antisense strand and then delivering the primer for the antisense strand to produce the antisense strand by MDA). FIGS. 1A-1C illustrate a non-limiting exemplary method of carrying out the RCA and MDA reactions sequentially.

Surprisingly, the antisense strands need not be produced by an immobilized primer in order to be retained in a cluster for dual strand sequencing. Rather, antisense strands produced by a combination of immobilized-primer RCA and soluble-primer MDA can be retained in a cluster due to non-covalent interactions of the antisense strand with the sense strand or with other immobilized moieties of the cluster.

For some embodiments that employ sequencing of one strand in a cluster that also contains other strands, it may be useful to modify 3' ends in the other strands prior to the sequencing. The methods set forth herein can employ a primer modification process that suits a particular sequencing method being employed. For example, undesirable 3' ends can be modified to incorporate a 3' blocking moiety. The blocking moiety can be useful for preventing unwanted background signal. Unwanted background signal can arise from, for example, Sequencing By Binding™ (SBB™) or sequencing by synthesis (SBS) reactions. Unwanted background result from extension of the undesirable 3' ends during a SBS process. Particularly useful blocking moieties are irreversible (e.g. dideoxynucleotides) or are inert to removal by reagents used in the SBS process (e.g. the blocking moiety is a reversible terminator that is orthogonal to reversible terminators used in the SBS process). Alternately or in combination, 3' ends in other strands can be modified to incorporate a 3' capping moiety. The capping moiety can be useful for preventing unwanted background signal that would result from formation of stabilized ternary complexes at 3' ends during a SBB™ process. Generally, the capping moiety will be irreversible or at least inert to removal by reagents used in the SBB™ process. If desired, a capping moiety can be reversible, for example, capable of removal by denaturation, linker cleavage or the like.

Terms used herein will be understood to take on their ordinary meaning in the relevant art unless specified otherwise. Several terms used herein and their meanings are set forth below.

As used herein, the term "about" a number or range refers to a range spanning +/−10% of that number, or +/−10% of the limit of the previously stated range.

As used herein, the term "array" refers to a population of molecules that is attached to one or more solid support such that the molecules can be distinguished from each other. An array can include different molecules that are each located at different addressable sites on a solid support. An array can include separate solid supports each functioning as a site that bears a different molecule, wherein the different molecules can be identified according to the locations of the solid supports on a surface to which the solid supports are attached, or according to the locations of the solid supports in a liquid such as a fluid stream. The molecules of the array can be, for example, nucleotides, nucleic acid primers, nucleic acid templates or nucleic acid enzymes such as polymerases, ligases, exonucleases or combinations thereof.

As used herein, the phrase "at least one of" A, B, and C (in any order), refers to a set that can include A, or can include A and B, or can include A, B, and C, alone or in combination with other unlisted elements.

As used herein, the term "attached" refers to the state of two things being joined, fastened, adhered, connected or bound to each other. For example, a reaction component, such as a primed template nucleic acid or a polymerase, can be attached to a solid phase component by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "blocking moiety," when used in reference to a nucleotide, means a part of the nucleotide that inhibits or prevents the 3' oxygen of the nucleotide from forming a covalent linkage to a next correct nucleotide during a nucleic acid polymerization reaction. The blocking moiety of a "reversibly terminated" nucleotide can be removed from the nucleotide analog, or otherwise modified, to allow the 3'-oxygen of the nucleotide to covalently link to a next correct nucleotide. Such a blocking moiety is referred to herein as a "reversible terminator moiety." Exemplary reversible terminator moieties are set forth in U.S. Pat Nos. 7,427,673; 7,414,116; 7,057,026; 7,544,794 or 8,034,923; or PCT publications WO 91/06678 or WO 07/123744, each of which is incorporated herein by reference. A nucleotide that has a blocking moiety or reversible terminator moiety can be at the 3' end of a nucleic acid, such as a primer, or the nucleotide can be a monomer that is not covalently attached to a nucleic acid. A blocking moiety need not hinder or preclude ternary complex formation at the 3' end of a nucleic acid to which the blocking moiety is attached. A particularly useful blocking moiety will be present at the 3' end of a nucleic acid that participates in formation of a ternary complex.

As used herein, the term "capping moiety," when used in reference to a nucleic acid, means a moiety that when present in a nucleic acid hinders or precludes the 3' end of the nucleic acid from binding to a polymerase and next correct nucleotide to form a ternary complex. Moieties that create a steric block to ternary complex formation are particularly useful and include, for example, a polymerization or ligation product that extends a primer to the end of a template to which the primer is hybridized. Another example of a steric block is a mismatched nucleotide. A capping moiety can have a positive or negative charge that hinders or prevents ternary complex formation. A capping moiety can include a ligand that binds a receptor to hinder or prevent ternary complex formation such as a biotin (or analog thereof) that binds to streptavidin (or an analog thereof), an epitope that binds to an antibody (or functional fragment thereof), a carbohydrate that binds to a lectin, or the like. Thus, a ternary complex inhibitor can be a ligand-receptor complex that inhibits ternary complex formation. Further examples of moieties that can be used in ternary complex inhibitors include base modifications and nucleotide analogs described in US Pat. App. Pub. No. 2020/0032322 A1 or Turcatti et al. *Nucl. Acids. Res.* 36(4) e25 (2008), each of which is incorporated herein by reference.

As used herein, the term "circular," when used in reference to a nucleic acid strand, means that the strand has no terminus (that is, the strand lacks a 3' end and a 5' end). Accordingly, the 3' oxygen and the 5' phosphate moieties of every nucleotide monomer in a circular strand is covalently attached to an adjacent nucleotide monomer in the strand. A circular DNA strand can serve as a template for producing a concatemeric amplicon via rolling circle amplification (RCA), wherein each sequence unit of the concatemeric amplicon is the reverse complement of the circular nucleic acid strand. A circular nucleic acid can be double stranded. One or both strands in a double stranded nucleic acid can lack a 3' end and a 5' end. One strand in a double stranded nucleic acid can have a gap (absence of at least one nucleotide monomer relative to the other strand) or nick (absence of a phosphodiester bond between two nucleotide monomers), so long as the other strand is circular.

As used herein, the term "cluster," when used in reference to nucleic acids, refers to a population of nucleic acids that is attached to a solid support, for example, at a site in an array of sites on the solid support. The term "clonal population" refers to a population of nucleic acids that is homogeneous with respect to a particular nucleic acid sequence. The homogenous sequence is typically at least 10 nucleotides long, but can be even longer including for example, at least 50, 100, 500, 1000 or 2500 nucleotides long. A clonal population can be derived from a single template nucleic acid. A clonal population can include at least 2, 10, 100, 1000 or more copies of a particular nucleic acid sequence. The copies can be present in a single nucleic acid molecule, for example, as a concatemer, or the copies can be present on separate nucleic acid molecules. Typically, all the nucleic acids in a cluster will have the same nucleotide sequence. It will be understood that a negligible number of contaminant nucleic acids or mutations (e.g. due to amplification artifacts) can occur in a cluster without departing from apparent clonality. A cluster can be at least 80%, 90%, 95% or 99% clonal. Optionally, a cluster can be 100% clonal.

As used herein, the term "common sequence" means a sequence of nucleotides that is the same for two or more nucleic acid molecules. The sequence that is common to two or more nucleic acids can include all or part of the nucleic acids that are being compared. The common sequence can have a length of at least 5, 10, 25, 50, 100, 250, 500, 1000 or more nucleotides. Alternatively or additionally, the length can be at most 1000, 500, 250, 100, 50, 25, 10, or 5 nucleotides. A population of nucleic acid molecules can include individual molecules that have a region of common sequence between the individuals (e.g. a 'universal primer' or "universal primer binding site") and a region of variable sequence that differs from one individual to another (e.g. a 'target region').

As used herein, the term "concatemer," when used in reference to a nucleic acid molecule, means a continuous nucleic acid molecule that contains multiple copies of a common sequence linked in series. Similarly, the term "concatemer," when used in reference to a nucleotide sequence, means a continuous nucleotide sequence that contains multiple copies of a common sequence in series. Each copy of the sequence can be referred to as a "sequence unit" of the concatemer. A sequence unit can have a length of at least 10 bases, 50 bases, 100 bases, 250 bases, 500 bases or more. A concatemer can include at least 2, 5, 10, 50, 100 or more sequence units. A sequence unit can include subregions having any of a variety of functions such as a primer binding region, target sequence region, tag region, unique molecular identifier (UMI), or the like.

The term "comprising" is intended herein to be open-ended, including not only the recited elements, but further encompassing any additional elements.

As used herein, the term "cycle," when used in reference to a sequencing procedure, refers to the portion of a sequencing run that is repeated to indicate the presence of a nucleotide. Typically, a cycle includes several steps such as steps for delivery of reagents, washing away unreacted reagents and detecting signals indicative of changes occurring in response to added reagents.

As used herein, the term "deblock" means to remove or modify a reversible terminator moiety of a nucleotide to render the nucleotide extendable. For example, the nucleotide can be present at the 3' end of a primer such that deblocking renders the primer extendable. Exemplary deblocking reagents and methods are set forth in U.S. Pat Nos. 7,427,673; 7,414,116; 7,057,026; 7,544,794 or 8,034,923; or PCT publications WO 91/06678 or WO 07/123744, each of which is incorporated herein by reference.

As used herein, the term "exogenous," when used in reference to a moiety of a molecule, means a chemical moiety that is not present in a natural analog of the molecule. For example, an exogenous label of a nucleotide is a label that is not present on a naturally occurring nucleotide. Similarly, an exogenous label that is present on a polymerase is not found on the polymerase in its native milieu.

As used herein, the term "extension," when used in reference to a nucleic acid, means a process of adding at least one nucleotide to the 3' end of the nucleic acid. The term "polymerase extension," when used in reference to a nucleic acid, refers to a polymerase catalyzed process of adding at least one nucleotide to the 3' end of the nucleic acid. A nucleotide or oligonucleotide that is added to a nucleic acid by extension is said to be incorporated into the nucleic acid. Accordingly, the term "incorporating" can be used to refer to the process of joining a nucleotide or oligonucleotide to the 3' end of a nucleic acid by formation of a phosphodiester bond.

As used herein, the term "extendable," when used in reference to a nucleotide, means that the nucleotide has an oxygen or hydroxyl moiety at the 3' position, and is capable of forming a covalent linkage to a next correct nucleotide. An extendable nucleotide can be at the 3' position of a polymeric nucleic acid or it can be a monomeric nucleotide. A nucleotide that is extendable will lack blocking moieties such as reversible terminator moieties.

As used herein, the term "immobilized," when used in reference to a molecule, refers to direct or indirect, covalent or non-covalent attachment of the molecule to a solid support. In some configurations, covalent attachment may be preferred, but generally all that is required is that the molecules (e.g. nucleic acids) remain immobilized or attached to the support under the conditions in which it is intended to use the support, for example, when sequencing nucleic acids that are immobilized to a site of an array or to another solid support.

As used herein, the term "label" refers to a molecule, or moiety thereof, that provides a detectable characteristic. The detectable characteristic can be, for example, an optical signal such as absorbance of radiation, fluorescence emission, luminescence emission, fluorescence lifetime, fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like.

As used herein, the term "next correct nucleotide" refers to the nucleotide or nucleotide type that will bind and/or incorporate at the 3' end of a primer to complement a base in a template strand to which the primer is hybridized. The base in the template strand is referred to as the "next base" and is immediately 5' of the base in the template that is hybridized to the 3' end of the primer. The next correct nucleotide can be referred to as the "cognate" of the next base and vice versa. Cognate nucleotides that interact with each other in a ternary complex or in a double stranded nucleic acid are said to "pair" with each other. A nucleotide having a base that is not complementary to the next template base is referred to as an "incorrect", "mismatch" or "non-cognate" nucleotide.

As used herein, the term "non-catalytic metal ion" refers to a metal ion that, when in the presence of a polymerase enzyme, does not facilitate phosphodiester bond formation needed for chemical incorporation of a nucleotide into a primer. A non-catalytic metal ion may interact with a polymerase, for example, via competitive binding compared to catalytic metal ions. Accordingly, a non-catalytic metal ion can act as an inhibitory metal ion. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein, the term "nucleotide" can be used to refer to a native nucleotide or analog thereof. Examples include, but are not limited to, nucleoside monophosphate, nucleoside diphosphate, and nucleoside triphosphates (NTPs) such as ribonucleoside triphosphates (rNTPs), deoxyribonucleoside triphosphates (dNTPs), or non-natural analogs thereof such as dideoxyribonucleoside triphosphates (ddNTPs) or reversibly terminated nucleoside triphosphates (rtNTPs).

As used herein, the term "polymerase" can be used to refer to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' oxygen group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation. A polymerase can have strand displacement activity, such as Phi29. A polymerase can lack strand displacement activity. A polymerase can have 5'→3' exonuclease activity. A polymerase can lack 5'→3' exonuclease activity.

As used herein, the term "primer" refers to a nucleic acid having a sequence that binds to a nucleic acid at or near a template sequence. Generally, the primer binds in a configuration that allows replication of the template, for example, via polymerase extension of the primer. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence. A primer can include, or can be, DNA, RNA or analogs thereof. A primer can have an extendible 3' end, a 3' end that is blocked from primer extension or a 3' end that is capped to hinder or preclude ternary complex formation. In some embodiments, a primer can include modifications of nucleotides not at the 5' end and the 3' end. Alternatively or additionally, a primer can include a modified nucleotide at the 5' end.

As used herein, the term "primer-template nucleic acid hybrid" or "primer-template hybrid" refers to a nucleic acid having a double stranded region such that one of the strands is a primer and the other strand is a template. The two strands can be parts of a contiguous nucleic acid molecule (e.g. a hairpin structure) or the two strands can be separable molecules that are not covalently attached to each other.

The terms "sense" and "antisense" are use herein to distinguish members of a pair of complementary nucleic acid molecules or sequences. The terms are intended as context specific identifiers. The terms are interchangeable in accordance with their use in the art of molecular biology. As such, a strand that is identified as a "sense strand" in one context can be referred to as an "antisense" strand in a second context. This is independent of how similar or different the first context is compared to the second context.

As used herein, the term "site," when used in reference to an array, means a location in the array where a particular molecule is present. A site can contain only a single molecule or it can contain a population of several molecules of the same species (an ensemble of the molecules). Alternatively, a site can include a population of molecules that are different species (e.g. a population of ternary complexes having different template sequences). Sites of an array are typically discrete. The discrete sites can be contiguous or they can have interstitial spaces between each other. An array useful herein can have, for example, sites that are separated by less than 100 microns, 50 microns, 10 microns, 5 microns, 1 micron, or 0.5 micron. Alternatively or additionally, an array can have sites that are separated by greater than 0.5 micron, 1 micron, 5 microns, 10 microns, 50 microns or 100 microns. The sites can each have an area of less than 1 square millimeter, 500 square microns, 100 square microns, 25 square microns, 1 square micron or less. A site may also be referred to as a "feature" of an array.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, the term "template" means a nucleic acid, or portion thereof, having a sequence of nucleotide bases that act as a guide for producing a complementary copy of the sequence. A template can be copied via extension of a primer that is hybridized at or adjacent to the template. Extension can be mediated by a polymerase or ligase. A template can include, or can be, DNA, RNA or analogs thereof.

As used herein, the term "ternary complex" refers to an intermolecular association between a polymerase, a double stranded nucleic acid and a nucleotide. Typically, the polymerase facilitates interaction between a next correct nucleotide and a template strand of the primed nucleic acid. A next correct nucleotide can interact with the template strand via Watson-Crick hydrogen bonding. The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

The embodiments set forth below and recited in the claims can be understood in view of the above definitions.

The present disclosure provides a method for determining sequences from sense and antisense strands of a nucleic acid. The sense and antisense strands can be, for example, first and second strands respectively. The method can include steps of (a) providing a nucleic acid cluster attached to a solid support, wherein the nucleic acid cluster includes a sense strand of a concatemer and an antisense strand of the concatemer, wherein the concatemer includes multiple copies of a sequence unit linked in series, wherein the sequence unit includes a target sequence and a primer binding site; (b) hybridizing a primer to the primer binding site in a sequence unit of the antisense strand in the cluster; (c) extending the primer along the antisense strand to determine the sequence from at least a portion of the target sequence in the antisense strand; (d) hybridizing a second primer to the primer binding site in a sequence unit of the sense strand; and (e) extending the second primer along the sense strand to determine the sequence from at least a portion of the target sequence in the sense strand.

Nucleic acids that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used in a method or composition of the present disclosure. For example, a nucleic acid analog can be used as a template for an amplification or sequencing process set forth herein.

Nucleic acids used herein, for example, as a template to produce a nucleic acid cluster or as a target for sequencing, can be derived from a biological source, synthetic source or amplification product. Primers used herein can include, or can be, DNA, RNA or analogs thereof.

A nucleic acid template containing a target sequence subject to the sequencing methods of the present disclosure can be derived or generated from a sample. The sample include one or more organisms. The nucleic acid template may be obtained or derived from the sample without performing polymerase chain reaction. The nucleic acid template may be obtained or derived from the sample by performing a few cycles of polymerase chain reaction, such as at most one cycle, two cycles, three cycles, four cycles, five cycles, six cycles, seven cycles, eight cycles, nine cycles, or ten cycles or more than ten cycles.

Different lengths of nucleic acid templates (or target sequences) are contemplated herein. A nucleic acid template can be, be about, be at least, be at least about, be at most, be at most about, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length.

Exemplary organisms from which nucleic acids can be derived include, for example, a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *dictyostelium discoideum*; a fungi such as *pneumocystis carinii, Takifugu rubripes*, yeast, *Saccharamoyces cerevisiae* or *Schizosaccharomyces pombe*; or a *plasmodium falciparum*. Nucleic acids can also be derived from a prokaryote such as a bacterium, *Escherichia coli, Staphylococci* or *Mycoplasma pneumoniae*; an archaea; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

A nucleic acid can be obtained from a preparative method such as genome, transcriptome or other nucleic acid isolation, genome fragmentation, gene cloning and/or amplification. One or more nucleic acids can be obtained from an amplification technique such as polymerase chain reaction (PCR), emulsion PCR, random prime amplification, rolling circle amplification (RCA), multiple displacement amplification (MDA) or the like. RCA and MDA can be particularly useful for producing concatemeric products. Exemplary methods for isolating, amplifying and fragmenting nucleic acids to produce templates for analysis on an array are set forth in U.S. Pat. Nos. 6,355,431 or 9,045,796, each of which is incorporated herein by reference. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

A nucleic acid cluster can contain one or more strands of a nucleic acid concatemer. For example, a cluster can contain only a single strand of the nucleic acid concatemer. A single concatemer strand can be produced by an RCA reaction, for example as diagramed in FIG. 1B. Alternatively, a nucleic acid cluster can contain a first strand (e.g., a sense strand) that is a concatemer along with one or more second strands (e.g., an antisense strand) that are complementary to the first strand. The one or more second strands can be produced, for example, by multiple displacement amplification (MDA) performed on a concatemeric template. See for example, the double stranded clusters produced by the method diagramed in FIG. 1C or FIG. 1D. For ease of reference one of the two complementary strands can be referred to as the 'sense' strand and the complement of the sense strand can be referred to as the 'antisense' strand in accordance with conventions used in the art of molecular biology.

A concatemer strand in a cluster can include multiple copies of a sequence unit linked in series. For example, the concatemer strand can include at least 2, 10, 25, 100 or more sequence units. The number of sequence units in a concatemer strand can be, for example, at most 100, 25, 10 or 2 sequence units. The number of sequence units in a concatemer that is produced by RCA will be a function of the number of times a polymerase completes a lap around a circular template during replication. The content of each sequence unit that is produced by RCA will be the reverse complement of the content of the circular template that was replicated. For example, as shown in FIG. 1B, the circular template includes two adapter regions (indicated by an open rectangle and cross hatched rectangle) and a target region (indicated by the dotted line). The adapter regions can have any of a variety of functions including, but not limited to, providing a binding site that complements a capture probe (e.g. a capture probe attached to a solid support), providing a primer binding site for replicating the circular template, providing a primer binding site for replicating a complement of the circular template, providing a tag that is associated with the target region (e.g. a tag indicating the source of the target region or a tag used for identifying errors introduced during amplification of the target region etc.). The adapter regions or portions thereof can be common to a population of circular templates or to a population of concatemers. Whether or not the adapter regions have common sequences, the target regions in the population of circular templates or in the population of concatemers can have different sequences. Thus, when comparing sequence units between two or more concatemers, or between two or more circular templates, the sequence units can have common sequence regions (e.g. universal primer binding sites or universal capture probe binding sites) and/or the sequence units can have regions of differing sequence (e.g. different target sequences).

The length of a sequence unit in a concatemer or the length of a circular template can be selected to suit a particular application of the methods set forth herein. For example, the length can be at least about 50, 100, 250, 500, 1000, $1 \times 10^4$, $1 \times 10^5$ or more nucleotides. Alternatively or additionally, the length can be no more than $1 \times 10^5$, $1 \times 10^4$, 1000, 500, 250, 100, or 50 nucleotides. It will be understood that the above length ranges can apply to the target region of a sequence unit or circular template, excluding adapter sequences (e.g. common or universal adapter sequences) that may also be present in the sequence unit. For example, the length ranges can delineate sizes of genome fragments or other nucleic acid fragments that are used to produce a cluster or that are otherwise present in a cluster.

A cluster can include one or more concatemeric strands. In some configurations, a cluster contains no more than one concatemeric strand. Alternatively, a cluster can include a plurality of concatemer strands, for example, including at least 2, 4, 10, 50, 100 or more sense strands of a concatemer. Alternatively or additionally, the number of concatemer strands in a cluster can be, for example, including at most 100, 50, 10, 4, 2 or 1 sense strands of the concatemer. In some embodiments, the number of concatemer strands can be, be about, be at least, be at least about, be at most, or be at most about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, or a number or a range between any two of these values. The concatemer strands in a particular cluster can have the same target sequence, for example, being sense strands of the same concatemer. Alternatively, a cluster can have a plurality of different concatemer strands, such a cluster being non-clonal.

A cluster that contains at least one sense strand of a concatemer can further contain at least one antisense strand of the concatemer. For example, a cluster that contains one or more sense strands of a concatemer can further contain a plurality of antisense strands. The plurality of antisense strands can include at least 2, 4, 10, 50, 100 or more antisense strands of a particular concatemer. Alternatively or additionally, the number of antisense strands in a cluster can be, for example, at most 100, 50, 10, 4, 2 or 1 antisense strands of a particular concatemer. In some embodiments, the number of antisense strands can be, be about, be at least, be at least about, be at most, or be at most about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, or a number or a range between any two of these values. In particular configurations, a cluster can contain a single sense concatemer strand (no more than one sense strand) and a single antisense concatemer strand (no more than one antisense strand). Alternatively, a cluster can contain at least one sense strand of a concatemer and multiple antisense strands of the concatemer. The number of antisense strands in a cluster can outnumber the sense strands in the cluster. Alternatively, the number of sense strands in a cluster can outnumber the antisense strands in the cluster. Note that the antisense strand of the concatemer need not be the same length as the sense strand. For example, the antisense strand can have more sequence units than the sense strand, or the antisense strand can have fewer sequence units than the sense strand. The number of sequence units in an antisense strand can fall in a range set forth herein for sense strands of a concatemer. An antisense strand of a concatemer need not have more than one sequence unit. Indeed, an antisense strand need not have a complete sequence unit.

A cluster that contains at least one sense strand of a concatemer can further contain at least one antisense strand of the concatemer hybridized to the sense strand via Watson-Crick base pairing. For example, the sense strand of a particular concatemer can hybridize to at least 2, 4, 10, 50, 100 or more antisense strands of the particular concatemer. Alternatively or additionally, the sense strand of a particular concatemer can be hybridize to, for example, at most 100, 50, 10, 4, 2 or 1 antisense strands of the particular concatemer.

A nucleic acid cluster can be attached to a solid support. The solid support can be made from any of a variety of materials used for analytical biochemistry. Suitable materials may include, for example, glass, polymeric materials, silicon, quartz (fused silica), borofloat glass, silica, silica-based materials, carbon, metals, an optical fiber or bundle of optical fibers, sapphire, or plastic materials. The material can be selected based on properties desired for a particular use. For example, materials that are transparent to a desired wavelength of radiation are useful for analytical techniques that will utilize radiation of that wavelength. Conversely, it may be desirable to select a material that does not pass radiation of a certain wavelength (e.g. being opaque, absorptive or reflective). Wavelength regions that may be pass or not pass through a particular material include, for example, UV, VIS (e.g. red, yellow, green, or blue) or IR. Other properties of a material that can be exploited are inertness or reactivity to certain reagents used in a downstream process, such as those set forth herein, or ease of manipulation, or low cost of manufacture.

A particularly useful solid support is a particle such as a bead or microsphere. Populations of beads can be used for attachment of populations of nucleic acids. In some embodiments, it may be useful to use a configuration whereby each bead has a single target sequence. An individual bead can have a single nucleic acid molecule with the target sequence, or alternatively, an individual bead can have multiple nucleic acid molecules each of the molecules having the target sequence. In some configurations, a bead can be attached to a nucleic acid concatemer in which multiple copies of a target sequence are present in a single nucleic acid molecule. The beads in a population of beads can have different target sequences from each other. The beads in a population of beads can have common nucleic acid sequences when compared to each other. For example, a population of beads can be attached to universal primers such that the same primer sequence is present on a plurality of beads in the population.

The composition of a bead can vary, depending for example, on the format, chemistry and/or method of attachment to be used. Exemplary bead compositions include solid supports, optionally including chemical functionalities that are used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as other materials set forth in "Microsphere Detection Guide" from Bangs Laboratories, Fishers Ind., which is incorporated herein by reference.

The geometry of a particle, such as a bead or microsphere, also can correspond to a wide variety of different forms and shapes. For example, a particle can be symmetrically shaped (e.g. spherical or cylindrical) or irregularly shaped (e.g. controlled pore glass). In addition, particles can be porous, thus increasing the surface area available for capture of ternary complexes or components thereof. Exemplary sizes for beads used herein can range from nanometers to millimeters or from about 10 nm to about 1 mm.

In particular embodiments, beads can be arrayed or otherwise spatially distinguished. Exemplary bead-based arrays that can be used include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

As will be recognized from the above bead array embodiments, a method of the present disclosure can be carried out in a multiplex format whereby multiple different types of nucleic acids are detected in parallel using one or more steps of a method set forth herein. Other types of arrays can be used instead of bead arrays, including for example, those set forth in further detail below. Although it is also possible to serially process different types of nucleic acids using one or more steps of the methods set forth herein, parallel processing can provide cost savings, time savings and uniformity of conditions. An array or method of the present disclosure can be configured to include at least 2, 10, 100, $1 \times 10^3$, $1 \times 10^4$, $1 \times 10^5$, $1 \times 10^6$, $1 \times 10^9$, or more different nucleic acids. Alternatively or additionally, an array or method of the present disclosure can be configured to include at most $1 \times 10^9$, $1 \times 10^6$, $1 \times 10^5$, $1 \times 10^4$, $1 \times 10^3$, 100, 10, 2 or fewer, different nucleic acids. The nucleic acids can be attached to different sites of an array. As such, the number of sites in an array can be in a range exemplified here for different nucleic acids. Moreover, various reagents or products set forth herein (e.g. primer-template nucleic acid hybrids or stabilized ternary complexes) can be multiplexed to have different types or species in these ranges.

Further examples of commercially available arrays that can be used in a method of composition set forth herein include arrays made by photolithographic synthesis of nucleic acids, for example, an Affymetrix GeneChip™ array. A spotted array can also be used to attach presynthesized nucleic acids to array sites according to some embodiments. An exemplary spotted array is a CodeLink™ Array available from Amersham Biosciences. Another array that is useful is one that is manufactured using inkjet printing methods such as SurePrint™ Technology available from Agilent Technologies. The methods used for attaching nucleic acid probes to these arrays can be modified to attach nucleic acid primers for use in amplifying (e.g. via RCA) and/or sequencing target nucleic acids to which the primers hybridize.

Other useful arrays include those that are used in nucleic acid sequencing applications. For example, methods and compositions that are used to attach amplicons of genomic fragments (often referred to as clusters) to form arrays can be particularly useful. Examples are described in Bentley et al., Nature 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

A nucleic acid can be attached to a solid support (e.g. a site of an array) via covalent or non-covalent bonds. For example, a solid support can be covalently or non-covalently attached at or near the 5' end of a concatemeric nucleic acid. This configuration can result, for example, when the concatemer has been produced by RCA performed by extending a primer that is attached to the solid support at or near its 5' end. Attachment of a nucleic acid to a solid support can be mediated by any of a variety of surface chemistries such as reaction of a carboxylate moiety or succinimidyl ester moiety on the solid support with an amine-modified nucleic acid, reaction of an alkylating reagent (e.g. iodoacetamide or maleimide) on the solid support with a thiol-modified nucleic acid, reaction of an epoxysilane or isothiocyanate modified solid support with an amine-modified nucleic acid, reaction of an aminophenyl or aminopropyl modified solid support with a succinylated nucleic acid, reaction of an aldehyde or epoxide modified solid support with a hydrazide-modified nucleic acid or reaction of a thiol modified solid support with a thiol modified nucleic acid. The members of the preceding reactive pairs can be switched with regard to being present on the solid support or the nucleic acid. Click chemistry can be useful for attaching nucleic acids to solid supports. Exemplary reagents and methods for click chemistry are set forth in U.S. Pat. Nos. 6,737,236; 7,375,234; 7,427,678 and 7,763,736, each of which is incorporated herein by reference.

In particular embodiments, a stabilized ternary complex, polymerase, primer, template, primer-template nucleic acid hybrid or nucleotide is attached to a flow cell surface or to a solid support in a flow cell. One or more nucleic acid clusters can be attached to the flow cell surface or to the solid support in the flow cell. A flow cell allows convenient fluidic manipulation by passing solutions into and out of a fluidic chamber that contacts the support-bound analyte(s). The flow cell also provides for detection of the fluidically manipulated components. A detector can be positioned to detect signals from the solid support, such as signals from a label that is recruited to the solid support during a sequencing process, for example, due to formation of a stabilized ternary complex. Exemplary flow cells that can be used are described, for example, in US Pat. App. Pub. No. 2010/0111768 A1, WO 05/065814 or US Pat. App. Pub. No. 2012/0270305 A1, each of which is incorporated herein by reference.

In particular configurations, a nucleic acid cluster can be attached to a solid support by covalent attachment of one or both strands to the solid support. The nucleic acid can be single stranded or double stranded. In some configurations, a first strand of a double stranded nucleic acid is covalently attached to a solid support and the second strand is not covalently attached to the solid support. For example, the second strand can be retained in the cluster due to Watson-Crick base pairing to the first strand. A cluster that is formed by covalent attachment of a sense strand of a concatemer to a solid support can retain one or more antisense strands due to a plurality of base paired regions that effectively function to tangle the strands in the cluster.

A nucleic acid cluster can be made prior to, or as part of, a method set forth herein. In particular configurations, the nucleic acid cluster can include a nucleic acid concatemer. The cluster can consist of a single strand of a concatemer. The cluster need not contain an antisense strand for the concatemer nor for any region of the concatemer strand. Alternatively, the cluster can include a concatemeric sense strand and at least one antisense strand that complements all or part of the sense strand.

A useful method for producing a concatemeric nucleic acid on a solid support is rolling circle amplification (RCA). Generally, the method involves a polymerase extending a primer that is annealed to a circular template such that multiple laps of the polymerase around the circular template produces a concatemeric single stranded DNA that contains multiple tandem repeats, each of the repeats being complementary to the circular template. In one configuration, RCA can be performed initially in the presence of a low concentration of a polymer, such as dendrimers (e.g., polyamidoamine (PAMAM)), and subsequently in the presence of a polymer. In one configuration, an RCA reaction is stopped by denaturing the polymerase, for example, by heating the sample at 60° C., 65° C., 70° C., 75° C., 80° C., or more. In one configuration, an RCA reaction is stopped by removing one or more components of RCA, such as the polymerase, and dNTPs. Components of RCA can be removed by, for example, washing. Optionally, one or more antisense strands can be made by replicating the concatemeric sense strand, for example, using multiple displacement amplification (MDA). The RCA and MDA methods can be carried out isothermally. Generally, the polymerase used for RCA or MDA is a strand displacing polymerase. Methods and reagents that can be used for RCA, MDA or some combination thereof are set forth, for example, in Lizardi et al., Nat. Genet. 19:225-232 (1998), US Pat. Nos. 6,830,884; 6,797,474; 6,670,126; 6,576,448; 6,323,009; 6,280,949 or US 2007/0099208 A1, each of which is incorporated herein by reference.

FIGS. 1A-1D provide diagrammatic representations of methods for producing an immobilized concatemeric nucleic acid cluster on a solid support. As shown in FIG. 1A, a nucleic acid primer (indicated by the open and lined rectangles) is attached to a solid support (indicated by the dotted rectangle) via a linker (indicated by the grey line). The primer can be used to capture a target nucleic acid via a primer binding site that is complementary to the primer. In one configuration shown in FIG. 1A, the immobilized primer can hybridize to portions of the primer binding site that are present at opposite ends of a target sequence (the target sequence being indicated by a dotted line and the flanking primer binding site regions being indicated by open and lined rectangles, respectively). The immobilized primer thus functions as a splint that brings together the two ends of the target nucleic acid. The two ends can be ligated while hybridized to a splint nucleic acid to form a circular version of the target nucleic acid. In another configuration shown in FIG. 1A, a target nucleic acid is circularized prior to being hybridized to the immobilized primer on the solid support. For example, a linear target nucleic acid can be ligated while hybridized to a splint oligonucleotide in solution or on a solid support other than the solid support used for RCA. Alternatively, a splint need not be used to ligate the ends, for example, when using Circligase™ (Epicenter, Madison Wis.) or other enzyme capable of splint free ligation of nucleic acid ends. Again, immobilization can occur due to complementarity between the immobilized primer and a primer binding site in the circular template.

FIG. 1B provides a diagrammatic representation of a single stranded concatemer being produced via rolling circle amplification of a primed circular template that is hybridized to an immobilized primer. The primer is immobilized in a way that the 3' end is available for polymerase extension (e.g. the primer can be attached at or near its 5' end). The product of the first sub-step is shown as having progressed to a point that two copies of the circular template (two sequence units) have already been produced and the circular template is hybridized to a portion of a third copy (third sequence unit) that is being replicated. Each of the sequence units includes a region that is complementary to the target sequence (indicated by the solid black line) and a region that is complementary to the primer (indicated by the open and lined rectangles). The product of the second sub-step has progressed to the point of having produced nearly six copies of the circular template. FIG. 1B shows the final product of the RCA reaction after the circular template is absent (e.g., has been removed) in the third sub-step. Two regions of the final product are shown for illustrative purposes: a region where the sequence units are delineated (indicative of the concatemeric primary structure of the sense strand) and a region where the number and conformation of the sequence units is not specified (indicative of the dynamic and variable secondary structure for the cluster as a whole). The steps diagrammed in FIGS. 1A-1D and set forth above can be carried out in multiplex, such that the diagrammed steps occur at a plurality of individual sites in an array.

In particular configurations, a nucleic acid cluster can be made by (i) providing a sense strand of a concatemer on a solid support, and (ii) synthesizing an antisense strand using an amplification primer that binds to a primer binding site in the sense strand.

Accordingly, the present disclosure provides a method for determining sequences from sense and antisense strands of a nucleic acid, including steps of (a) (i) providing the sense strand of a concatemer on a solid support, and (ii) synthesizing an antisense strand of the concatemer using an amplification primer that binds to a primer binding site in a sequence unit of the sense strand, thereby providing a nucleic acid cluster attached to a solid support, wherein the nucleic acid cluster includes the sense strand of the concatemer and the antisense strand of the concatemer, wherein the concatemer includes multiple copies of the sequence unit linked in series, wherein the sequence unit includes a target sequence and the primer binding site; (b) hybridizing a primer to the primer binding site in a sequence unit of the antisense strand in the cluster; (c) extending the primer along the antisense strand to determine the sequence from at least a portion of the target sequence in the antisense strand; (d) hybridizing a second primer to the primer binding site in a sequence unit of the sense strand; and (e) extending the second primer along the sense strand to determine the sequence from at least a portion of the target sequence in the sense strand.

One or more antisense strands can be produced as set forth in FIG. 1C. Amplification can start with a concatemer sense strand (indicated as the black line) that is immobilized via a linker (indicated by the grey line) on a solid support (indicated by the dot filled rectangle). The sense strand of the concatemer includes sequence units that each include a primer binding site. Amplification primers that complement all or part of the primer binding site can be hybridized to the concatemer sense strand and extended in an MDA reaction to produce antisense strands (shown as grey lines annealed, at least partially, to the sense strand). For purposes of illustration, a portion of the MDA product is shown to indicate the direction of extension (see arrowheads) and to indicate primary structure of the concatemeric antisense strands having a variety of lengths and annealing patterns. Another portion of the MDA product is shown with less structural specificity to indicate the dynamic and variable secondary structure for the cluster as a whole.

A nucleic acid cluster can be made prior to or as part of a method set forth herein, for example, by (i) providing a solid support having a capture primer, (ii) hybridizing a circular nucleic acid template to the primer, (iii) synthesizing a sense strand of a concatemer by extending the capture primer along the circular nucleic acid template by rolling circle amplification, and (iv) synthesizing an antisense strand of the concatemer by extending an amplification primer that binds to a primer binding site in a sequence unit of the sense strand.

Accordingly, the present disclosure provides a method for determining sequences from sense and antisense strands of a nucleic acid, including steps of (a) (i) providing a solid support having a capture primer, (ii) hybridizing a circular nucleic acid template to the primer, (iii) synthesizing a sense strand of a concatemer by extending the capture primer along the circular nucleic acid template by rolling circle amplification, and (iv) synthesizing an antisense strand of the concatemer by extending an amplification primer that binds to a primer binding site in a sequence unit of the sense strand, thereby providing a nucleic acid cluster attached to a solid support, wherein the nucleic acid cluster includes the sense strand of the concatemer and the antisense strand of the concatemer, wherein the concatemer includes multiple copies of the sequence unit linked in series, wherein the sequence unit includes a target sequence and the primer binding site; (b) hybridizing a primer to the primer binding site in a sequence unit of the antisense strand in the cluster; (c) extending the primer along the antisense strand to determine the sequence from at least a portion of the target sequence in the antisense strand; (d) hybridizing a second primer to the primer binding site in a sequence unit of the sense strand; and (e) extending the second primer along the sense strand to determine the sequence from at least a portion of the target sequence in the sense strand.

The sense strand and antisense strands of a concatemer can be produced as set forth in FIG. 1D. Optionally, a circular template can be captured on a solid support as diagrammed in FIG. 1A. Whether or not the diagrammed capture method is used, a primer can be immobilized in a way that the 3' end is available for polymerase extension (e.g. the primer can be attached at or near its 5' end). FIG. 1D shows a combined RCA/MDA reaction in which the product of the first sub-step is shown as having progressed to a point that the sense strand includes two copies of the circular template (two sequence units) and the circular template is hybridized to a portion of a third copy (third sequence unit) that is being replicated. Each of the sequence units in the sense strand includes a region that is complementary to the target sequence (indicated by the solid black line) and a region that is complementary to the primer (indicated by the open and lined rectangles).

Since the reaction of FIG. 1D includes amplification primers that are complementary to the primer binding sites in the sense strand, the product of the first sub-step also includes three antisense strands, shown at various stages of extension. Each of the sequence units in the antisense strands includes a region that is a copy of the target sequence (indicated by the solid grey line) and a region that is complementary to the primer (indicated by the open and lined rectangles). The product of the second sub-step in FIG. 1D has progressed to the point of having produced nearly six copies of the circular template and five antisense strands shown at various stages of extension. FIG. 1D shows the final product of the combined RCA/MDA reaction after the circular template is absent (e.g., has been removed) in the third sub-step. Two regions of the final product are shown including a region where the sequence units are delineated to illustrate primary structure of the concatemer and a region of where the number and conformation of the sequence units is not specified (indicative of the dynamic and variable secondary structure for the cluster as a whole). The steps diagrammed in FIG. 1D and set forth above can be carried out in multiplex, such that the diagrammed steps occur at a plurality of individual sites in an array.

An MDA method, such as those exemplified in the context of FIG. 1C or FIG. 1D, can be used to produce one or more antisense strands that complement at least a portion of the concatemer. The amplification primers can be in solution as shown in the figures. Alternatively, the amplification primers can be attached to the solid support, for example, using covalent or non-covalent attachment chemistries set forth herein for nucleic acids. FIGS. 4A-4F illustrate a non-limiting exemplary MDA method with the amplification primers attached to the solid support. An antisense strand of a concatemer that results from extension of a covalently immobilized primer will be covalently attached to the solid support. An amplification primer need not be covalently attached to the solid support, instead being attached to the cluster by hybridization to the sense strand. The antisense strand of the concatemer that results from extension of a primer that is not covalently attached to a solid support can be attached to a cluster via hybridization to the sense strand or due to non-covalent bonds to other moieties in the cluster.

As exemplified by FIG. 1C, sense and antisense strands of a concatemer can be produced in separate reactions. For example, a sense concatemer strand can be produced by an RCA reaction and then the sense concatemer can be used as a template for a subsequent MDA reaction. Accordingly, RCA can be carried out to produce an sense concatemer strand that is attached to a solid support, then reagents used for RCA can be removed from contact with the solid support and then reagents for MDA (e.g. primers that complement primer binding sites in the sense strand) can be contacted with the solid support. Alternatively, sense and antisense strands of a concatemer can be produced in a 'single pot' reaction such that RCA reagents are not separated from MDA reagents. For example, a first primer that is used to amplify a circular template via RCA can be present with a second primer that is used to amplify a concatemer via MDA. See, for example, FIG. 1D. The first and second primers can be extended in each other's presence. If desired, sense and antisense strands of a concatemer can be produced simultaneously, for example, by simultaneously performing RCA and MDA reactions.

Figure 1E:
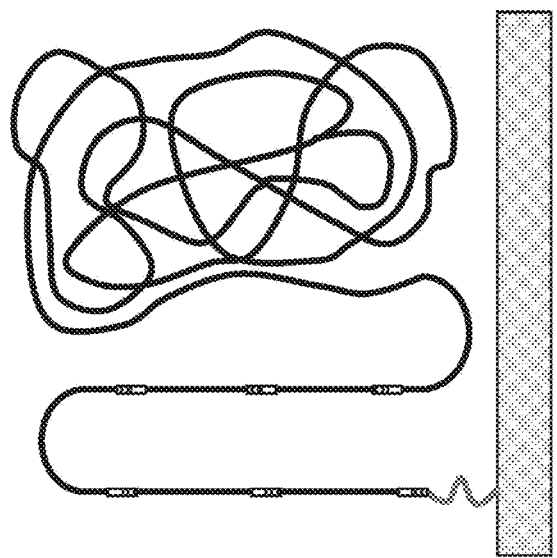
FIG. 1E shows a diagrammatic representation of extending a plurality of primers (e.g., amplification primers) along an immobilized sense strand of a concatemer to produce a cluster having the immobilized sense strand hybridized to a plurality of antisense strands of the concatemer where one, one or more, or each, of the plurality of antisense strands comprises one or more nucleotides or bases that can label or target the antisense strands for degradation. For example, an antisense strand can include one or more nucleotides that are uridine monophosphate. As another example, an antisense strand can include one or more nucleotides that are deoxyribose pseudouridine monophosphate. For example, an antisense strand can include one or more bases that are uracil. As another example, an antisense strand can include one or more modified bases or one or more modified nucleotides. As a further example, an antisense strand can include one or more bases that are non-canonical bases or one or more non-canonical nucleotides.
Figure 1E:
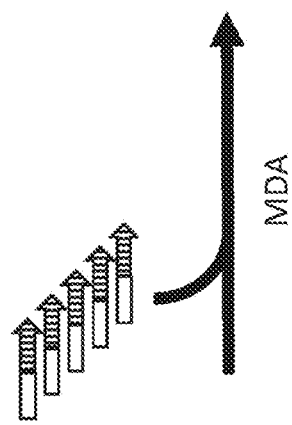
Figure 1E:
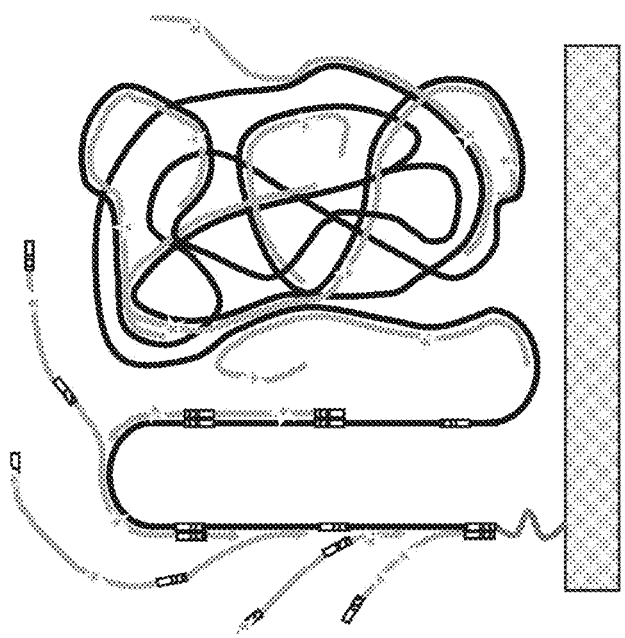

One or more antisense strands can be produced as set forth in FIG. 1E. Amplification can start with a concatemer sense strand (indicated as the black line) that is immobilized via a linker (indicated by the grey line) on a solid support (indicated by the dot filled rectangle). The sense strand of the concatemer includes sequence units that each include a primer binding site. Amplification primers that complement all or part of the primer binding site can be hybridized to the concatemer sense strand and extended in an MDA reaction to produce antisense strands (shown as grey lines annealed, at least partially, to the sense strand). For purposes of illustration, a portion of the MDA product is shown to indicate the direction of extension (see arrowheads) and to indicate primary structure of the concatemeric antisense strands having a variety of lengths and annealing patterns. Another portion of the MDA product is shown with less structural specificity to indicate the dynamic and variable secondary structure for the cluster as a whole.

The MDA reaction can be carried out in the presence of deoxyribose adenosine triphosphate (dATP), deoxyribose thymidine triphosphate (dTTP), deoxyribose guanosine triphosphate (dGTP), and deoxyribose cytidine triphosphate (dCTP) (or analogues thereof). The antisense strands generated can include adenine, guanine, cytosine and thymine bases. The MDA reaction can be carried out in the presence of deoxyribose uridine triphosphate (dUTP) (or analogues thereof). The antisense strands generated can include uracil bases (indicated by "stars" in the antisense strand) in addition to adenine, guanine, cytosine and thymine bases when the MDA reaction is carried out in the presence of dUTP in addition to dATP, dTTP, dGTP, and dCTP. The locations of uracil bases in the antisense strand are not predetermined. As described in further detail below with reference to FIG. 2D, antisense strands with uridine bases can be digested after the antisense strands are sequenced. Although the present application describes that the MDA reaction can be carried out in the presence of dUTP (or analogues thereof) such that the antisense strands generated include uracil bases, this is for illustration only and alternatives accomplishing a similar outcome are also contemplated. For example, the MDA reaction can be carried out in the presence of deoxyribonucleotide triphosphate with a modified base or a non-canonical base such that the antisense strands generated include one or more bases that are modified or non-canonical. Such modified bases or non-canonical bases can target the antisense strands for degradation, such as enzymatic digestion as described below with reference to FIG. 2D. As another example, the MDA reaction can be carried out in the presence of modified or non-canonical deoxyribonucleotide triphosphate (e.g., deoxy pseudouridine triphosphate) such that the antisense strands generated include one or more nucleotides that are modified or non-canonical (e.g., deoxyribose pseudouridine monophosphate). Such modified nucleotide or non-canonical nucleotides can target the antisense strands for degradation, such as enzymatic digestion as described below with reference to FIG. 2D.

Whether a base in an antisense strand is a thymine or an uracil (when the corresponding base in the sense strand is adenine) depends on the relative concentration of dTTP and dUTP in the MDA reaction. The concentration of dUTP (or deoxyribonucleotide trisphosphate with a modified base or a non-canonical base, or deoxyribonucleotide trisphosphate that is modified or non-canonical) in an MDA reaction can be lower than the concentration of another deoxyribose nucleotide triphosphate in the MDA reaction such that the percentage of uracil bases (or modified bases or non-canonical bases or nucleotides that are modified or non-canonical) present in the antisense strand is low. The uracil bases (or modified bases or non-canonical bases or nucleotides that are modified or non-canonical) can be randomly distributed and present at a low percentage such that two antisense strands (any two antisense strands) include uracil bases (or modified bases or non-canonical bases or nucleotides that are modified or non-canonical) at different positions.

The concentration of a deoxyribonucleotide triphosphate (e.g., dATP, dTTP, dGTP, or dCTP), or the concentration of all deoxyribonucleotide triphosphates, in an MDA reaction can be about, be at least, be at least about, be at most, or be at most about, 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, or a number or a range between any two of these values. The concentration of dUTP in an MDA reaction can be, be about, be at least, be at least about, be at most, or be at most about, 0.001 mM, 0.002 mM, 0.003 mM, 0.004 mM, 0.005 mM, 0.006 mM, 0.007 mM, 0.008 mM, 0.009 mM, 0.01 mM, 0.02 mM, 0.03 mM, 0.04 mM, 0.05 mM, 0.06 mM, 0.07 mM, 0.08 mM, 0.09 mM, 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, or a number or a range between any two of these values. The ratio of the concentration of dUTP (or deoxyribonucleotide trisphosphate with a modified base or a non-canonical base, or deoxyribonucleotide trisphosphate that is modified or non-canonical) relative to the concentration of dTTP (or the concentration of another deoxyribonucleotide triphosphate or the total concentration of deoxyribonucleotide triphosphate other than dUTP or deoxyribonucleotide trisphosphate with a modified base or a non-canonical base or deoxyribonucleotide trisphosphate that is modified or non-canonical) can be, be about, be at least, be at least about, be at most, or be at most about, 1:100, 1:99, 1:98, 1:97, 1:96, 1:95, 1:94, 1:93, 1:92, 1:91, 1:90, 1:89, 1:88, 1:87, 1:86, 1:85, 1:84, 1:83, 1:82, 1:81, 1:80, 1:79, 1:78, 1:77, 1:76, 1:75, 1:74, 1:73, 1:72, 1:71, 1:70, 1:69, 1:68, 1:67, 1:66, 1:65, 1:64, 1:63, 1:62, 1:61, 1:60, 1:59, 1:58, 1:57, 1:56, 1:55, 1:54, 1:53, 1:52, 1:51, 1:50, 1:49, 1:48, 1:47, 1:46, 1:45, 1:44, 1:43, 1:42, 1:41, 1:40, 1:39, 1:38, 1:37, 1:36, 1:35, 1:34, 1:33, 1:32, 1:31, 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, or a number ora range between any two of these values. The percentage of deoxyribonucleotide triphosphates in the MDA reaction that are dUTP (or deoxyribonucleotide trisphosphate with a modified base or a non-canonical base, or deoxyribonucleotide trisphosphate that is modified or non-canonical) can be, be about, be at least about, be at most, or be at most about, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or a number or a range between any two of these values.

The concentration of dUTP (or deoxyribonucleotide trisphosphate with a modified base or a non-canonical base, or deoxyribonucleotide trisphosphate that is modified or non-canonical) relative to another deoxyribose nucleotide triphosphate such as dTTP in an MDA reaction can be low such that the percentage of uracil bases (or modified bases or non-canonical bases or deoxyribonucleotides that are modified or non-canonical) present in the antisense strand is low. The ratio of nucleotides with bases that are uracil (or modified bases or non-canonical bases or nucleotides that are modified or non-canonical) relative to the bases that are thymine (or another base, or all bases that are not uracil) can be, be about, be at least, be at least about, be at most, or be at most about, 1:10000, 1:9000, 1:8000, 1:7000, 1:6000, 1:5000, 1:6000, 1:5000, 1:4000, 1:3000, 1:2000, 1:1000, 1:900, 1:800, 1:700, 1:600, 1:500, 1:400, 1:300, 1:200, 1:100, 1:99, 1:98, 1:97, 1:96, 1:95, 1:94, 1:93, 1:92, 1:91, 1:90, 1:89, 1:88, 1:87, 1:86, 1:85, 1:84, 1:83, 1:82, 1:81, 1:80, 1:79, 1:78, 1:77, 1:76, 1:75, 1:74, 1:73, 1:72, 1:71, 1:70, 1:69, 1:68, 1:67, 1:66, 1:65, 1:64, 1:63, 1:62, 1:61, 1:60, 1:59, 1:58, 1:57, 1:56, 1:55, 1:54, 1:53, 1:52, 1:51, 1:50, 1:49, 1:48, 1:47, 1:46, 1:45, 1:44, 1:43, 1:42, 1:41, 1:40, 1:39, 1:38, 1:37, 1:36, 1:35, 1:34, 1:33, 1:32, 1:31, 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, or a number or a range between any two of these values. The percentage of bases in the antisense strand that are uracil can be, be about, be at least about, be at most, or be at most about, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or a number or a range between any two of these values.

A nucleic acid cluster can be made prior to or as part of a method set forth herein, for example, by (i) providing a solid support having a capture primer, (ii) hybridizing a circular nucleic acid template to the primer, (iii) synthesizing a sense strand of a concatemer by extending the capture primer along the circular nucleic acid template by rolling circle amplification, and (iv) synthesizing an antisense strand of the concatemer by extending an amplification primer that binds to a primer binding site in a sequence unit of the sense strand, wherein the antisense strand comprises one or more bases that are uracil.

Accordingly, the present disclosure provides a method for determining sequences from sense and antisense strands of a nucleic acid, including steps of (a) (i) providing a solid support having a capture primer, (ii) hybridizing a circular nucleic acid template to the primer, (iii) synthesizing a sense strand of a concatemer by extending the capture primer along the circular nucleic acid template by rolling circle amplification, and (iv) synthesizing an antisense strand of the concatemer by extending an amplification primer that binds to a primer binding site in a sequence unit of the sense strand, wherein the antisense strand comprises one or more bases that are uracil, thereby providing a nucleic acid cluster attached to a solid support, wherein the nucleic acid cluster includes the sense strand of the concatemer and the antisense strand of the concatemer, wherein the concatemer includes multiple copies of the sequence unit linked in series, wherein the sequence unit includes a target sequence and the primer binding site; (b) hybridizing a primer to the primer binding site in a sequence unit of the antisense strand in the cluster; (c) extending the primer along the antisense strand to determine the sequence from at least a portion of the target sequence in the antisense strand; (d) hybridizing a second primer to the primer binding site in a sequence unit of the sense strand; and (e) extending the second primer along the sense strand to determine the sequence from at least a portion of the target sequence in the sense strand.

The methods for determining sequences from sense and antisense strands of a nucleic acid disclosed herein can be used for determining sequences from sense and antisense strands of nucleic acids in a sample. Advantageously, the methods may have no, or minimal, biases or preferences for nucleic acids of certain sizes such that the size distribution of the nucleic acids in the sample being sequences is the same as, or similar to or comparable to, the size distribution of the target sequences actually sequenced. The size distribution of the nucleic acids in the sample being sequences is the same as, or similar to or comparable to, the size distribution of the reads generated from sequencing the first strands and/or the second strands. The distribution can be, for example, a normal distribution.

Particularly useful sequencing processes that can be carried out in a method set forth herein are cyclical processes that employ repeated cycles of reagent delivery. Each cycle can include one step or multiple steps. For example, each cycle can include all steps needed to detect a single nucleotide position in a template nucleic acid. Some sequencing processes employ cyclical reversible terminator (CRT) chemistry in which each cycle includes steps for (i) adding a single reversibly terminated nucleotide to increment a nascent primer to a nucleotide position that is to be detected; (ii) detecting the nucleotide at the single nucleotide position, and (iii) deblocking the nascent primer to allow a return to step (i) to start a subsequent cycle.

A method for determining sequences from sense and antisense strands of a nucleic acid can include steps of (a) providing a nucleic acid cluster attached to a solid support, wherein the nucleic acid cluster includes a sense strand of a concatemer and an antisense strand of the concatemer, wherein the concatemer includes multiple copies of a sequence unit linked in series, wherein the sequence unit includes a target sequence and a primer binding site; (b) hybridizing a primer to the primer binding site in a sequence unit of the antisense strand in the cluster; (c) extending the primer along the antisense strand to determine the sequence from at least a portion of the target sequence in the antisense strand; (d) hybridizing a second primer to the primer binding site in a sequence unit of the sense strand; and (e) extending the second primer along the sense strand to determine the sequence from at least a portion of the target sequence in the sense strand. Optionally, the extending of the second primer in step (e) includes repeated cycles of (i) adding a reversibly terminated nucleotide to the second primer and (ii) deblocking the reversibly terminated nucleotide on the second primer. As an additional or alternative option, the extending of the primer in step (c) can include repeated cycles of (i) adding a reversibly terminated nucleotide to the primer and (ii) deblocking the reversibly terminated nucleotide on the primer.

Whether one or both of steps (c) and (e) include repeated steps (i) and (ii) as set forth above, the repeated cycles in step (c) and/or (e) can optionally include (iii) detecting a stabilized ternary complex that includes a polymerase, next correct nucleotide and the second primer hybridized to the antisense or sense strand, respectively. As a further option, the next correct nucleotide or the polymerase can have a label that is detected in step (c) and/or (e) to produce a signal, the signal being used to determine the sequence from at least the portion of the target sequence in the antisense or sense strand, respectively.

A specific example of a useful CRT nucleic acid sequencing process is a Sequencing By Binding™ (SBB™) reaction, for example, as described in commonly owned US Pat. App. Pub. Nos. 2017/0022553 A1; 2018/0044727 A1; 2019/0169688 A1; 2019/0345544 A1; 2019/0367974 A1, each of which is incorporated herein by reference. Generally, SBB™ methods for determining the sequence of a template nucleic acid molecule can be based on formation of a stabilized ternary complex (between polymerase, primed nucleic acid and cognate nucleotide) under specified conditions. The method can include an examination phase and a nucleotide incorporation phase.

The examination phase of an SBB™ process can be carried out for at least one template nucleic acid molecule primed with a primer, a polymerase and at least one nucleotide type. Interaction of polymerase and a nucleotide with the primed template nucleic acid molecule(s) can be observed under conditions where the nucleotide is not covalently added to the primer(s); and the next base in each template nucleic acid can be identified based on the observed interaction. For example, the nucleotides can contain a detectable label. In some embodiments, the polymerase can be labeled. A variety of conditions and reagents can be useful to stabilize a ternary complex during the examination phase. For example, the primer can contain a reversible blocking moiety that prevents covalent attachment of nucleotide; and/or polymerase cofactors that are required for extension, such as divalent metal ions, can be absent; and/or inhibitory divalent cations that inhibit polymerase-based primer extension can be present; and/or the polymerase that is present in the examination phase can have a chemical modification and/or mutation that inhibits primer extension; and/or the nucleotides can have chemical modifications that inhibit incorporation. In particular embodiments, a ternary complex is stabilized by the presence of $Li^+$, betaine or both. For example, reagents and techniques set forth in U.S. Pat. No. 10,400,272 (which is incorporated herein by reference) can be used.

It will be understood that options set forth herein for stabilizing a ternary complex need not be mutually exclusive and instead can be used in various combinations. For example, a ternary complex can be stabilized by one or a combination of means including, but not limited to, cross-linking of the polymerase domains, crosslinking of the polymerase to the nucleic acid, polymerase mutations that stabilize the ternary complex, allosteric inhibition by small molecules, uncompetitive inhibitors, competitive inhibitors, non-competitive inhibitors, absence of catalytic metal ions, presence of a blocking moiety on the primer, and other means set forth herein.

Generally, detection can be achieved in an examination step by methods that perceive a property that is intrinsic to a ternary complex or a label moiety attached thereto. Exemplary properties upon which detection can be based include, but are not limited to, mass, electrical conductivity, energy absorbance, luminescence or the like. Detection of luminescence can be carried out using methods known in the art pertaining to nucleic acid arrays. A luminophore can be detected based on any of a variety of luminescence properties including, for example, emission wavelength, excitation wavelength, fluorescence resonance energy transfer (FRET), quenching, anisotropy or lifetime. Other detection techniques that can be used in a method set forth herein include, for example, mass spectrometry which can be used to perceive mass; surface plasmon resonance which can be used to perceive binding of polymerase or other analyte at a surface; absorbance which can be used to perceive the wavelength of the energy a label absorbs; calorimetry which can be used to perceive changes in temperature due to presence of a label; electrical conductance or impedance which can be used to perceive electrical properties of a label, or other known analytic techniques.

The extension phase can be carried out by creating conditions where a nucleotide can be added to a primer hybridized to a template nucleic acid molecule. In some embodiments, this involves removal of reagents used in the examination phase and replacing them with reagents that facilitate extension. For example, examination reagents can be replaced with a polymerase and reversibly terminated nucleotide(s).

Nucleotide analogs that participate in stabilized ternary complexes, or that are added to a primer by polymerase catalysis, can include terminator moieties that reversibly prevent subsequent nucleotide incorporation at the 3'-end of the primer after the analog has been incorporated into the primer. For example, U.S. Pat. Nos. 7,544,794 and 8,034,923 (the disclosures of these patents are incorporated herein by reference) describe reversible terminator moieties in which the 3'-OH group is replaced by a 3'-$ONH_2$ moiety. Another type of reversible terminator moiety is linked to the nitrogenous base of a nucleotide as set forth, for example, in U.S. Pat. No. 8,808,989 (the disclosure of which is incorporated herein by reference). Other reversible terminator moieties that similarly can be used in connection with the methods described herein include those described in references cited elsewhere herein or in U.S. Pat. Nos. 7,956,171, 8,071,755, and 9,399,798 (the disclosures of these U.S. patents are incorporated herein by reference). In certain embodiments, a reversible terminator moiety can be modified or removed from a primer, in a process known as "deblocking," allowing for subsequent nucleotide incorporation.

A deblocking process when included in a method set forth herein can facilitate sequencing of a primer-template nucleic acid hybrid. The deblocking process can be used to convert a reversibly terminated primer into an extendable primer. Primer extension can then be used to move the site of ternary complex formation to a different location along the template nucleic acid. Repeated cycles of extension, examination and deblocking can be used to reveal the sequence of template nucleic acid. Each cycle reveals a subsequent base in the template nucleic acid. Exemplary reversible terminator moieties, methods for incorporating them into primers and methods for modifying the primers for further extension (often referred to as 'deblocking') are set forth in U.S. Pat. Nos. 7,427,673; 7,414,116; 7,544,794; 7,956,171; 8,034,923; 8,071,755; 8,808,989; or 9,399,798. Further examples are set forth in Bentley et al., *Nature* 456:53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference.

In particular embodiments, reagents that are used during a primer modification step (e.g. extending the primer via addition of a nucleotide or capping the primer via addition of a ternary complex inhibitor moiety) are removed from contact with the primer-template hybrid prior to a step of forming a stabilized ternary complex with the primer-template hybrid. For example, removal of a nucleotide mixture that was used for an extension step can be desirable when one or more types of nucleotides in the mixture would interfere with formation or detection of a ternary complex in a subsequent examination step. Similarly, it may be desirable to remove polymerases or cofactors that were used in a primer modification step so as to prevent unwanted catalytic activity during a subsequent examination step. However, if desired, the nucleotides from an extension step can be removed whereas the polymerase from the extension step is retained and carried through to a step of forming a ternary complex. See, for example, US Pat. App. Pub. No. 2020/0032317 A1, which is incorporated herein by reference. Accordingly, the ternary complex that is detected in an examination step can include a polymerase molecule that was used in a previous primer extension step. Removal of reaction components can be followed by a wash step, wherein an inert fluid is used to purge the primer-template hybrid of residual components of the reagent mixture used for primer modification.

Another useful CRT sequencing process is sequencing-by-synthesis (SBS). SBS generally involves the enzymatic extension of a nascent primer through the iterative addition of nucleotides against a template strand to which the primer is hybridized. Briefly, SBS can be initiated by contacting primed, target nucleic acids with one or more labeled nucleotides, DNA polymerase, etc. The primers will incorporate a labeled nucleotide that can be detected. The label in the labeled nucleotide can be removed. A molecular scar can remain after the label in the labeled nucleotide is removed. In comparison, the nucleotide incorporated into a primed template during an extension phase can be a nucleotide that is not labeled, such as a natural nucleotide. Accordingly, no label needs to be removed from the incorporated nucleotide. Optionally, the labeled nucleotides can further include a reversible terminator moiety. As such, a single reversibly terminated nucleotide will be added to the primer such that subsequent extension cannot occur until a deblocking agent is delivered to remove the reversible terminator moiety from the primer. The SBS cycle can be performed n times to extend the primer by n nucleotides, thereby detecting a sequence of length n. Exemplary SBS procedures, reagents and detection components that can be readily adapted for use with a system or apparatus herein are described, for example, in Bentley et al., Nature 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference. Also useful are SBS methods that are commercially available from Illumina, Inc. (San Diego, Calif.).

Accordingly, a method for determining sequences from sense and antisense strands of a nucleic acid can include steps of (a) providing a nucleic acid cluster attached to a solid support, wherein the nucleic acid cluster includes a sense strand of a concatemer and an antisense strand of the concatemer, wherein the concatemer includes multiple copies of a sequence unit linked in series, wherein the sequence unit includes a target sequence and a primer binding site; (b) hybridizing a primer to the primer binding site in a sequence unit of the antisense strand in the cluster; (c) extending the primer along the antisense strand to determine the sequence from at least a portion of the target sequence in the antisense strand; (d) hybridizing a second primer to the primer binding site in a sequence unit of the sense strand; and (e) extending the second primer along the sense strand to determine the sequence from at least a portion of the target sequence in the sense strand. Optionally, the extending of the second primer in step (e) includes repeated cycles of (i) adding a reversibly terminated nucleotide to the second primer and (ii) deblocking the reversibly terminated nucleotide on the second primer. As an additional or alternative option, the extending of the primer in step (c) can include repeated cycles of (i) adding a reversibly terminated nucleotide to the primer and (ii) deblocking the reversibly terminated nucleotide on the primer.

Whether one or both of steps (c) and (e) include repeated steps (i) and (ii) as set forth above, the reversibly terminated nucleotide that is added to a primer in step (c) or (e) can optionally have a label that is detected to produce a signal, the signal being used to determine the sequence from at least the portion of the target sequence in the antisense or sense strand, respectively. As a further option, the repeated cycles in one or both of steps (c) and (e) can further include (iii) removing the label after the label is detected.

Some SBS embodiments are cyclical but need not employ reversible terminator nucleotides. A particularly useful method includes detection of a proton released upon incorporation of a nucleotide into an extension product. For example, sequencing based on detection of released protons can use reagents and an electrical detector that are commercially available from Thermo Fisher (Waltham, Mass.) or described in US Pat. App. Pub. Nos. 2009/0026082 A1; 2009/0127589 A1; 2010/0137143 A1; or 2010/0282617 A1, each of which is incorporated herein by reference. Another cyclical sequencing process that need not employ reversible terminator nucleotides is pyrosequencing. Pyrosequencing detects the release of inorganic pyrophosphate (PPi) as nucleotides are incorporated into a nascent primer hybridized to a template nucleic acid strand (Ronaghi, et al., Analytical Biochemistry 242 (1), 84-9 (1996); Ronaghi, Genome Res. 11 (1), 3-11 (2001); Ronaghi et al. Science 281 (5375), 363 (1998); U.S. Pat. Nos. 6,210,891; 6,258,568 and 6,274,320, each of which is incorporated herein by reference).

Sequencing-by-ligation reactions are also useful including, for example, those described in Shendure et al. Science 309:1728-1732 (2005); U.S. Pat. Nos. 5,599,675; or 5,750,341, each of which is incorporated herein by reference. Sequencing-by-hybridization procedures can be used as described, for example, in Bains et al., Journal of Theoretical Biology 135 (3), 303-7 (1988); Drmanac et al., Nature Biotechnology 16, 54-58 (1998); Fodor et al., Science 251 (4995), 767-773 (1995); or WO 1989/10977, each of which is incorporated herein by reference. In both sequencing-by-ligation and sequencing-by-hybridization procedures, primers that are hybridized to nucleic acid templates are subjected to repeated cycles of extension by oligonucleotide ligation, for example, using fluorescently labeled oligonucleotides.

A reagent removal or wash procedure can be performed between any of a variety of steps set forth herein. Such procedures can be used to remove one or more of the reagents that are present in a reaction vessel or on a solid support. For example, a reagent removal or wash step can be useful for separating a primer-template hybrid from other reagents that were contacted with the primer-template hybrid under ternary complex stabilizing conditions. In particular embodiments, separation of reagents is facilitated by attachment of a reagent of interest, such as a primer-template hybrid, to a solid support and removal of fluid from contact with the solid support. One or more of the reagents set forth herein can be attached to a solid support or provided in solution as desired to suit a particular use of the methods or apparatus set forth herein.

A sequencing method can include multiple repetitions of cycles, or steps within cycles, set forth herein. For example, examination and primer modification steps can be repeated multiple times as can optional steps of deblocking primers or washing away unwanted reactants or products between various steps. Accordingly, a nucleic acid can be subjected to at least 2, 5, 10, 25, 50, 100, 150, 200 or more repeated cycles of a sequencing method set forth herein. Fewer cycles can be carried out when shorter read lengths are desired. As such, a nucleic acid can be subjected to at most 200, 150, 100, 50, 25, 10, 5 or 2 cycles of a sequencing method set forth herein. The above ranges for cycle number can apply to any of the cyclic reversible terminator processes set forth herein. In some embodiments, a sequencing method can be carried out for a predetermined number of repeated cycles. Alternatively, the cycles can be repeated until a particular empirically observed state is reached. For example, cycles can be repeated so long as signal is above an observable threshold, noise is below an observable threshold or signal-to-noise ratio is above an observable threshold.

Other examples of sequencing methods that can be used in a method set forth herein include methods employed on platforms commercialized by Illumina™, Inc. (e.g. HiSeq™, MiSeq™, NextSeq™, or NovaSeq™ systems), Life Technologies™ (e.g. ABI PRISM™, or SOLiD™ systems), Pacific Biosciences (e.g. systems using SMRT™ Technology such as the Sequel™ or RS II™ systems), MGI Tech (DNBSEQ-T7, MGISEQ-2000, MGISEQ-200, or BGISEQ-500), or Qiagen (e.g. Genereader™ system).

A method set forth herein for determining the sequence of a sense and antisense strand of a nucleic acid can be carried out under conditions where the antisense strand is present while the sense strand is sequenced (See FIG. 2B for an example). In an alternative configuration of the method, the antisense strand can be absent during the sequencing of the sense strand (See FIGS. 2C and 2D for examples).

A method set forth herein for determining the sequence of a sense and antisense strand of a nucleic acid can be carried out under conditions where the sense strand is present while the antisense strand is sequenced (See FIG. 2A for an example). In an alternative configuration of the method, the sense strand can be absent during the sequencing of the antisense strand.

A method set forth herein for determining the sequence of a sense and antisense strand of a nucleic acid can be carried out under conditions where the sense strand is present while the antisense strand is sequenced, and wherein the antisense strand is present while the sense strand is sequenced (See FIGS. 2A and 2B for an example). In an alternative configuration of the method, the sense strand can be absent during the sequencing of the antisense strand, and the antisense strand can be absent during the sequencing of the sense strand.

A method set forth herein for determining the sequence of a sense and antisense strand of a nucleic acid can be carried out under conditions wherein the antisense strand is hybridized to a primer (e.g. a non-extended primer or an extended primer that is produced by sequencing the antisense strand) while the sense strand is sequenced (See FIG. 2B for an example). In an alternative configuration of the method, the sequencing primer that is extended during sequencing of the antisense strand can be absent during the sequencing of the sense strand (See FIGS. 2C and 2D for examples).

A method set forth herein for determining the sequence of a sense and antisense strand of a nucleic acid can be carried out under conditions wherein the sense strand is hybridized to a primer (e.g. a non-extended primer or an extended primer that is produced by sequencing the sense strand) while the antisense strand is sequenced. In an alternative configuration of the method, the sequencing primer that is extended during sequencing of the sense strand can be absent during the sequencing of the antisense strand.

A method set forth herein for determining the sequence of a sense and antisense strand of a nucleic acid can be carried out under conditions where the sense strand is hybridized to a primer (e.g. a non-extended primer or an extended primer that is produced by sequencing the sense strand) while the antisense strand is sequenced, and wherein the antisense strand is hybridized to a primer (e.g. a non-extended primer or an extended primer that is produced by sequencing the antisense strand) while the sense strand is sequenced. In an alternative configuration of the method, the sequencing primer that is extended during sequencing of the sense strand can be absent during the sequencing of the antisense strand, and the sequencing primer that is extended during sequencing of the antisense strand can be absent during the sequencing of the sense strand.

A method set forth herein for determining the sequence of a sense and antisense strand of a nucleic acid can be carried out where the step of determining the sequence of the sense strand and the step of synthesizing the antisense strand occur simultaneously. For example, during the step of determining the sequence of the sense strand, part of the antisense strand is synthesized. FIGS. 3A-3F illustrate a non-limiting exemplary method of determining the sequence of a sense and antisense strand of a nucleic acid where the antisense strand synthesized includes the extension product from sequencing the sense strand.

Accordingly, the present disclosure provides a method for determining sequences from sense and antisense strands of a nucleic acid. The method can include steps of (a) providing a nucleic acid cluster attached to a solid support, wherein the nucleic acid cluster includes a sense strand of a concatemer and an antisense strand of the concatemer, wherein the concatemer includes multiple copies of a sequence unit linked in series, wherein the sequence unit includes a target sequence and a primer binding site; (b) hybridizing a primer to the primer binding site in a sequence unit of the antisense strand in the cluster; (c) extending the primer along the antisense strand to determine the sequence from at least a portion of the target sequence in the antisense strand; (d) removing the antisense strand from the cluster; (e) hybridizing a second primer to the primer binding site in a sequence unit of the sense strand after the removing of the antisense strand; and (f) extending the second primer along the sense strand to determine the sequence from at least a portion of the target sequence in the sense strand.

Alternatively, the present disclosure provides a method for determining sequences from sense and antisense strands of a nucleic acid. The method can include steps of (a) providing a nucleic acid cluster attached to a solid support, wherein the nucleic acid cluster includes a sense strand of a concatemer and an antisense strand of the concatemer, wherein the concatemer includes multiple copies of a sequence unit linked in series, wherein the sequence unit includes a target sequence and a primer binding site; (b) hybridizing a primer to the primer binding site in a sequence unit of the antisense strand in the cluster; (c) extending the primer along the antisense strand to determine the sequence from at least a portion of the target sequence in the antisense strand; (d) hybridizing a second primer to the primer binding site in a sequence unit of the sense strand; and (e) extending the second primer along the sense strand to determine the sequence from at least a portion of the target sequence in the sense strand, wherein steps (d) and (e) are performed while the antisense strand is present in the cluster. It will be understood that steps (d) and (e) can be performed prior to, or after, steps (b) and (c), as desired.

The present disclosure provides methods for sequencing one strand of a double stranded nucleic acid in the presence of another strand of the double stranded nucleic acid. In some configurations, sequencing will involve extending a first primer along one strand of the double stranded nucleic acid in the presence of a second primer that is hybridized to the other strand. A blocking moiety or capping moiety can be added to the second primer, thereby allowing the first primer to be selectively extended in the presence of the second primer. An example is provided in the diagrams of FIG. 2A and FIG. 2B. The starting point for the method, as shown in FIG. 2A, is a cluster having a concatemer sense strand (indicated as a black line having primer binding sites indicated by open and lined rectangles) and antisense strands of the concatemer (indicated as grey lines having primer binding sites indicated by open and lined rectangles). The multiple antisense strands present on a sense strand are referred to herein as antisense strand scales. Extendable 3' ends in the cluster, such as the 3' ends of the antisense strands (indicated by arrows on the grey lines) can optionally be modified with a blocking moiety or capping moiety. Then a first set of sequencing primers (indicated as open arrows) and nucleotides (indicated as grey diamonds) can be used to sequence the antisense strands. Continuing to FIG. 2B, the extended primers can then be modified with a blocking moiety or capping moiety. Then a second set of sequencing primers (indicated as lined arrows) and nucleotides (indicated as black diamonds) can be used to sequence the sense strand. The sequencing of the sense strand can be carried out in the presence of the extension products from the sequencing of the antisense strands because the extension products have been blocked or capped to prevent the extension products from producing background signal during the sequencing of the sense strand.

It will be understood that a nucleic acid cluster can have any of a variety of 3' ends that may be undesirably extended under conditions intended to extend a primer of interest. Such 3' ends may be present not only on the second primer but at the ends of the sense strand(s) or antisense strand(s) in the cluster. The presence of unwanted 3' ends in a cluster, can produce background signals arising from extension of these 3' ends and these background signals can hinder the ability to resolve desired signals arising from sequencing-based extension of the first primer. As shown by the first step in FIG. 2A, such artifacts can be avoided in a method set forth herein by modifying these 3' ends to incorporate a blocking moiety that prevents polymerase extension of the modified 3' end or to incorporate a capping moiety that inhibits formation of a ternary complex at the modified 3' end.

In another example, an array site can contain sense and antisense strands and one of the strands can be capped such that the other strand can be selectively sequenced without background interference from the capped strand. Selective primer capping can be used for sequencing paired regions of a larger nucleic acid molecule in order to determine structural relationships between the two regions in a genome. Selective primer capping can also allow for separate sequencing of a target sequence and an associated tag sequence. Exemplary tags include, but are not limited to, nucleic acid sequences that are appended to a target sequence to identify the source of the target sequence (a particular tag sequence is uniquely appended to target nucleic acids harvested from a particular cell, tissue or other sample). A tag can also be used to distinguish errors introduced during sample extraction and preparation procedures from biologically (e.g. clinically) interesting mutations or polymorphisms. Such tags are often referred to as unique molecular identifiers (UMIs).

A blocking moiety can be added to a primer or other nucleic acid in any of a variety of ways set forth herein. For example, a nucleotide having a blocking moiety can be added to the 3' end of the primer or other nucleic acid via polymerase catalysis. Alternatively, a primer can be chemically modified to incorporate a blocking moiety prior to being hybridized to a nucleic acid molecule or cluster. Exemplary methods for blocking a 3' end are set forth herein in regard to blocking and deblocking steps of a CRT sequencing process. In some embodiments, a primer or other nucleic acid can be modified with a reversible terminator moiety. In such configurations, the reversible terminator can be removed or modified to deblock the primer or other nucleic acid for subsequent extension.

A capping moiety can be added to a primer or other nucleic acid in any of a variety of ways set forth herein. For example, a capping moiety can be added to a primer prior to hybridizing the primer to a template. In another example, the capping moiety can be added via a synthetic technique. Alternatively, a primer can be hybridized to a template and the primer can be subsequently modified to contain a capping moiety. Optionally, the primer can be extended to incorporate a nucleotide that contains a ligand and the ligand can then be bound to a receptor that acts as an inhibitor of ternary complex formation. Useful reagents and methods for capping nucleic acids are set forth in US Pat. App. Pub. No. 2019/0367974 A1, which is incorporated herein by reference.

In another example, a primer can have a chemically modifiable moiety that is reactive with another reagent to form a capping moiety. The primer can have the chemically modifiable moiety prior to being hybridized to a template, or alternatively, after hybridizing the primer to the template, the primer can be extended to incorporate a nucleotide that has the chemically modifiable moiety. Subsequently, the chemically modifiable moiety can be covalently reacted to attach a ternary complex inhibitor to the primer. Suitable chemically modifiable moieties can include a functional group such as an amino group, carboxy group, maleimide group, oxo group or thiol group. Functional groups exemplified herein in the context of attaching nucleic acids to solid supports, such as click chemistry can also be useful.

A method of the present disclosure can include a primer modification process, whereby a nucleotide or other moiety is added to the primer. The primer modification process can be used to prepare the primer-template nucleic acid hybrid for a sequencing process or for an examination process that is used during a nucleic acid analysis, such as a sequencing analysis. For example, the primer modification can add a reversible terminator moiety to 3' ends of nucleic acids in order to prevent the nucleic acids from being extended in an amplification or sequencing process. Alternatively or additionally, the primer modification can add a cap moiety to the nucleic acid in order to prevent formation of a ternary complex at the 3' end of the nucleic acid.

Accordingly, the present disclosure provides a method for determining sequences from sense and antisense strands of a nucleic acid. The method can include steps of (a) providing a nucleic acid cluster attached to a solid support, wherein the nucleic acid cluster includes a sense strand of a concatemer and an antisense strand of the concatemer, wherein the concatemer includes multiple copies of a sequence unit linked in series, wherein the sequence unit includes a target sequence and a primer binding site; (b) hybridizing a primer to the primer binding site in a sequence unit of the antisense strand in the cluster; (c) extending the primer along the antisense strand to determine the sequence from at least a portion of the target sequence in the antisense strand; (d) adding a blocking moiety or a capping moiety to the extended primer; (e) hybridizing a second primer to the primer binding site in a sequence unit of the sense strand; and (f) extending the second primer along the sense strand to determine the sequence from at least a portion of the target sequence in the sense strand, wherein the blocking moiety prevents further extension of the extended primer or wherein the capping moiety prevents polymerase from binding the 3' end of the extended primer.

The present disclosure also provides a method for determining sequences from sense and antisense strands of a nucleic acid that includes steps of (a) providing a nucleic acid cluster attached to a solid support, wherein the nucleic acid cluster includes a sense strand of a concatemer and an antisense strand of the concatemer, wherein the concatemer includes multiple copies of a sequence unit linked in series, wherein the sequence unit includes a target sequence and a primer binding site; (b) adding blocking moieties or capping moieties to 3' ends in the nucleic acid cluster attached to the solid support; (c) hybridizing a primer to the primer binding site in a sequence unit of the antisense strand in the cluster; (d) extending the primer along the antisense strand to determine the sequence from at least a portion of the target sequence in the antisense strand; (e) hybridizing a second primer to the primer binding site in a sequence unit of the sense strand; and (f) extending the second primer along the sense strand to determine the sequence from at least a portion of the target sequence in the sense strand. Optionally, the method can further include, prior to step (d), adding a blocking moiety to the extended primer, thereby preventing further extension of the extended primer during step (f). As an alternative or additional option, the method can further include, prior to step (d), adding a capping moiety to the extended primer, thereby preventing polymerase from binding the 3' end of the extended primer during step (f).

A particularly useful capping chemistry will be selective for the 3' end of primers or other nucleic acids. The capping chemistry can be selective for the oxygen or hydroxyl moiety at the 3' end of a nucleic acid. For example, capping chemistry can be reactive to the 3' end of non-blocked primers and inert to modifying blocked primers. Chemistry that uses enzymes that are specific for native 3' ends of primers are particularly useful, including for example, ligases and polymerases. A capping procedure that is more efficient at modifying native 3' primer ends, as compared to blocked primers is beneficial for many applications.

In particular embodiments, a ternary complex inhibitor is used to cap a primer. Any of a variety of moieties can be added to a primer to hinder or prevent subsequent formation of ternary complex at the 3' end of the primer. Optionally, a primer can be attached to an oligonucleotide moiety as a result of ligase catalyzed attachment of the 5' end of the oligonucleotide to the 3' end of the primer or as a result of polymerase catalyzed extension of the primer with a series of nucleotides. Ligases, polymerases and other enzymes that modify primers can be useful. However, chemical techniques can also be useful for modifying a primer in a method set forth herein. An oligonucleotide moiety that is attached to a primer can include one or more non-natural nucleotide analogs. These analogs can be selected for their ability to form base pairs with the template, but analogs that do not pair with the template can also be used. Similarly, natural nucleotides can be present at one or more positions in the oligonucleotide moiety that form a mismatch that disrupts base pairing between the oligonucleotide and template. A particularly useful position for a mismatch or non-natural nucleotide analog is at or near the 3' end of the oligonucleotide moiety where it can function to inhibit subsequent ternary complex formation.

Another example of a useful moiety that can be added to a primer to hinder or prevent subsequent formation of ternary complex at the 3' end of the primer is a single nucleotide (e.g. a natural nucleotide or non-natural nucleotide analog). For example, a mismatched nucleotide can be attached to the 3' end of the primer to prevent ternary complex formation. Particularly useful mismatches and polymerases that are affected in their ability to recognize the mismatches are set forth in Kwok et al., *Nucleic Acids Res.* 18(4): 999-1005 (1990), which is incorporated herein by reference. A mismatched nucleotide can be present at the 3' end of a primer, having been introduced via an oligonucleotide moiety that was added to a primer. In some embodiments, a series of two or more mismatched nucleotides can be present at or near the 3' end of a primer to achieve inhibition of ternary complex formation.

Whether or not a nucleotide that is added to the 3' end of a primer is matched with the template, the nucleotide can include an exogenous moiety that functions as a ternary complex inhibitor. The exogenous moiety can have a steric blocking effect, whereby polymerase, nucleotide or both are blocked from forming ternary complex. The moiety can have other effects on ternary complex formation including, but not limited to, charge repulsion of the polymerase or cognate nucleotide, perturbation of the structure of the primer-template nucleic acid hybrid, polarity that repels the polymerase or cognate nucleotide, or the like. The exogenous moiety can be attached to a nucleotide, for example to the nucleotide that is at the 3' end of a primer, via a linker. A particularly useful linker has a relatively short length such that ternary complex inhibition occurs proximal to the 3' end of the primer. For example, a linker can have a length from a single covalent bond up to 2, 5, 10 or 15 covalent bonds. Alternatively or additionally, the linker can have a length that is shorter than 20, 15, 10 or 5 covalent bonds. Accordingly, a linker can maintain distance between the attachment point on the nucleotide and the attachment point on the ternary complex inhibitor of at most, for example, 25 Å (Angstroms), 20 Å, 15 Å, 10 Å, 5 Å, 2 Å or less. Relative lack of flexibility can be a useful characteristic for a linker, again, so that the inhibitor moiety will be proximal to the 3' end of the primer. Accordingly, linkers having amides, esters, carbon-carbon double bonds, carbon-carbon triple bonds, ring structures and other rotationally constrained bond structures can be useful.

Particularly useful exogenous moieties that can be attached to a nucleotide include, but are not limited to, biotin or other ligands that can hinder or prevent ternary complex formation due to their presence at the 3' end or due to their interactions with avidin, streptavidin or other receptor that in turn prevents ternary complex formation. Exemplary biotin analogs that can be used include, but are not limited to, biotin carbonate 5 or biotin carbamate 6 (see Yamamoto *Chem Asian* 1 10:1071-1078 (2015), which is incorporated herein by reference), 2-iminobiotin, diaminobiotin, or desthiobiotin. Biotin analogs that bind reversibly to avidin or streptavidin can be particularly useful when a cap is to be removed under relatively gentle conditions that do not denature avidin or streptavidin. Peptides having affinity for streptavidin or avidin can also be useful such as peptides used in the SBP-tag system (see Keefe et al. *Protein Expression and Purification* 23:440-446 (2001), which is incorporated herein by reference).

Other ligand-receptor pairs that can be used to form a ternary complex inhibitor include, but are not limited to, an antibody (or functional fragment thereof such as a Fab or ScFv) and epitope; a carbohydrate and a lectin; or a nucleic acid (or analog thereof) and its complementary nucleic acid (or analog thereof). Any of a variety of functional antibody fragments can be used including, for example, monovalent species such as a Fab or scFv or other monovalent species or engineered variants thereof such as a F(ab')2, diabody, triabody, minibody or single domain antibody (see Holliger and Hudson, *Nat. Biotechnol.* 23:1126-1136 (2005), which is incorporated herein by reference). Another particularly useful class of ligand-receptor pairs are peptides that are typically used as purification tags when fused to recombinant proteins and their binding partners. Exemplary peptides include, but are not limited to, polyhistidine (a polypeptide sequence of 6 or more histidines) which binds to divalent cations such as $Ni^{2+}$, glutathione-S-transferase (GST) which binds to glutathione, myc-tag (e.g. polypeptide having the sequence: EQKLISEEDL (SEQ ID NO:1)) which binds to anti-myc antibodies (available from the Developmental Studies Hybridoma Bank at the University of Iowa); calmodulin binding peptide (CBP, e.g. polypeptide having the sequence KRRWKKNFIAVSAANRFKKISSSGAL (SEQ ID NO:2)) which binds to calmodulin; FLAG tag (e.g. having the peptide sequence: DYKDDDD (SEQ ID NO:3) or DYKDDDDK (SEQ ID NO:4) or DYKDDDK (SEQ ID NO:5)) which binds to an anti-FLAG antibody); or maltose binding protein which binds to amylose or maltose. It will be understood that when using the purification tag systems above, either the peptide or the molecule to which it binds can be covalently linked to a nucleotide or primer. Generally, it is preferred to attach the smaller partner to the nucleotide via linker and then bind it to the larger partner in order to form the ternary complex inhibitor.

An advantage of using a ligand-receptor as a capping moiety is that the ligand need not inhibit ternary complex formation until it becomes bound to a receptor. For example, a nucleotide that is attached to a ligand can bind to a polymerase and primer-template nucleic acid to form a ternary complex and the nucleotide can be incorporated in the primer to position the ligand at the 3' end of the primer. The receptor can then be bound to the ligand at the 3' end of the primer to inhibit formation of a ternary complex at the 3' end of the primer.

A blocked nucleotide that is added to a primer in a method set forth herein need not have an exogenous label. This is because the extended primer need not be detected in a method set forth herein. However, if desired, one or more types of reversibly terminated nucleotides used in a method set forth herein can be detected, for example, via exogenous labels attached to the nucleotides. Exemplary reversible terminator moieties, methods for incorporating them into primers and methods for modifying the primers for further extension (often referred to as 'deblocking') are set forth elsewhere herein and in references cited herein.

Similarly, a ternary complex inhibitor, or other primer cap that is added to a primer in a method set forth herein, need not have an exogenous label. This is because a primer-template nucleic acid hybrid that includes a capping moiety need not be detected in a method set forth herein. However, if desired, one or more types of capping moieties used in a method set forth herein, can be detected, for example, via exogenous labels attached to the cap or ternary complex inhibitor.

The present disclosure provides methods for sequencing a nucleic acid strand in the presence of another nucleic acid strand, then removing the strand that was sequenced, and then sequencing the other strand. Examples are provided in the diagrams of FIG. 2A, FIG. 2C, and FIG. 2D. The starting point for the method, as shown in FIG. 2A, is a cluster having a concatemer sense strand (indicated as a black line having primer binding sites indicated by open and lined rectangles) and antisense strands of the concatemer (indicated as grey lines having primer binding sites indicated by open and lined rectangles). Extendable 3' ends in the cluster, such as the 3' ends of the antisense strands (indicated by arrows on the grey lines) can optionally be modified with a blocking moiety or capping moiety. Then a first set of sequencing primers (indicated as open arrows) and nucleotides (indicated as grey diamonds) can be used to sequence the antisense strands. Continuing to FIG. 2C, the antisense strands and the extended primers can then be removed from the cluster, for example by denaturation, degradation or other methods. Referring to FIG. 2D, the antisense strands and the extended primers can then be removed from the cluster by enzymatic digestion. For example, the antisense strands can include bases that are uracil (indicated by "stars" in the antisense strand) as described with reference to FIG. 1E. Uracil DNA glycosylase (UDG) can be used to catalyze the excision of uracil bases in the antisense strands, forming abasic (apyrimidinic) sites while leaving the phosphodiester backbones of the antisense strands intact. The lyase activity of Endonuclease VIII can then be used to break the phosphodiester backbones at the 3' and 5' sides of the abasics sites so that the remaining base-free deoxyribose moieties at the abasic sites are released, resulting in nicks in the antisense strands. A nuclease that digests double stranded DNA can then be used to digest away the remaining antisense strands and the extended primers. For example, an exonuclease (such as T7 Exonuclease) that is double-stranded specific and has 5' to 3' exonuclease activity can be used to digest the remaining antisense strands and the extended primers from the 5' termini (the 5' termini of the antisense strands and the extended primers, and the 5' termini at nicks of the antisense strands). Although the present application describes that the MDA reaction can be carried out in the presence of dUTP (or analogues thereof) with reference to FIG. 1E such that the antisense strands generated include uracil bases, this is for illustration only and is not intended to be limiting. For example, the MDA reaction can be carried out in the presence of deoxyribonucleotide triphosphate with a modified base or a non-canonical base such that the antisense strands generated include one or more bases that are modified or non-canonical. Such modified bases or non-canonical bases can target the antisense strands for degradation, such as enzymatic digestion as described with reference to FIG. 2D. As another example, the MDA reaction can be carried out in the presence of modified or non-canonical deoxyribonucleotide triphosphate (e.g., deoxyribose pseudouridine triphosphate) such that the antisense strands generated include one or more nucleotides that are modified or non-canonical (e.g., deoxyribose pseudouridine monophosphate). Such modified nucleotide or non-canonical nucleotides can target the antisense strands for degradation, such as enzymatic digestion as described with reference to FIG. 2D.

With reference to FIGS. 2C and 2D, then a second set of sequencing primers (indicated as lined arrows) and nucleotides (indicated as black diamonds) can be used to sequence the sense strand. The sequencing of the sense strand can be carried out in the absence of the antisense strands and extension products from the sequencing of the antisense strands.

Figure 3B:
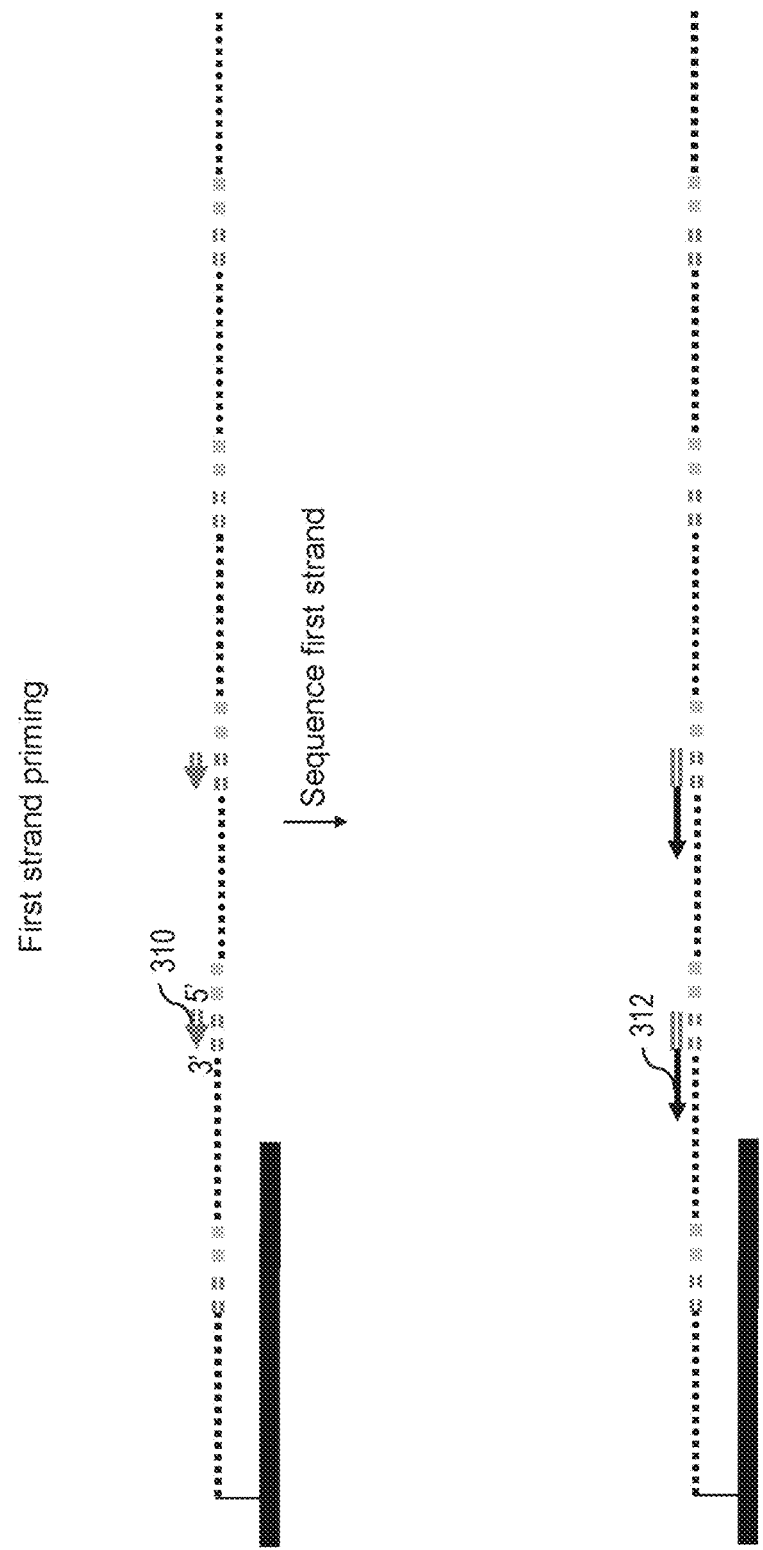

FIGS. 3A-3F provide diagrammatic representations of methods for determining sequences from first and second strands of a nucleic acid. In FIGS. 3A-3F, the first strands are illustrated as dotted lines, and the second strands are illustrated as solid lines. As shown in FIG. 3A, a nucleic acid capture primer 302 is attached to a solid support 304 via a linker. The primer can be used to capture a target nucleic acid 306 via a primer binding site 306A, 306P that is complementary to the primer. In one configuration shown in FIG. 3A, the immobilized primer can hybridize to portions of the primer binding site 306A, 306P that are present at opposite ends of a target sequence 306T. The immobilized primer thus functions as a splint that brings together the two ends of the target nucleic acid. The two ends can be ligated while hybridized to a splint nucleic acid to form a circular version 306c of the target nucleic acid. A single strand 308 is being produced via isothermal amplification, such as rolling circle amplification, of a primed circular template that is hybridized to an immobilized primer by a polymerase, such as Phi29. The single strand being synthesized can be a concatemer. The single strand concatemer being synthesized from the nucleic acid primer can be referred to herein as a first strand of a concatemer (or a sense strand of a concatemer). The single strand can contain multiple copies of the circular template and is a concatemer of sequence units. The first strand can be generated from the nucleic acid template without polymerase chain reaction. The primer and the single strand synthesized are shown as dotted lines in FIG. 3A. In FIG. 3A, two copies of the circular template (two sequence units) have already been produced and the circular template is hybridized to a portion of a third copy (third sequence unit) that is being replicated. FIG. 3B shows the final product of the RCA reaction with the circular template being absent. The final product of the RCA reaction may not be hybridized to the circular template during subsequent steps of the method after the RCA reaction. In some embodiments, the final product of the RCA reaction is hybridized to the circular template during one or more subsequent steps of the method after the RCA reaction.

Figure 3C:
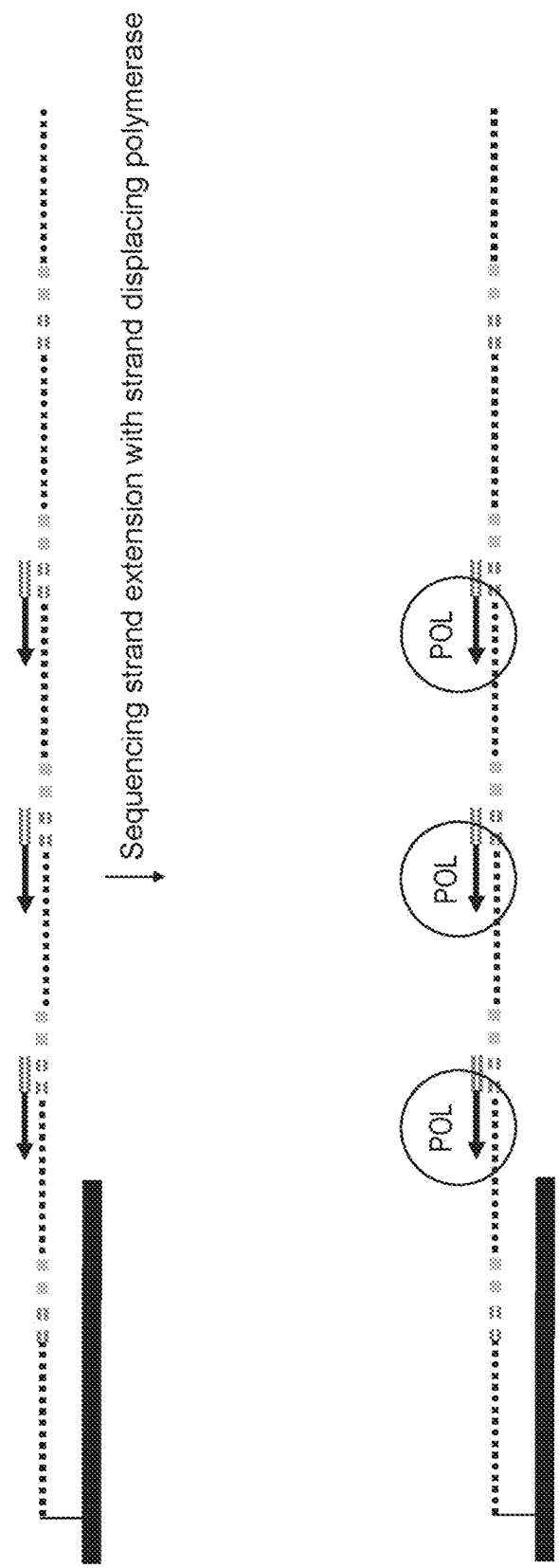
Figure 3D:
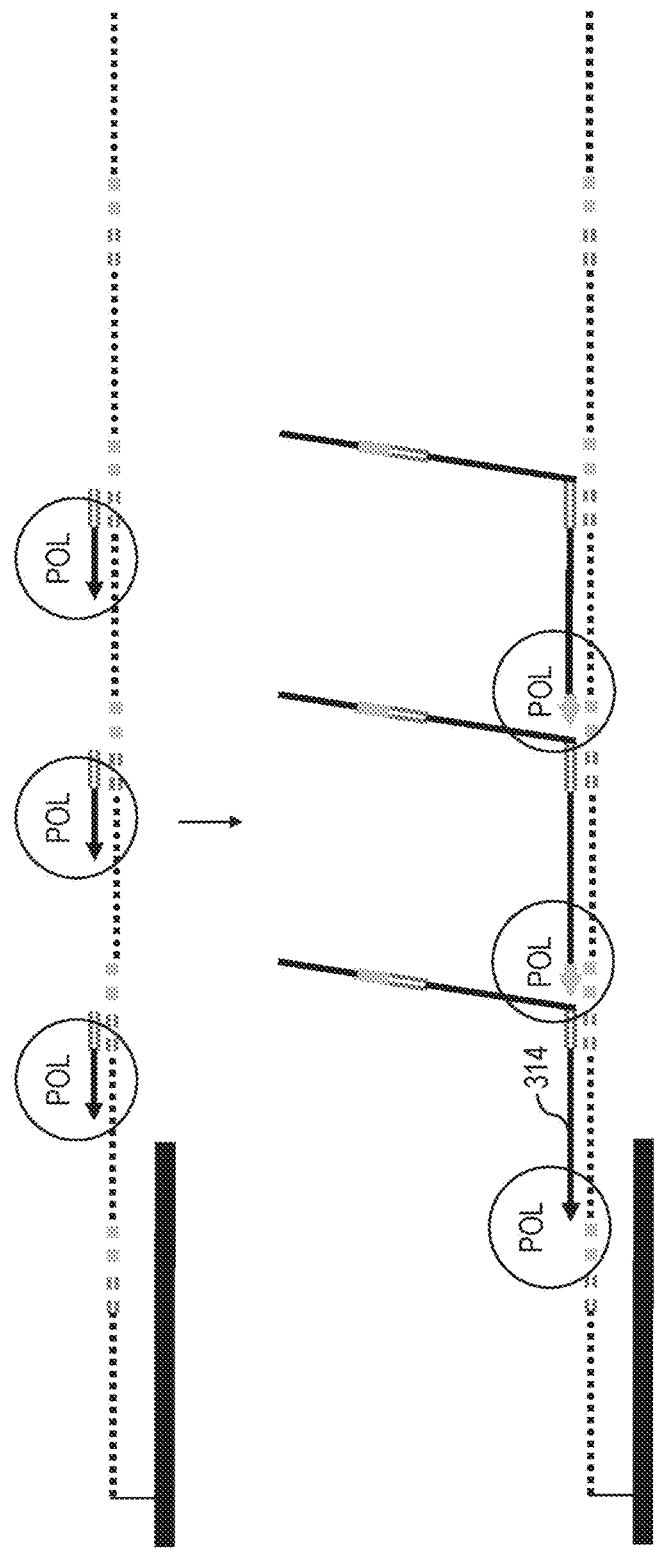

Referring to FIGS. 3B-3D, the step of determining the sequence of the first strand using a sequencing primer 310 and the step of synthesizing a second strand (e.g., an antisense strand) using an amplification primer can occur simultaneously. For example, a sequencing primer can prime the first strand. The sequencing primer can be extended to generate an extension product 312 to determine the sequence of the first strand using, for example, a polymerase (not shown). Any sequencing method of the present disclosure, such as SBB™ or SBS, can be used to determine the sequence of the first strand and generate the second strand. The extension product of the sequencing primer used to determine the sequence of the first strand can be further extended with MDA to generate a second strand 314 of the concatemer (See FIG. 3D for an example). A polymerase, such as a polymerase with strand displacement activity, can be used to further extend the sequencing extension product with MDA to generate the second strand. The second strand synthesized includes the extension product from sequencing the first strand using a sequencing primer. The sequencing primers, the extension products of the sequencing primers, and the second strands generated are shown as solid lines in the figures. The number of sequencing primers bound to the first strand, the number of extension products of the sequencing primers, and the number of second strands generated shown in the figures are for illustration only and not intended to be limiting. The multiple second strands generated by further extending the extension products of the sequencing primers appear as scales in FIGS. 3D-FIG. 3F) and are referred to herein as second strand scales (or antisense strand scales).

Figure 3E:
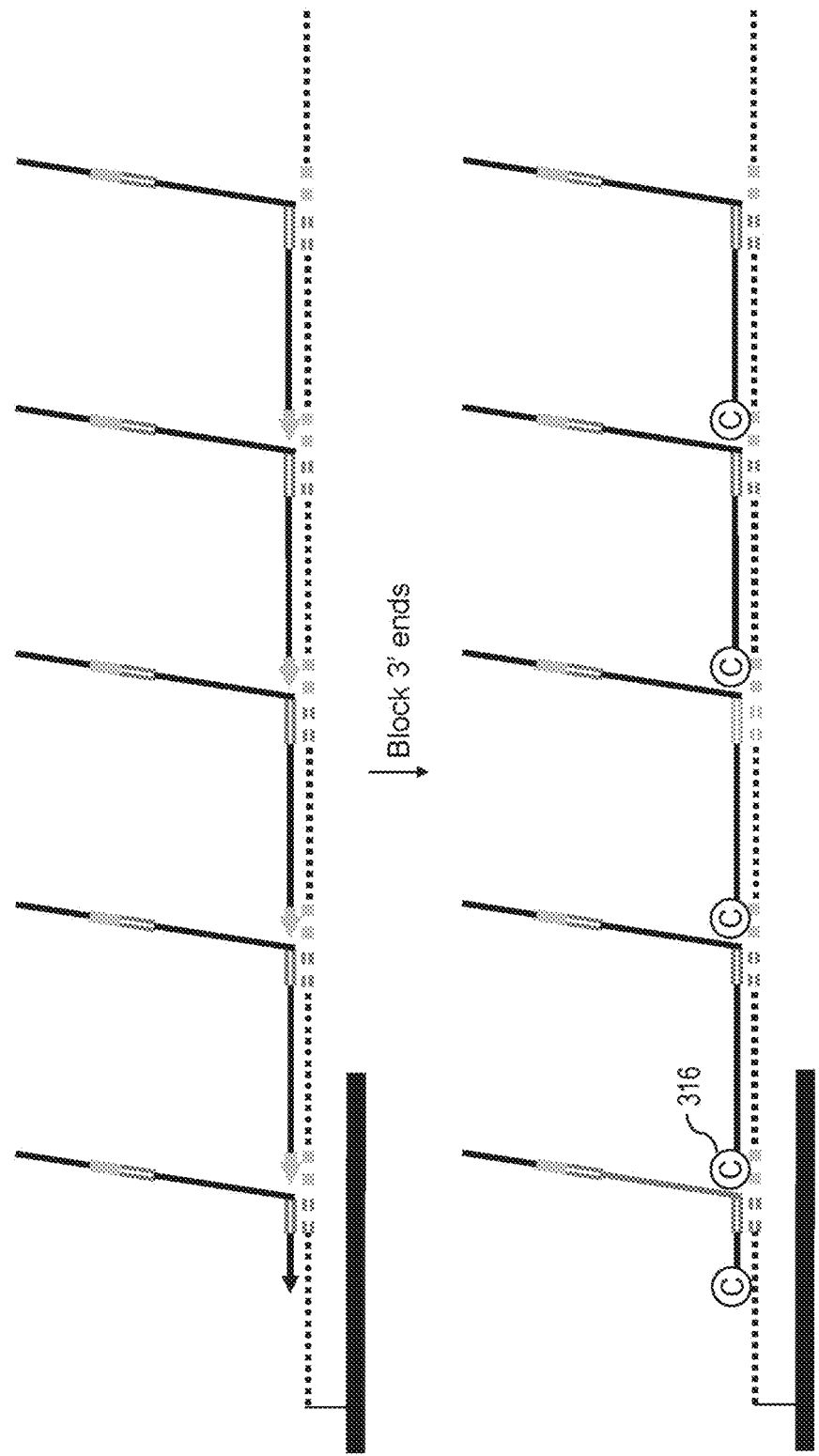

Referring to FIG. 3E, the 3' ends of the second strands can be capped by incorporating 3' blocking or capping moieties 316 to prevent further extension and/or to hinder or preclude ternary complex formation when sequencing the second strands. Numerous 3' blocking or capping moieties described elsewhere in the disclosure can be used. The second strands can be primed with sequencing primers 318 and sequenced by extending the sequencing primers to generate extended sequencing primers 320 illustrated in FIG. 3F.

FIGS. 4A-4F provide diagrammatic representations of methods for determining sequences from first and second strands of a nucleic acid with the first and second strands attached to the solid support. In FIGS. 4A-4F, the capture primers and the first strands are illustrated as dotted lines, and the target nucleic acid, the amplification primers, and the second strands are illustrated as solid lines. Corresponding regions are shown as double lines (e.g., binding sites 406AC for capture primers and binding sites 406AA for amplification primers, and the corresponding sequences on the capture primers and amplification primers) or single lines (e.g., the target sequence 406T and corresponding sequences on the first strands and the second strands, and the binding sites 406P' for the sequencing primer and corresponding sequences on the sequencing primers).

Figure 4B:
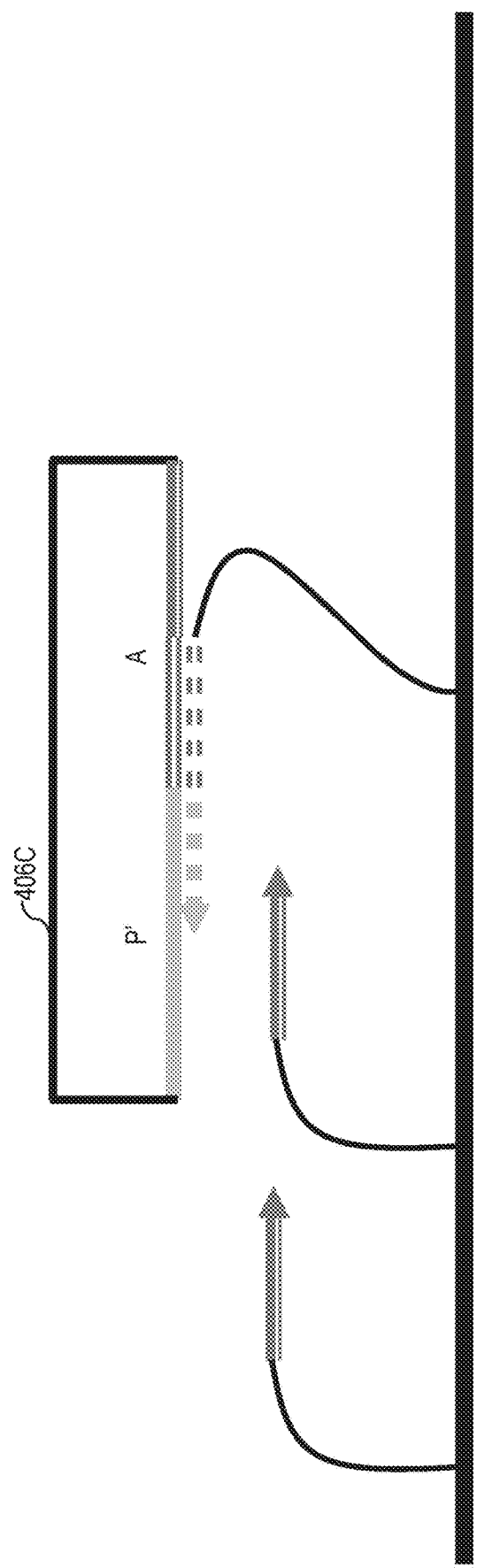
Figure 4C:
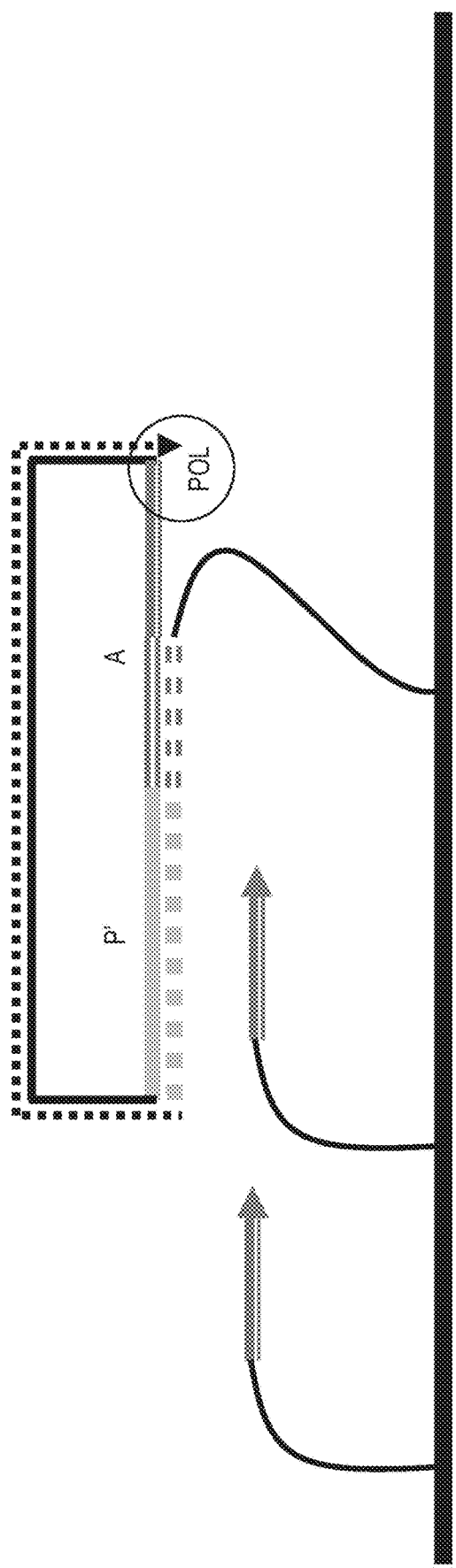
Figure 4D:
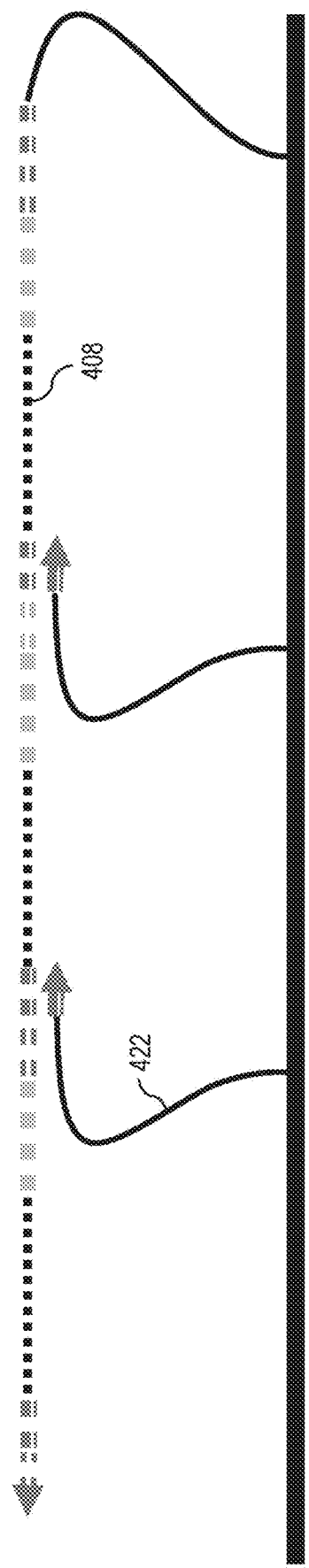

As shown in FIG. 4A, a nucleic acid capture primer 402 is attached to a solid support 404 via a linker, and a nucleic acid amplification primer 422 is attached to the solid support via a linker. The capture primer can be used to capture a target nucleic acid 406 via a primer binding site 406A, 406P' that is complementary to the capture primer. In one configuration shown in FIG. 4B, the immobilized capture primer can hybridize to portions of the primer binding site 406A, 406P' that are present at opposite ends of a target sequence 406T. The immobilized capture primer thus functions as a splint that brings together the two ends of the target nucleic acid. The two ends can be ligated using, for example T4 ligase, while hybridized to a splint nucleic acid to form a circular version 406c of the target nucleic acid. A kinase, such as T4 Polynucleotide Kinase, can phosphorylate the 5'-end of the target nucleic acid prior to ligation of the target nucleic acid to form a circular target nucleic acid. Referring to FIGS. 4C-4D, a single strand 408 is being produced via isothermal amplification, such as rolling circle amplification, of a primed circular template that is hybridized to an immobilized primer by a polymerase, such as Phi29. The single strand being synthesized can be a concatemer. The single strand being synthesized from the nucleic acid primer can be referred to herein as a first strand of a concatemer (or a sense strand of a concatemer). The single strand can contain multiple copies of the circular template and is a concatemer of sequence units. The first strand can be generated from the nucleic acid template without polymerase chain reaction. The primer and the single strand synthesized are shown as dotted lines in the figures. FIG. 4D shows three copies of the circular template (three sequence units) being produced for illustrative purpose only and is not intended to be limiting. FIG. 4D shows the final product of the RCA reaction after the circular template has been removed.

Figure 4E:
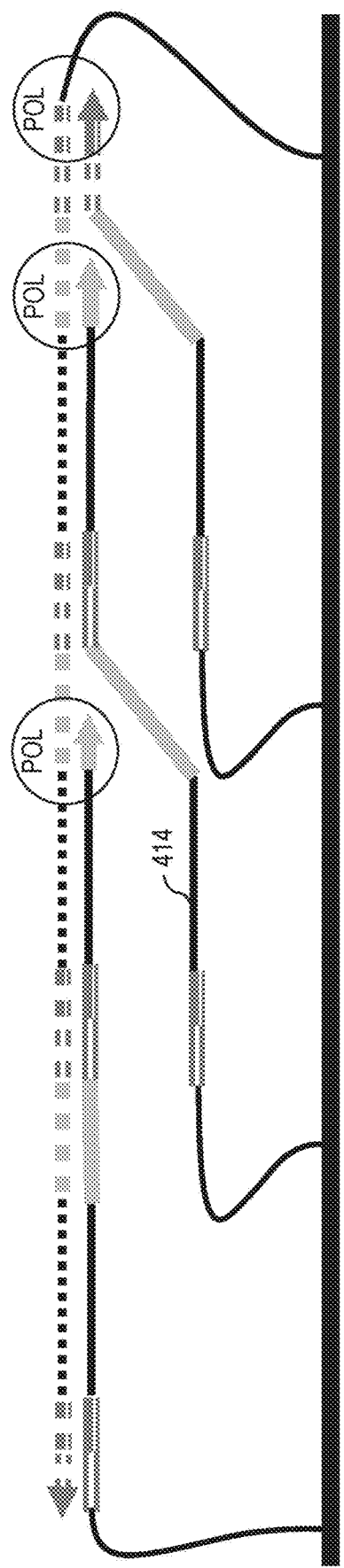

The methods illustrated in FIGS. 4A-4F can include the step of synthesizing a second strand (e.g., as an antisense strand) using an amplification primer attached to the solid support. Referring to FIG. 4D, an amplification primer 422 can prime the first strand 408. The amplification primer can be extended with MDA to generate a second strand 414 of the concatemer illustrated in FIG. 4E. The second strand of the concatemer can include one or more sequence units. FIG. 4E illustrates one second strand with one sequence unit generated and a second sequence unit starting to be generated. FIG. 4E illustrates another second strand with the generation of the second sequence unit nearly completed. A polymerase, such as a polymerase with strand displacement activity, can be used to generate the second strand, such as via MDA. The second strands generated are shown as solid lines in the figures. The multiple second strands generated appear as scales in FIG. 4E and are referred to herein as second strand scales (or antisense strand scales). In one configuration, the step of synthesizing a second strand using an amplification primer and the step of determining the sequence of the first strand using a sequencing primer can occur simultaneous as described with reference to FIGS. 3A-3F. In such configuration, the amplification primer is a sequencing primer.

Referring to the inset in FIG. 4A, the capture primer 402 that binds to the nucleic acid 406 can include a complementary sequence of a partial sequence of the primer binding site 406A. With RCA, the resulting first strand 408 can include the complementary sequence of the entire primer site 406A. The amplification primer 422 for generating multiple second strands from the first strand 408 can include a partial sequence of the primer binding site. The partial sequences of the primer binding site on the capture primer 402 and the amplification primer 422 may not overlap as illustrated in the inset in FIG. 4A. The primer binding site 406A is illustrated as having two regions, one region 406AC (shown as a double line having two lines with an equal thickness) that the capture primer 402 binds to, and another region 406AA (shown as a double line having two lines with unequal thicknesses) that the amplification primer 422 binds to.

Surface bound oligos may anneal to the adapter site of the first strand concatemer. Alternately, in some cases the surface bound oligos anneal to adjacent or otherwise distinct regions of the first strand concatemer. These regions are often derived from the original library adapter 5' or 3' ends, though oligos targeting internal regions of the original library or of the concatemer derived therefrom are also contemplated.

Figure 4F:
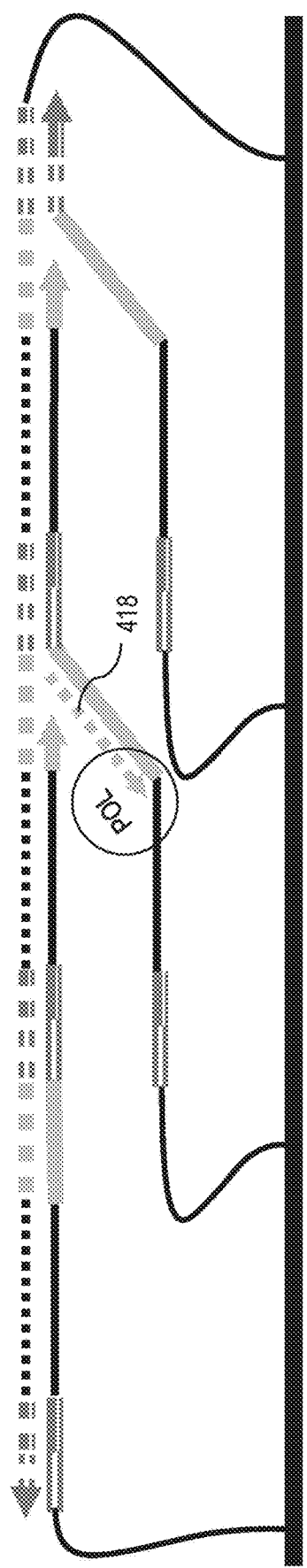

Referring to FIG. 4F, the second strands can be primed and sequenced using a sequencing primer 418. In one configuration, the 3' ends of the second strands can be capped by incorporating 3' blocking or capping moieties to prevent further extension of the 3' ends of the second strands and/or to hinder or preclude ternary complex formation at 3' ends of the second strands. Numerous 3' blocking or capping moieties described elsewhere in the disclosure can be used. The second strands can be primed and sequenced before the first strands are primed or sequence. Alternatively, the second strands can be primed and sequenced after the first strands are primed or sequenced.

The solid support can include two (or more, such as three, four, five, six, seven, eight, nine, ten, or more) types or populations of primers. The two or more types of primers can be, for example, as multiple capture primers and multiple amplification primers. Alternatively or additionally, the types of primers can include multiple capture primers and multiple sequencing primers for sequencing, for example, the first strands generated by extending the capture primers). The density of one type or population of primers (e.g., capture primers) on the solid support can be higher than the density of another type or population of primers (e.g., amplification primers) on the solid support. The density of one type or population of primers on the solid support can be the same as the density of another type or population of primers on the solid support. The density of a type or population of primers (or all primers) can very. The density of a type or population of primers (or all primers) on a solid support can be, be about, be at least, be at least about, be at most, or be at most about, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$ $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, $1\times10^{16}$, $2\times10^{16}$, $3\times10^{16}$, $4\times10^{16}$, $5\times10^{16}$, $6\times10^{16}$, $7\times10^{16}$, $8\times10^{16}$, $9\times10^{16}$, or a number or a range between any two of these values, primers per m².

Various separation distances or average separation distances between two adjacent primers of the same type or population (or of two different types or populations) are contemplated herein. The separation distance or average separation distance between two adjacent primers of the same type or population (or of two different types or populations) can be, be about, be at least, be at least about, be at most, or be at most about, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, 1000 nm, or a number or a range between any two of these values.

Various ratios of the number of one type or population of primers and the numbers of another type or population of primers are contemplated by the present disclosure. The ratio of the number of one type or population of primers and the numbers of another type or population of primers can be, be about, be at least, be at least about, be at most, or be at most about, 1:100, 1:99, 1:98, 1:97, 1:96, 1:95, 1:94, 1:93, 1:92, 1:91, 1:90, 1:89, 1:88, 1:87, 1:86, 1:85, 1:84, 1:83, 1:82, 1:81, 1:80, 1:79, 1:78, 1:77, 1:76, 1:75, 1:74, 1:73, 1:72, 1:71, 1:70, 1:69, 1:68, 1:67, 1:66, 1:65, 1:64, 1:63, 1:62, 1:61, 1:60, 1:59, 1:58, 1:57, 1:56, 1:55, 1:54, 1:53, 1:52, 1:51, 1:50, 1:49, 1:48, 1:47, 1:46, 1:45, 1:44, 1:43, 1:42, 1:41, 1:40, 1:39, 1:38, 1:37, 1:36, 1:35, 1:34, 1:33, 1:32, 1:31, 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, or a number or a range between any two of these values.

Two neighboring primers (or any two neighboring primers) of a type or population are capable of coming into contact with each other. Two neighboring primers (or any two neighboring primers) of a type or population are incapable of coming into contact with each other. Two neighboring primers (or any two neighboring primers) of different types or populations are capable of coming into contact with each other. Two neighboring primers (or any two neighboring primers) of different types or populations are incapable of coming into contact with each other. The average distance between locations on the solid support two neighboring or closest capture primers are attached to can be greater than (or less than or equal to) the length of one of the two capture primers, lengths of the two capture primers, an average length of the two capture primers, or the total length of the two capture primers (or 0.1×, 0.2×, 0.3×, 0.4×, 0.5×, 0.6×, 0.7×, 08×, 0.9×, of the length). An average distance between locations on the solid support two neighboring or closest amplification primers of the plurality of amplification primers are attached to can be greater than (or less than or equal to) the length of one of the two amplification primers, lengths of the two amplification primers, an average length of the two amplification primers, or the total length of the two capture primers (or 0.1×, 0.2×, 0.3×, 0.4×, 0.5×, 0.6×, 0.7×, 08×, 0.9×, 1.1×, 1.2×, 1.3×, 1.4×, 1.5×, 1.6×, 1.7×, 1.8×, 1.9×, 2×, 3×, 4×, 5×, 6×, 7×, 8×, 9×, 10×) of any of the lengths).

Two primers (or each primer) of a type or population (e.g., the capture primers) can have an identical length. Two primers (or each primer) of a type or population (e.g., the capture primers) can have different lengths. The length of a primer (or two of more primers of a type or population, or each primer of a type or population) can be, be about, be at least, be at least about, be at most, be at most about, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 300, 400, 500, 600, 700, 800, 900, 1000, nucleotides in length. The length of a primer (or two of more primers of a type or population, or each primer of a type or population) can be, be about, be at least, be at least about, be at most, be at most about, 100 Å, 110 Å, 120 Å, 130 Å, 140 Å, 150 Å, 160 Å, 170 Å, 180 Å, 190 Å, 200 Å, 300 Å, 400 Å, 500 Å, 600 Å, 700 Å, 800 Å, 900 Å, 1000 Å, 0.2 µm, 0.3 µm, 0.4 µm, 0.5 µm, 0.6 µm, 0.7 µm, 0.8 µm, 0.9 µm, 1 µm, 2 µm, 3 µm, 4 µm, 5 µm, 6 µm, 7 µm, 8 µm, 9 µm, 10 µm, or a number or a range between any two of these values.

The ratio of the length of a primer of one type or population (e.g., a capture primer) and the length of a primer of the same type or population (e.g., a capture primer), or the ratio of the length of a primer of one type or population (e.g., a capture primer) and the length of a primer of another type or population (e.g., an amplification primer), can vary. The ratio of the lengths of two primers of one type or population, or the ratio of the length of two primers of different types or populations, can be, be about, be at least, be at least about, be at most, or be at most about, 1:100, 1:99, 1:98, 1:97, 1:96, 1:95, 1:94, 1:93, 1:92, 1:91, 1:90, 1:89, 1:88, 1:87, 1:86, 1:85, 1:84, 1:83, 1:82, 1:81, 1:80, 1:79, 1:78, 1:77, 1:76, 1:75, 1:74, 1:73, 1:72, 1:71, 1:70, 1:69, 1:68, 1:67, 1:66, 1:65, 1:64, 1:63, 1:62, 1:61, 1:60, 1:59, 1:58, 1:57, 1:56, 1:55, 1:54, 1:53, 1:52, 1:51, 1:50, 1:49, 1:48, 1:47, 1:46, 1:45, 1:44, 1:43, 1:42, 1:41, 1:40, 1:39, 1:38, 1:37, 1:36, 1:35, 1:34, 1:33, 1:32, 1:31, 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, or a number or a range between any two of these values.

Any of a variety of polymerases can be used in a method or apparatus set forth herein, for example, to replicate a nucleic acid template, form a stabilized ternary complex or to carry out primer modification. Polymerases that may be used include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that have the ability to catalyze a polymerization reaction. Optionally, the naturally occurring and/or modified variations thereof have the ability to catalyze a polymerization reaction in at least one condition that is not used during formation or examination of a stabilized ternary complex. Optionally, the naturally-occurring and/or modified variations that participate in stabilized ternary complexes have modified properties, for example, enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, reduced catalysis rates, catalytic inactivity etc. Mutant polymerases include, for example, polymerases wherein one or more amino acids are replaced with other amino acids, or insertions or deletions of one or more amino acids. Exemplary polymerase mutants that can be used to form a stabilized ternary complex include, for example, those set forth in U.S. patent application Ser. No. 15/866,353, published as US Pat. App. Pub. No. 2018/0155698 A1; US Pat. App. Pub. No. 2017/0314072 or U.S. patent application Ser. No. 16/567,476, each of which is incorporated herein by reference.

Modified polymerases include polymerases that contain an exogenous label moiety (e.g., an exogenous fluorophore), which can be used to detect the polymerase. Optionally, the label moiety can be attached after the polymerase has been at least partially purified using protein isolation techniques.

For example, the exogenous label moiety can be covalently linked to the polymerase using a free sulfhydryl or a free amine moiety of the polymerase. This can involve covalent linkage to the polymerase through the side chain of a cysteine residue, or through the free amino group of the N-terminus. An exogenous label moiety can also be attached to a polymerase via protein fusion. Exemplary label moieties that can be attached via protein fusion include, for example, green fluorescent protein (GFP), phycobiliproteins (e.g. phycocyanin and phycoerythrin) or wavelength-shifted variants of GFP or phycobiliproteins. In some embodiments, an exogenous label on a polymerase can function as a member of a FRET pair. The other member of the FRET pair can be an exogenous label that is attached to a nucleotide that binds to the polymerase in a stabilized ternary complex. As such, the stabilized ternary complex can be detected or identified via FRET.

Alternatively, a polymerase that participates in a stabilized ternary complex, or that is used to extend or modify a primer need not be attached to an exogenous label. For example, the polymerase need not be covalently attached to an exogenous label. Instead, the polymerase can lack any label until it associates with a labeled nucleotide and/or labeled nucleic acid (e.g. labeled primer and/or labeled template).

Different activities of polymerases can be exploited in a method set forth herein. A polymerase can be useful, for example, in a template amplification process, primer modification process such as a primer extension step or primer capping step, examination step or combination thereof. The different activities can follow from differences in the structure (e.g. via natural activities, mutations or chemical modifications). Nevertheless, polymerase can be obtained from a variety of known sources and applied in accordance with the teachings set forth herein and recognized activities of polymerases. Useful DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, €, η, ζ, λ,σ, μ, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated herein by reference.

Useful RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

Another useful type of polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some embodiments. Polymerases that substantially lack 3'-5' proofreading exonuclease activity are also useful in some embodiments, for example, in most genotyping and sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

A method for determining sequences from sense and antisense strands of a target nucleic acid can be performed to determine all or part of the target nucleic acid sequence. In some configurations, most or all of the full length of the sense and antisense strands are sequenced. As such, the sequences determined for the two strands will overlap fully or nearly fully. In some cases, the sequence that is determined from the antisense strand will be complementary to the full length of the sequence that is determined from the sense strand, and the sequence that is determined from the sense strand will be complementary to the full length of the sequence that is determined from the antisense strand. The more complete the overlap between the sequences determined from the two strands the more accurate the sequencing results since the two sequences can be compared to identify errors. In some cases, the sequence of one strand can be used to correct the sequence of the other strand. For example, if a discrepancy is found between the two strands, then the discrepancy can be resolved by discarding (or statistically downgrading) the call made in the strand having a sequence motif that is known to be error prone in the sequencing method.

In other configurations of a method for determining sequences from sense and antisense strands of a target nucleic acid, a first portion of the target sequence is determined from the antisense strand and a second portion of the target sequence is determined from the sense strand. Depending upon the length of the target sequence and the length of the two sequence reads, the first portion and second portions can overlap partially. Accordingly, the first portion is partially complementary to the second portion of the target sequence. In some cases, the sequence that is determined from the antisense strand can be complementary to the full length of the sequence that is determined from the sense strand. In some cases, the sequence that is determined from the sense strand can be complementary to the full length of the sequence that is determined from the antisense strand.

In some applications of the methods set forth herein, a gap can occur between the two portions when those portions are considered in an alignment with the full target sequence. The gap can be at least 1, 10, 100, 1000 or more bases in length. Alternatively or additionally, the gap can be at most 1000, 100, 10 or 1 bases in length. Knowledge that two sequences are oriented in opposite directions and knowledge of the size of the gap between the two sequences can be advantageous for alignment to a reference genome. Information pertaining to the relative orientation for the two sequences not only improves reconstruction of a genome by alignment to a reference genome, but the information also allows structural variations in a genome to be identified. A deviation in the expected genome alignment between two ends of a paired end read can indicate a structural variation for the sample being sequenced compared to the reference sequence to which the reads are aligned.

The present disclosure provides systems configured to carry out a method set forth herein. For example, a system can be configured to produce and detect ternary complexes formed between a polymerase and a primer-template nucleic acid hybrid in the presence of nucleotides to identify one or more bases in a template nucleic acid sequence. A system of the present disclosure can include a vessel, solid support or other apparatus for carrying out a nucleic acid amplification and/or detection method. For example, the system can include an array, flow cell, multi-well plate or other convenient apparatus. The apparatus can be removable, thereby allowing it to be placed into or removed from the system. As such, a system can be configured to process a plurality of apparatus (e.g. vessels or solid supports) sequentially or in parallel. The system can include a fluidic component having reservoirs for containing one or more of the reagents set forth herein (e.g. polymerase, primer, template nucleic acid, nucleotide(s) for ternary complex formation, nucleotides for primer extension, deblocking reagents, ternary complex inhibitors, or mixtures of such components). The fluidic system can be configured to deliver reagents to a vessel or solid support, for example, via channels or droplet transfer apparatus (e.g. electrowetting apparatus). Any of a variety of detection apparatus can be configured to detect the vessel or solid support where reagents interact. Examples include luminescence detectors, surface plasmon resonance detectors and others known in the art. Exemplary systems having fluidic and detection components that can be readily modified for use in a system herein include, but are not limited to, those set forth in US Pat. App. Pub. No. 2018/0280975 A1, which claims priority to US Pat. App. Ser. No. 62/481,289; U.S. Pat. Nos. 8,241,573; 7,329,860 or 8,039,817; or US Pat. App. Pub. Nos. 2009/0272914 A1 or 2012/0270305 A1, each of which is incorporated herein by reference.

Optionally, a system of the present disclosure further includes a computing system, or components of a computing system. A computing system can include a computer processing unit (CPU) that is configured to operate system components. The CPU can include one or more processors or processing units. The same or different CPU can interact with the system to acquire, store and process signals (e.g. signals detected in a method set forth herein). In particular embodiments, a CPU can be used to determine, from the signals, the identity of the nucleotide that is present at a particular location in a template nucleic acid. In some cases, the CPU will identify a sequence of nucleotides for the template from the signals that are detected.

A computing system can be a personal computer system, server computer system, thin client, thick client, hand-held or laptop device, multiprocessor system, microprocessor-based system, set top box, programmable consumer electronic, network PC, minicomputer system, mainframe computer system, smart phone, and distributed cloud computing environments that include any of the above systems or devices, and the like. The computing system can include a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The computing system may also include a variety of computer system readable media. Such media may be any available media that is accessible by a cloud computing environment, such as volatile and non-volatile media, and removable and non-removable media.

The memory architecture may include at least one program product having at least one program module implemented as executable instructions that are configured to carry out one or more steps of a method set forth herein. For example, executable instructions may include an operating system, one or more application programs, other program modules, and program data. Generally, program modules may include routines, programs, objects, components, logic, data structures, and so on, that perform particular tasks set forth herein.

The components of a CPU may be coupled by an internal bus that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A CPU can optionally communicate with one or more external devices such as a keyboard, a pointing device (e.g. a mouse), a display, such as a graphical user interface (GUI), or other device that facilitates interaction of a use with the nucleic acid detection system. Similarly, the CPU can communicate with other devices (e.g., via network card, modem, etc.). Such communication can occur via I/O interfaces. Still yet, a CPU of a system herein may communicate with one or more networks such as a local area network (LAN), a general wide area network (WAN), and/or a public network (e.g., the Internet) via a suitable network adapter.

EXAMPLE I

Paired End Sequencing Via Two 22 Cycle Runs
(PE 2×22)

This example describes a simultaneous RCA and MDA method for making clusters having sense and antisense strands as described herein with reference to FIG. 1D. This example demonstrates sequencing of both strands in a paired end sequencing approach. Moreover, this example demonstrates that both strands could be sequenced without the need for removing one strand to sequence the other.
Materials and Methods Flow cells containing primed template nucleic acids were prepared as follows. A lawn of SHARK248 primers (5'-CGCCGTATCATTCAAGCAGAAGAC*G*G-3', where the asterisk denotes a phosphorothiate bond; SEQ ID NO: 6) was attached to the inner surface of the flow cell by click chemistry. Template rings were hybridized to the SHARK248 primers via a universal adapter that was complementary to the SHARK248 primers and the primers were extended using a Phi29 DNA polymerase (Thermo Fisher Waltham, Mass.) Scientific mix containing 33 mM Tris-HCl pH 8.0 (Sigma-Aldrich, St. Louis, Mo.), 30 mM MgCl2 (Invitrogen, Carlsbad, Calif.), 10 mM DTT (Sigma-Aldrich, St. Louis, Mo.), 90 mM KCl (Teknova, Hollister, Calif.), 2% Sucrose (Sigma-Aldrich, St. Louis, Mo.), 0.5 M Betaine (Sigma-Aldrich, St. Louis, Mo.), 0.2% Tween-80 (Sigma-Aldrich, St. Louis, Mo.), 0.8 mM dNTPs (New England Biolabs, Ipswich, Mass.) and 0.1 µM scaling primer SHARK291 (5'-ATCTCGTATGCCGTCTTCTGCTT*G-3', where the asterisk denotes a phosphorothiate bond; SEQ ID NO: 7). The RCA/MDA reaction occured for 4.5 hours at 37° C. with Phi29 DNA polymerase being replenished every 15 minutes. After extension, Phi29 was removed by heat denaturation and washed in buffer containing 40 mM Tris-HCl pH 8.0, 110 mM KCl, 0.02 mM EDTA (Sigma-Aldrich, St. Louis, Mo.) and 0.1% Tween-80.

The clusters produced by the above method were then treated to add a capping moiety to any extendable 3' ends in the cluster. A capping reagent was prepared to include 50 mM Tricine (Sigma-Aldrich, St. Louis, Mo.), 2 µM of each of the four biotinylated dideoxy nucleotides shown in FIG. 5 of US Pat. App. Pub. No. 2020/0032322 A1 (which is incorporated herein by reference), 0.1 mM Biotin (Sigma-Aldrich, St. Louis, Mo.), 50 mM KCl (Teknova, Hollister, Calif.), 0.1% Tween-80 (Sigma-Aldrich, St. Louis, Mo.), 5 mM MgCl$_2$ (Invitrogen, Carlsbad, Calif.), 40 U/ml M15 DNA Polymerase (see U.S. patent application Ser. No. 16/567,476, which is incorporated herein by reference), and 0.1 mM EDTA (Invitrogen, Carlsbad, Calif.). The capping reagent was introduced to the flow cell and the capping reaction was allowed to proceed for 2 minutes at 55° C. The capping reagent was removed, and the flow cell was washed with high salt to remove any bound DNA polymerase. The next step in the capping process was incubation of the biotinylated primer extension product with streptavidin. The streptavidin mixture included 50 mM Tricine (Sigma-Aldrich, St. Louis, Mo.), 0.076 mg/ml Streptavidin (New England Biolabs, Ipswich, Mass.), 50 mM KCl (Teknova, Hollister, Calif.), 0.1% Tween-80 (Sigma-Aldrich, St. Louis, Mo.), 5 mM MgCl$_2$ (Invitrogen, Carlsbad, Calif.), and 0.1 mM EDTA (Invitrogen, Carlsbad, Calif.). The streptavidin mixture was introduced to the flow cell and binding was allowed to proceed for 2 minutes at 55° C. The clusters were treated with formamide to denature any double strand regions prior to the following sequencing steps.

A plurality of SHARK231 primers (5'- GTGACTG-GAGTTCAGACGTGTGCTCTTC-3'; SEQ ID NO: 8) were hybridized to complementary primer binding sites in the adapter regions of the antisense strands in the clusters. The antisense strands of the clusters were sequenced using a Sequencing By Binding™ (SBB™) method that was performed cyclically, where each cycle included steps for (i) extension: adding a reversibly terminated nucleotide to the primers of the immobilized primer-template hybrids, (ii) examination: forming and detecting stabilized ternary complexes on the reversibly terminated, immobilized primer-template hybrids, and (iii) activation: cleaving the reversible terminator from the extended primers. Each cycle resulted in addition of a single nucleotide and detection of a subsequent nucleotide position.

The sequencing cycle was initiated by incorporating reversible terminator nucleotides at the 3'-ends of the primers of the immobilized primer-template hybrids. This was accomplished by an extension step in which the flow cell was contacted with unlabeled reversibly terminated nucleotide analogs of dATP, dGTP, dCTP, and dTTP) in the presence of M15 polymerase (described in U.S. patent application Ser. No. 16/567,476, which is incorporated herein by reference). The reversible terminator nucleotide used in this illustrative procedure included a 3'-ONH$_2$ reversible terminator moiety. A description of this reversible terminator nucleotide can be found in U.S. Pat. No. 7,544,794, which is incorporated herein by reference.

Next, a wash step was carried out to remove the dNTPs from the flow cell. The wash solution contained isopropanol, Tween-80, hydroxylamine and EDTA. The wash step retained the M15 polymerase (described in U.S. patent application Ser. No. 16/518,321, which is incorporated herein by reference).

The cycle then continued with an examination subroutine in which each of four different nucleotides was individually delivered to the flow cell (Cy5 labeled dTTP, Cy5 labelled dATP, Cy5 labeled dCTP and Cy5 labeled dGTP), the system paused fluid flow to allow formation of ternary complex, the free nucleotide was removed from the flow cell by delivery of imaging fluid and then the flow cell was examined for ternary complex formation at the immobilized primer-template hybrids. The imaging fluid included LiCl, betaine, Tween-80, KCl, Ammonium Sulfate, hydroxylamine, and EDTA which stabilized the ternary complexes after removal of free nucleotides (see U.S. Pat No. 10,400,272, which is incorporated herein by reference). The flow cell was imaged via fluorescence microscopy to detect ternary complexes that contained a labeled nucleotide that was a cognate for the next correct nucleotide in each of the template nucleic acids. Reversible terminator moieties on the 3' nucleotides of the primer strands precluded nucleotide incorporation during the ternary complex formation and detection steps.

Following the examination subroutine, the flow cell was flushed with wash fluid to clear the flow cell of the nucleotides from the examination subroutine. Then the sequencing cycle continued with the cleavage step in which the reversible terminator moieties were removed from the primers using sodium acetate and sodium nitrite as set forth in U.S. Pat. No. 7,544,794, which is incorporated herein by reference. The cleavage reagent was then removed, and the flow cell was washed with imaging fluid to remove residual polymerase from the examination steps. The sequencing process then proceeded to the next nucleotide position by returning to the first step of the next sequencing cycle.

After performing 27 cycles of the above SBB™ method (with the first five cycles being control cycles), the extended primers produced by the sequencing reaction were capped using the capping reagents and methods set forth previously this Example.

Following capping, 5 cycles of the above SBB™ method were performed as a control to demonstrate the effectiveness of the capping process.

Following the 5 control cycles, a plurality of SHARK 276 primers (5'-CGGCGACCACCGAGATCGGCGAC-CACCGAGATCTACACTCTTTCCCTA-CACGACGCTCTTCCGATCT-3'; SEQ ID NO: 9) were hybridized to complementary primer binding sites in the adapter regions of the sense strand in the clusters. The sense strands of the clusters were sequenced using the SBB$^{TM}$ method that was used for the antisense strands.

Results

Figure 5:
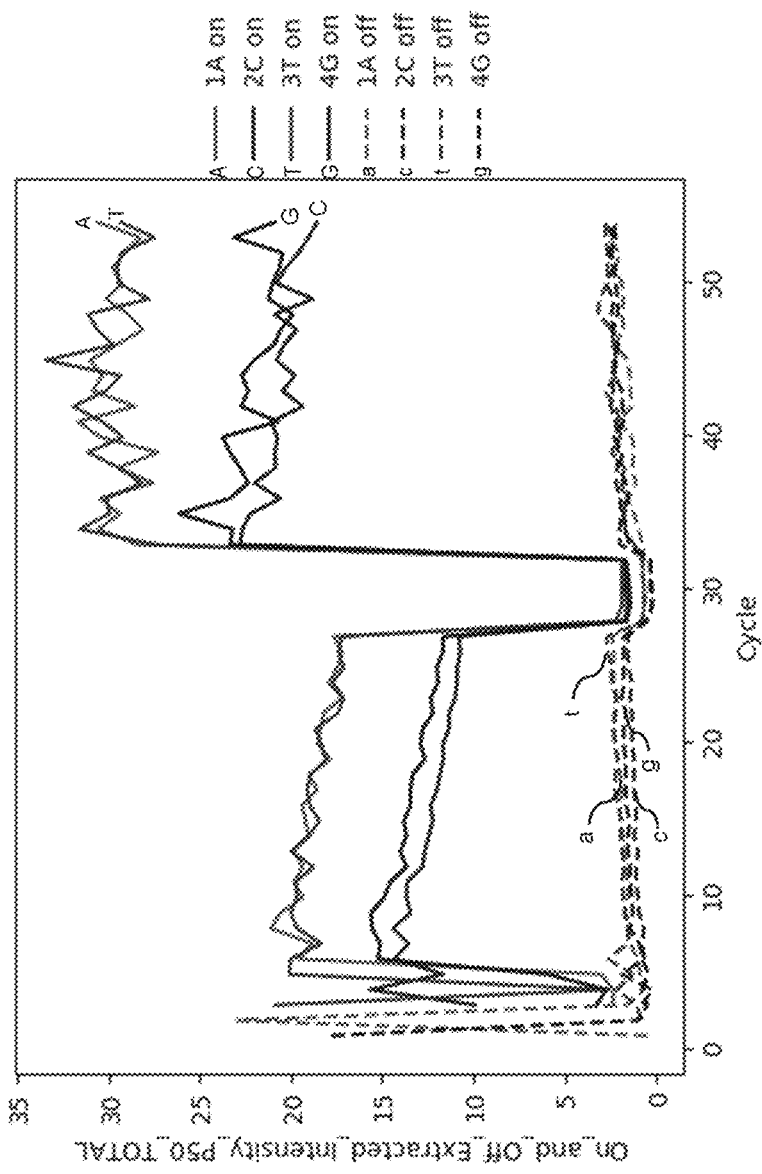
FIG. 5 shows aggregated extracted signal intensities acquired from sequencing 25 nucleotides from each of two strands at a plurality of nucleic acid sites in an array.

The results from the above sequencing process were analyzed as follows. The 'on' intensities (the brightest nucleotide signal intensity acquired from a given cluster in a given examination step) were tracked to monitor formation of ternary complex. FIG. 5 shows a plot of the $50^{th}$ percentile value of the normalized 'on' intensities on the y axis and cycle number on the x axis. Data from each of the four nucleotide types are plotted as separate lines, respectively. The data points for the first five cycles (control cycles) appeared noisy in both the 'on' and 'off' plots since the first five nucleotides were common between all of the clusters evaluated. The data points for later cycles were more informative regarding the signal-to-noise levels achieved during sequencing since each data point is an average encompassing of all four nucleotide types across multiple different templates.

The results of FIG. 5 demonstrate that antisense strand sequencing (cycles 6-27 in the plot) achieved excellent separation between 'on' and 'off' signals. These results indicated that the presence of the second strand in the cluster did not have a noticeably adverse impact on sequencing of the first strand. Moreover, signal decay during first strand sequencing was comparable to that observed previously for SBB™ performed on arrays having only a single strand at each site.

FIG. 5 shows that only negligible 'on' signals were detected during the 5 control cycles (cycles 28-32). This indicated effective 3' capping for the extended primers and other strands that were present after sequencing the antisense strands.

The results of FIG. 5 demonstrate that sense strand sequencing (cycles 33-54 in the plot) achieved excellent separation between 'on' and 'off' signals. Indeed the 'on' signals were higher on average for this second read compared to the first read, whilst the 'off' signals were comparable between the reads. These results indicated that the presence of the antisense strands in the cluster did not have a noticeably adverse impact on sequencing of the sense strand. Moreover, signal decay during first strand sequence reads was comparable to that observed from the second strand sequence reads.

A paired end alignment analysis was performed using Bowtie2 (Langmead B, Salzberg S. Fast gapped-read alignment with Bowtie 2. *Nature Methods*, 9:357-359 (2012), which is incorporated herein by reference) for a subset of sequenced clusters. For the analysis 574 reads were evaluated. Of these 574 (100.00%) were paired; 7 (1.22%) aligned concordantly 0 times; 567 (98.78%) aligned concordantly exactly 1 time and 0 (0.00%) aligned concordantly more than one time. A total of 7 read pairs aligned concordantly 0 times; of these, 4 (57.14%) aligned discordantly 1 time. A total of 3 read pairs aligned 0 times concordantly or discordantly; of these 6 mates made up the pairs; 2 (33.33%) aligned 0 times; 3 (50.00%) aligned exactly 1 time; and 1 (16.67%) aligned more than 1 time. Overall, 98.7% of paired end reads aligned concordantly, demonstrating accurate sense and antisense sequencing from individual clusters.

EXAMPLE II

Paired End Sequencing Via Two 100 Cycle Runs (PE 2×100)

This example confirms and extends the results of Example I, demonstrating that two strands can be read per cluster for at least 100 cycles per strand. The results confirm that both strands could be sequenced without the need for removing one strand to sequence the other.

Materials and Methods

Clusters were prepared using the simultaneous RCA & MDA methods set forth in Example I. Antisense and sense strands were sequenced as set forth in Example I, except that each strand was sequenced for 100 cycles.

Results

Figure 6:
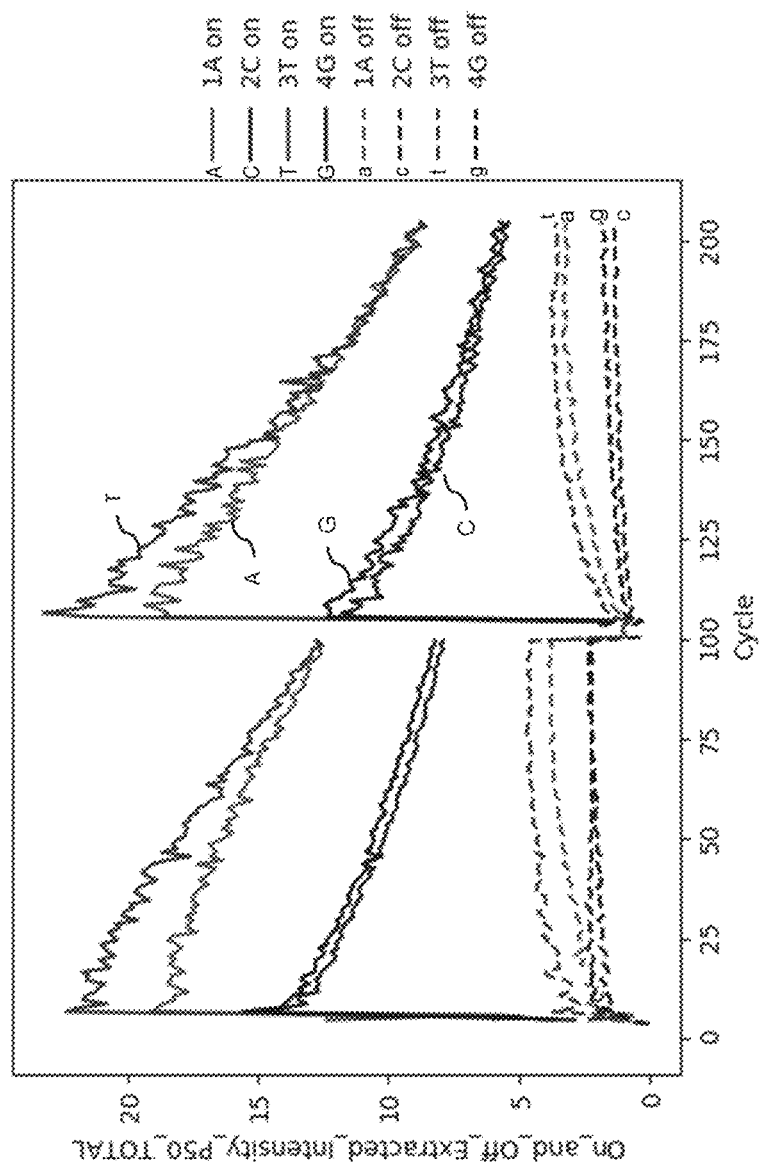
FIG. 6 shows aggregated extracted signal intensities acquired from sequencing 100 nucleotides from each of two strands at a plurality of nucleic acid sites in an array.

The sequencing results were analyzed as set forth in Example I. The results of FIG. 6 demonstrate that antisense strand sequencing (cycles 1-100 in the plot) achieved excellent separation between 'on' and 'off' signals, and further confirmed that signal decay during first strand sequencing (sequencing of the antisense strands) was comparable to that observed previously for SBB™ performed on arrays having only a single strand at each site. The results of the 5 control cycles (cycles 101-105 in the plot) indicated effective capping of 3' ends in the cluster after the first sequencing read. The results of sequencing the sense strands (cycles 106-205 in the plot) demonstrated excellent separation between 'on' and 'off' signals. These results indicated that the presence of the antisense strands in the cluster did not have a noticeably adverse impact on sequencing of the sense strand. Moreover, signal decay during first strand sequence reads was comparable to that observed from the second strand sequence reads.

TABLE 1

Analysis of strands independently

|  | Anti-sense Strand | Sense Strand |
| --- | --- | --- |
| Cluster Count | 28437 | 30835 |
| Percent clusters aligned | 90.03 | 91.8 |
| Q Score | 32.9 | 33.4 |

Figure 7:
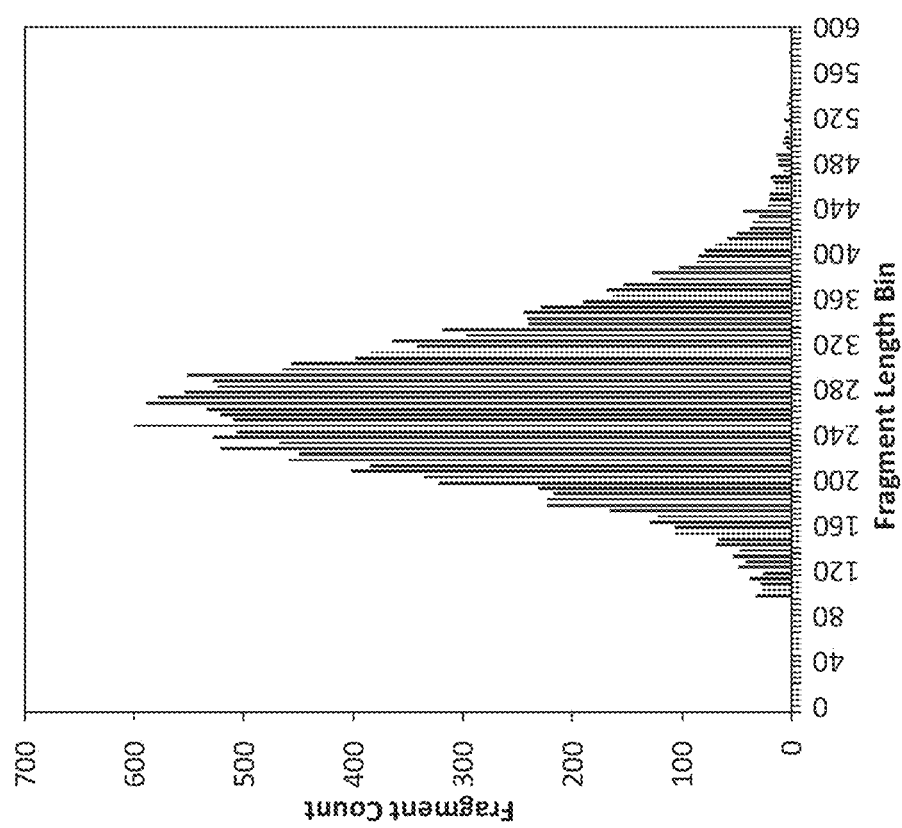
FIG. 7 shows a distribution of fragment lengths determined from paired end reads from sequencing 100 nucleotides from each of two strands at a plurality of nucleic acid sites in an array. Aggregated extracted signal intensities of sequencing the 100 nucleotides are illustrated in FIG. 6.

Bowtie 2 was used in combination with Omniome sequencing software to evaluate the paired end 100 cycle run. When each strand was independently analyzed, over 90% of reads were aligned to the reference genome (Table 1). Observed Q scores of 32.9 and 33.4 were observed for the antisense and sense strands, respectively (Table 1). Additionally, Bowtie 2 was used to analyze paired end reads as mate pairs. In this case 81.9% of read pairs were mapped concordantly to the reference genome (Table 2). Mate pair distances calculated by Bowtie 2 were plotted as a distribution to further demonstrate, along with the number of concordant read pairs, the specificity of priming and sequencing both strands of DNA within each cluster. See FIG. 7 which demonstrates that the clusters were sequenced from opposite ends of the library fragments. Mate pair distances were mapped and were consistent with the original fragment size expected for the library that was sequenced.

TABLE 2

Bowtie 2 Analysis

|  | % of Total |
| --- | --- |
| Read pairs aligned concordantly | 81.92% |
| Reads aligned discordantly | 0.65% |
| One mate of a pair aligns | 3.79% |
| Total alignment | 84.46% |

A paired end alignment analysis was performed using Bowtie 2 for a subset of sequenced clusters. For the analysis 21418 reads were evaluated. Of these 21418 (100.00%) were paired; 3873 (18.08%) aligned concordantly 0 times; 17545 (81.92%) aligned concordantly exactly 1 time and 0 (0.00%) aligned concordantly more than 1 time. Of the 3873 pairs that aligned concordantly 0 times, 138 (3.56%) aligned discordantly 1 time. Of the reads, 3735 pairs aligned 0 times concordantly or discordantly; 7470 mates made up the pairs; 6657 (89.12%) aligned 0 times; 813 (10.88%) aligned exactly 1 time and 0 (0.00%) aligned more than 1 time.

EXAMPLE III

Figure 8B:
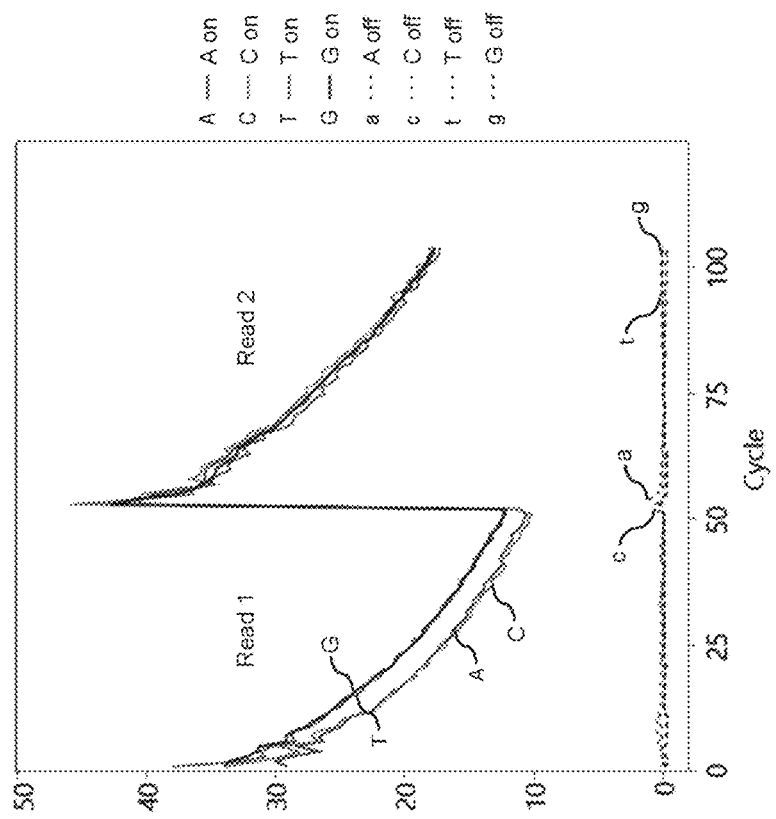
FIGS. 8A-8B show the sequencing methods using RCA and MDA of the present disclosure with capture primers and amplification primers attached to a solid support, are not biased towards target sequences of certain sizes and can generate high quality reads.
Figure 8A:
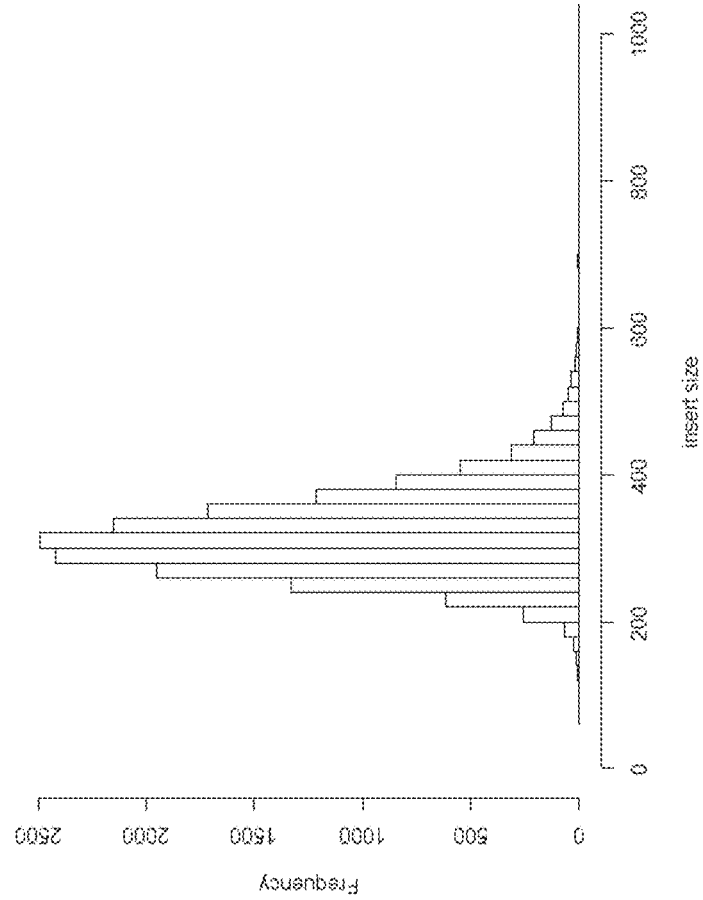

Enzymatic Digestion of Second Strands and Primer Extension Products Prior to Sequencing First Strands The first strands and the second strands containing concatemers of target sequences (inserts) were generated with RCA and MDA as described herein with reference to FIGS. 1E such that the second strands contained bases that were uracil. 3' ends of the antisense strands included biotin conjugated nucleotides. The 3' ends of the antisense strands were blocked by streptavidin binding to the biotin conjugated nucleotides. After priming the second strands with sequencing primers and sequencing the second strands using extended sequencing primers, the second strands and the extended sequencing primers were digested enzymatically as described herein with reference to FIG. 2D. Uracil DNA glycosylase (UDG) and Endonuclease VIII were used to generate nicks in the second strands. T7 Exonuclease was used to digest the remaining antisense strands and the extended primers from the 5' termini (the 5' termini of the antisense strands and the extended primers, and the 5' termini at nicks of the antisense strands). The sizes of the target sequences were determined using paired end reads. FIG. 8A is a histogram showing that the method had no bias towards target sequences of certain sizes. Sequencing fluorescence intensity for paired reads is presented in FIG. 8B. 50 cycles were run for each reaction in the pair. One sees that the second read signal intensity is comparable to that of the first read, demonstrating the effectiveness of the methods herein in generating colonies suitable for paired read sequencing.

EXAMPLE IV

Figures 9A, 9B:
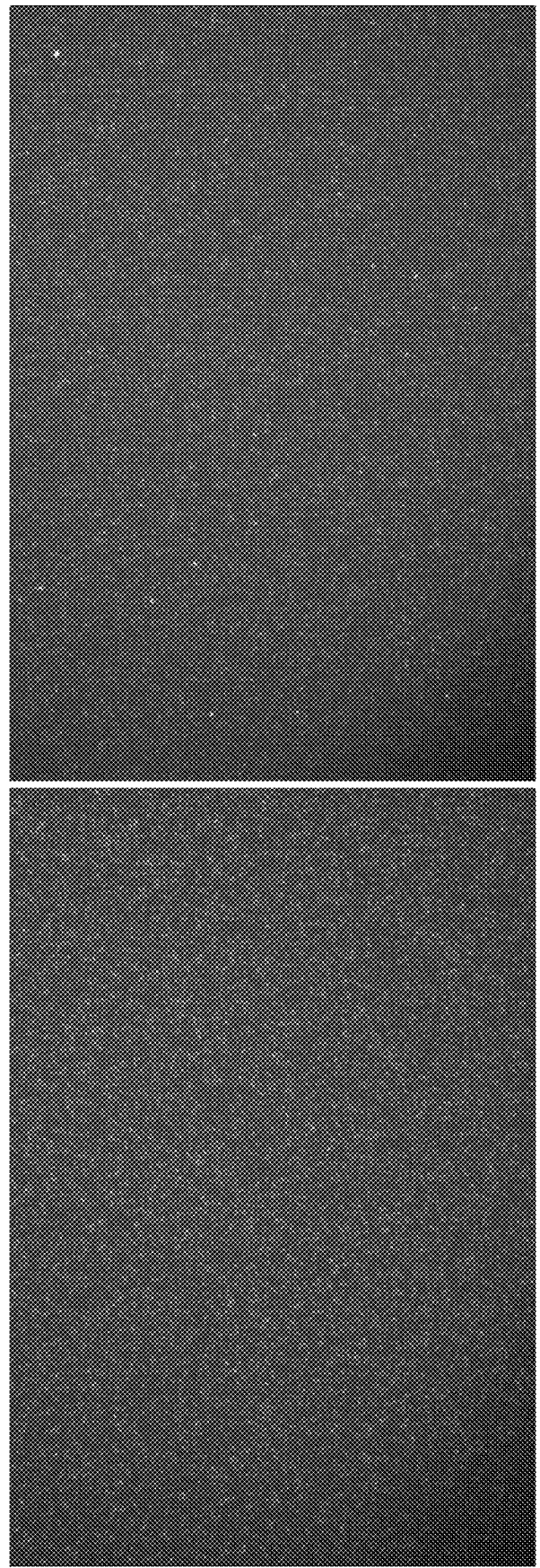
FIG. 9A shows high quality signal densities of sequencing first strands generated from a nucleic acid template using rolling circle amplification with capture primers attached to a solid support.
FIG. 9B shows high quality signal densities of sequencing second strands generated from first strands using multiple displacement amplification with amplification primers attached to a solid support, where the first strands were generated from a nucleic acid template using rolling circle amplification with capture primers attached to the solid support.

Rolling Circle Amplification and Multiple Displacement Amplification with Capture Primers and Amplification Primers Attached to a Solid Surface FIG. 9A shows high quality signal densities of sequencing first strands generated from a nucleic acid template using rolling circle amplification with capture primers attached to a solid support. FIG. 9B shows high quality signal densities of sequencing second strands generated from first strands using multiple displacement amplification with amplification primers attached to a solid support, where the first strands were generated from a nucleic acid template using rolling circle amplification with capture primers attached to the solid support.

Throughout this application various publications, patents and/or patent applications have been referenced. The disclosures of these documents in their entireties are hereby incorporated by reference in this application.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

A number of embodiments have been described. Nevertheless, it will be understood that various modifications may be made. Accordingly, other embodiments are within the scope of the following claims.

---

What is claimed is:

1. A method for determining a sequence, comprising
   (a) providing a nucleic acid cluster comprising a concatemer attached to a solid support, wherein the concatemer comprises multiple copies of a sequence unit linked in series, and wherein the sequence unit comprises a target sequence and a primer binding site;
   (b) hybridizing a sequencing primer to a primer binding site in a sequence unit of a strand of the concatemer, wherein the strand is covalently attached to the solid support;
   (c) extending the sequencing primer along the strand to determine the target sequence from at least a portion of the target sequence in the strand;
   (d) digesting the strand;
   (e) hybridizing another sequencing primer to a primer binding site in a sequence unit of another strand of the concatemer, wherein the strand and the other strand are the reverse complements of one another, and wherein the strand and the other strand are formed by rolling circle amplification (RCA) and multiple displacement amplification (MDA); and
   (f) extending the other sequencing primer along the other strand to determine the target sequence from at least a portion of the target sequence in the other strand.

2. The method of claim 1, wherein the primer binding site to which the sequencing primer hybridizes to and the primer binding site to which the other sequencing primer hybridizes to are different.

3. The method of claim 1, further comprising generating the other strand of the concatemer from the strand of the concatemer, optionally wherein generating the other strand comprises generating the other strand using an amplification primer that hybridizes to a primer binding site in a sequence unit of the strand.

4. The method of claim 1, wherein the extending of the sequencing primer in step (c) and/or extending the other sequencing primer in step (f) comprises repeated cycles of (i) adding a reversibly terminated nucleotide to the primer and (ii) deblocking the reversibly terminated nucleotide on the primer.

5. The method of claim 4, wherein the extending of the sequencing primer in step (c) and/or step (f) comprises at least 100 of the repeated cycles to determine the target sequence from at least 100 bases of the target sequence in the strand.

6. The method of claim 1, wherein step (a) comprises
(i) providing a solid support comprising a capture primer;
(ii) hybridizing a nucleic acid template to the capture primer; and
(iii) generating the strand by extending the capture primer along the circular nucleic acid template by rolling circle amplification.

7. The method of claim 6, wherein step (a) further comprises generating the other strand using an amplification primer that binds to a primer binding site in a sequence unit of the strand.

8. The method of claim 7, wherein the primer binding site to which the amplification primer hybridizes to is different from the primer binding site to which the sequencing primer hybridizes to and the primer binding site to which the other sequencing primer hybridizes.

9. The method of claim 6, wherein the nucleic acid template is a circular nucleic acid template.

10. The method of claim 6, further comprises circularizing the nucleic acid template prior to step (a)(iii).

11. The method of claim 1, wherein the cluster comprises multiple copies of the other strand of the concatemer.

12. The method of claim 1, wherein a first portion of the target sequence is determined from the strand and a second portion of the target sequence is determined from the other strand.

13. The method of claim 1, wherein the strand comprises one or more nucleotides that are modified or non-canonical and/or one or more nucleotides with bases that are modified or non-canonical, optionally wherein the bases that are modified or non-canonical are uracil.

14. The method of claim 13, wherein the strand is generated by extending a capture primer in the presence of deoxyribonucleotide triphosphates comprising dATP, dTTP, dGTP, dCTP, and a modified or non-canonical deoxyribonucleotide triphosphate, optionally wherein the non-canonical deoxyribonucleotide trisphosphate is dUTP.

15. The method of claim 14, wherein the ratio of the modified or non-canonical deoxyribonucleotide trisphosphate in the strand to another deoxyribonucleotide triphosphate or all other deoxyribonucleotide triphosphates in the strand is from about 1:1000 to about 1:10.

16. The method of claim 14, wherein the concentration of the modified or non-canonical deoxyribonucleotide trisphosphate is from about 0.01 mM to about 1 mM.

17. The method of claim 1, wherein the digesting is performed using Uracil DNA glycosylase (UDG).

18. A method for determining a sequence, comprising
digesting a strand of a concatemer attached to a solid support, wherein the concatemer comprises multiple copies of a sequence unit linked in series, wherein the sequence unit comprises a target sequence and a primer binding site, wherein the strand is covalently attached to the solid support, wherein the concatemer is formed by rolling circle amplification (RCA) and multiple displacement amplification (MDA);
hybridizing a sequencing primer to a primer binding site in a sequence unit of another strand of the concatemer, wherein the strand and the other strand are the reverse complements of one another; and
extending the sequencing primer along the other strand to determine the target sequence from at least a portion of the target sequence in the other strand.

19. The method of claim 18, further comprising determining the target sequence of at least a portion of the strand prior to digesting the strand.

* * * * *

SEQUENCE LISTING

```
Sequence total quantity: 9
SEQ ID NO: 1            moltype = AA  length = 10
FEATURE                 Location/Qualifiers
REGION                  1..10
                        note = Synthetic Polypeptide
source                  1..10
                        mol_type = protein
                        organism = synthetic construct
SEQUENCE: 1
EQKLISEEDL                                                                      10

SEQ ID NO: 2            moltype = AA  length = 26
FEATURE                 Location/Qualifiers
REGION                  1..26
                        note = Synthetic Polypeptide
source                  1..26
                        mol_type = protein
                        organism = synthetic construct
SEQUENCE: 2
KRRWKKNFIA VSAANRFKKI SSSGAL                                                    26

SEQ ID NO: 3            moltype = AA  length = 7
FEATURE                 Location/Qualifiers
REGION                  1..7
                        note = Synthetic Polypeptide
source                  1..7
                        mol_type = protein
                        organism = synthetic construct
SEQUENCE: 3
DYKDDDD                                                                         7

SEQ ID NO: 4            moltype = AA  length = 8
FEATURE                 Location/Qualifiers
REGION                  1..8
                        note = Synthetic Polypeptide
source                  1..8
                        mol_type = protein
                        organism = synthetic construct
SEQUENCE: 4
DYKDDDDK                                                                        8
```

```
SEQ ID NO: 5              moltype = AA  length = 7
FEATURE                   Location/Qualifiers
REGION                    1..7
                          note = Synthetic Polypeptide
source                    1..7
                          mol_type = protein
                          organism = synthetic construct
SEQUENCE: 5
DYKDDDK                                                                    7

SEQ ID NO: 6              moltype = DNA  length = 26
FEATURE                   Location/Qualifiers
misc_feature              1..26
                          note = Synthetic Oligonucleotide
misc_feature              24..25
                          note = phosphorothiate bond
misc_feature              25..26
                          note = phosphorothiate bond
source                    1..26
                          mol_type = other DNA
                          organism = synthetic construct
SEQUENCE: 6
cgccgtatca ttcaagcaga agacgg                                              26

SEQ ID NO: 7              moltype = DNA  length = 24
FEATURE                   Location/Qualifiers
misc_feature              1..24
                          note = Synthetic Oligonucleotide
misc_feature              23..24
                          note = phosphorothiate bond
source                    1..24
                          mol_type = other DNA
                          organism = synthetic construct
SEQUENCE: 7
atctcgtatg ccgtcttctg cttg                                                24

SEQ ID NO: 8              moltype = DNA  length = 28
FEATURE                   Location/Qualifiers
misc_feature              1..28
                          note = Synthetic Oligonucleotide
source                    1..28
                          mol_type = other DNA
                          organism = synthetic construct
SEQUENCE: 8
gtgactggag ttcagacgtg tgctcttc                                            28

SEQ ID NO: 9              moltype = DNA  length = 67
FEATURE                   Location/Qualifiers
misc_feature              1..67
                          note = Synthetic Oligonucleotide
source                    1..67
                          mol_type = other DNA
                          organism = synthetic construct
SEQUENCE: 9
cggcgaccac cgagatcggc gaccaccgag atctacactc tttccctaca cgacgctctt         60
ccgatct                                                                   67
```